US012778893B2

(12) United States Patent
Niwa et al.

(10) Patent No.: US 12,778,893 B2
(45) Date of Patent: Nov. 3, 2026

(54) NUCLEIC ACID LIPID PARTICLE VACCINE ENCAPSULATING HPV MRNA

(71) Applicants: DAIICHI SANKYO COMPANY, LIMITED, Tokyo (JP); NATIONAL INSTITUTES OF BIOMEDICAL INNOVATION, HEALTH AND NUTRITION, Osaka (JP)

(72) Inventors: Takako Niwa, Tokyo (JP); Takashi Suzuki, Tokyo (JP); Makoto Koizumi, Tokyo (JP); Nao Jonai, Tokyo (JP); Yoshikuni Onodera, Tokyo (JP); Fumihiko Takeshita, Tokyo (JP); Ken Ishii, Osaka (JP)

(73) Assignees: DAIICHI SANKYO COMPANY, LIMITED, Tokyo (JP); NATIONAL INSTITUTES OF BIOMEDICAL INNOVATION, HEALTH AND NUTRITION, Osaka (JP)

( * ) Notice: Subject to any disclaimer, the term of this patent is extended or adjusted under 35 U.S.C. 154(b) by 1188 days.

(21) Appl. No.: 17/776,743

(22) PCT Filed: Nov. 13, 2020

(86) PCT No.: PCT/JP2020/042405

§ 371 (c)(1),
(2) Date: May 13, 2022

(87) PCT Pub. No.: WO2021/095838

PCT Pub. Date: May 20, 2021

(65) Prior Publication Data

US 2022/0409540 A1 Dec. 29, 2022

(30) Foreign Application Priority Data

Nov. 15, 2019 (JP) ................................ 2019-207001

(51) Int. Cl.

| | |
|---|---|
| ***A61K 9/16*** | (2006.01) |
| ***A61K 39/12*** | (2006.01) |
| *A61K 39/00* | (2006.01) |

(52) U.S. Cl.

CPC ............ *A61K 9/1617* (2013.01); *A61K 39/12* (2013.01); *A61K 2039/53* (2013.01); *C12N 2710/20034* (2013.01)

(58) Field of Classification Search

CPC .. A61K 9/1617; A61K 39/12; A61K 2039/53; A61K 2039/55555; A61K 2039/572; A61K 2039/575; A61K 2039/585; A61K 47/543; A61K 47/6929; A61K 47/28; A61K 47/34; A61K 9/14; A61K 9/50; A61K 47/18; A61K 47/24; A61K 47/54; A61K 48/00; A61K 48/0033; C12N 2710/20034; C12N 15/67; C12N 15/88; C12N 2710/20022; C12N 15/62;

(Continued)

(56) References Cited

U.S. PATENT DOCUMENTS

| | | | | |
|---|---|---|---|---|
| 9,803,199 B2 * | 10/2017 | Koizumi | ................ | A61K 9/127 |
| 10,533,176 B2 * | 1/2020 | Koizumi | ................ | A61K 47/22 |
| 2005/0031638 A1 | 2/2005 | Dalemans et al. | | |
| 2016/0038584 A1 | 2/2016 | Weiner et al. | | |

FOREIGN PATENT DOCUMENTS

| | | |
|---|---|---|
| JP | 2014-530610 | 11/2014 |
| JP | 2016-512553 A | 4/2016 |

(Continued)

OTHER PUBLICATIONS

English translation of WO 2015/005253 A1, accessed on Aug. 26, 2025 (Year: 2015).*

Yijayachari et al. Human Vacc. Imuunother. 2015, 11 (8), 1945. (Year: 2015).*

(Continued)

*Primary Examiner* — David J Blanchard

*Assistant Examiner* — Sean J Steinke

(74) *Attorney, Agent, or Firm* — Dorsey & Whitney LLP

(57) ABSTRACT

The present invention provides a vaccine for preventing and/or treating infections with human papillomavirus. The present invention relates to a lipid particle encapsulating a nucleic acid molecule capable of expressing the E6 and E7 antigens of human papillomavirus, wherein the lipid comprises a cationic lipid represented by general formula (Ia) or a pharmaceutically acceptable salt thereof:

[Formula 1]

(Ia)

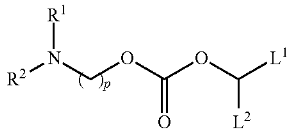

wherein $R^1$ and $R^2$ each independently represent a $C_1$-$C_3$ alkyl group;

$L^1$ represents a $C_{17}$-$C_{19}$ alkenyl group which may have one or a plurality of $C_2$-$C_4$ alkanoyloxy groups;

$L^2$ represents a $C_{10}$-$C_{19}$ alkyl group which may have one or a plurality of $C_2$-$C_4$ alkanoyloxy groups or a $C_{10}$-$C_{19}$ alkenyl group which may have one or a plurality of $C_2$-$C_4$ alkanoyloxy groups; and p is 3 or 4.

27 Claims, 12 Drawing Sheets

Specification includes a Sequence Listing.

(58) Field of Classification Search
CPC ......... C12N 15/63; Y02A 50/30; A61P 35/00; A61P 31/20; C07K 14/005; C07K 14/025
See application file for complete search history.

(56) References Cited

FOREIGN PATENT DOCUMENTS

| | | | | | |
|---|---|---|---|---|---|
| WO | WO 2014/165291 | A1 | | 10/2014 | |
| WO | 2015005253 | A1 | | 1/2015 | |
| WO | WO 2016/037053 | A1 | | 3/2016 | |
| WO | WO-2016198531 | A2 | * | 12/2016 | ........... C07K 14/025 |
| WO | WO-2018081459 | A1 | * | 5/2018 | ......... A61K 31/7088 |
| WO | WO 2018/144775 | A1 | | 8/2018 | |

OTHER PUBLICATIONS

Yan et al. Mol. Therapy 2007, 15 (1), 411. (Year: 2007).*

Japanese Patent Office, "Office Action" in Japanese, mailed Dec. 11, 2024, for Japanese Application No. 2021-556166 citing JP 2014-530610, 4 pages.

Bosch et al., "Prevalence of Human Papillomavirus in Cervical Cancer: a Worldwide Perspective," *J. Natl. Cancer Inst.*, (1995), 87(11):796-802.

Boyer et al., "E7 Protein of Human Papilloma Virus-16 Induces Degradation of Retinoblastoma Protein through the Ubiquitin-Proteasome Pathway," *Cancer Research*, (1996), 56:4620-4624.

De Villiers, "Cross-roads in the classification of papillomaviruses," *Virology*, (2013), 445:2-10.

Doorbar, "The papillomavirus life cycle," *Journal of Clinical Virology*, (2005), 32S:S7-S15.

Edmonds et al., "A Point Mutational Analysis of Human Papillomavirus Type 16 E7 Protein," *Journal of Virology*, (1989), 63(6):2650-2656.

Foster et al., "The Ability of Human Papillomavirus E6 Proteins to Target p53 for Degradation In Vivo Correlates with Their Ability to Abrogate Actinomycin D-Induced Growth Arrest," *Journal of Virology*, (1994), 68(9):5698-5705.

Harper et al., "HPV vaccines—a review of the first decade," *Gynecologic Oncology*, (2017), 146:196-204.

Jewers et al., "Regions of Human Papillomavirus Type 16 E7 Oncoprotein Required for Immortalization of Human Keratinocytes," *Journal of Virology*, (1992), 66(3):1329-1335.

Kines et al., "The initial steps leading to papillomavirus infection occur on the basement membrane prior to cell surface binding," *Proc. Natl. Acad. Sci. USA*, (2009), 106(48):20458-20463.

Roden et al., "How will HPV vaccines affect cervical cancer?," *Nature Reviews | Cancer*, (2006), 6:753-763.

Scheffner et al., "The E6 Oncoprotein Encoded by Human Papillomavirus Types 16 and 18 Promotes the Degradation of p53," *Cell* (1990), 63:1129-1136.

Taiwan Intellectual Property Office, Office Action with Search Report, mailed May 7, 2024, for Taiwan Application No. 109139801, 9 pages.

European Patent Office, "Communication and Supplementary European Search Report," mailed Jan. 16, 2024, for European Application No. 20887577.3, 8 pages.

Schiller, J., "Human papilloma virus vaccines," Abstracts of the Interscience Conference on Antimicrobial Agents and Chemotherapy, (2003), 43:528 (Abstract).

English Translation of PCT International Search Report mailed Jan. 4, 2021, for PCT Application No. PCT/JP2020/042405, 3 pages.

* cited by examiner

NUCLEIC ACID LIPID PARTICLE VACCINE ENCAPSULATING HPV MRNA

This application is a national stage application under 35 U.S.C. § 371 of International Application No. PCT/JP2020/042405, filed Nov. 13, 2020, entitled "NUCLEIC ACID LIPID PARTICLE VACCINE ENCAPSULATING HPV mRNA," which claims priority to Japanese Patent Application No. 2019-207001, filed Nov. 15, 2019.

TECHNICAL FIELD

The present invention relates to a nucleic acid lipid particle vaccine encapsulating HPV mRNA.

BACKGROUND ART

Human papillomavirus (HPV) is a virus that has a circular, double-stranded DNA molecule as its genome without envelope membrane, and there are about 200 genotypes of this virus (Non-Patent Document No. 1). Among them, some genotypes transform infected cells to cancer cells. In particular, genotype 16 (HPV16) and genotype 18 (HPV18) are classified as high risk types and have been demonstrated to be associated with development of cancer represented by cervical cancer (Non-Patent Document No. 2).

The HPV genome has eight genes encoding viral proteins, which are classified into early genes (E1, E2, E4, E5 E6 and E7) and late genes (L1 and L2) according to the stage of their expression in viral life cycle. Early genes regulate viral replication and transformation of infected cells to cancer cells, while L1 and L2 are structural proteins which form a virus particle capsid (Non-Patent Document No. 3).

HPV infects keratinocyte progenitor cells which are present in the basal lamina of squamous epithelium. The HPV infection is initiated by adsorption of the capsid L1 protein to heparan sulfate proteoglycans which are present on surfaces of host cell membranes (Non-Patent Document No. 4). Since neutralizing antibodies in charge of defense against HPV infection target the L1 protein, the preventive vaccines currently available in the market contain a VLP (virus-like particle) antigen consisting of the L1 protein as a medicinal ingredient. Further, all of the three existing preventive vaccines contain L1 VLP antigens derived from HPV16 and HPV18. Although any of these vaccines has a preventive effect of 95% or more against HPV16 and HPV18 in adolescent populations naïve for HPV infection, these vaccines do not exhibit a therapeutic effect on cervical cancer or cervical dysplasia as a precancerous condition (Non-Patent Document No. 5).

Cells infected with HPV undergo abnormalities in their cell cycle due to oncoproteins E6 and E7. This occurs because the abnormalities are attributed to the inhibition of the functions of p53 and pRb involved in cell cycle or the induction of apoptotic cell death by E6 and E7 (Non-Patent Documents Nos. 6 and 7). Since the regions of E6 and E7 important for carcinogenic activity have been elucidated, it is possible to enhance the safety of vaccines by inserting mutations into these regions for inactivation when E6 and E7 are used as vaccine antigens (Non-Patent Documents Nos. 8 to 10).

Host protective immunity against HPV infection depends on induction of neutralizing antibodies as well as that of cytotoxic T cells (CTL) and helper T cells. In particular, E6 and E7, the non-structural proteins, are target antigens for CTL induction, and thus draw attention as antigens for therapeutic vaccines against cervical cancer and cervical dysplasia caused by HPV infection (Non-Patent Document No. 11).

Patent Document No. 1 discloses the nucleotide sequences of the genes for E6/E7 fusion antigens derived from HPV genotypes 6, 11, 16, 18, 31, 33, 39, 45, 52 and 58. The nucleotide sequences disclosed in this document have those for the IgE leader sequence added to the N terminus of E6 and a furin peptidase cleavage site inserted between the E6 and E7 coding regions. Further, mutations are inserted into the p53 binding region of E6 and the pRb binding region of E7 to thereby inactivate the carcinogenic activity of E6 and E7. These sequences are introduced into expression plasmids for mammals, and their medicinal efficacy as a DNA gene vaccine against HPV is evaluated in a mouse model. Immunization is conducted by intramuscular administration of the vaccine into the thigh of a mouse using electroporation.

PRIOR ART LITERATURE

Non-Patent Documents

Non-Patent Document No. 1: Virology 2013; 445:2e10.

Non-Patent Document No. 2: J Natl Cancer Inst 1995; 87:796-802.

Non-Patent Document No. 3: J Clin Virol 2005; 32 (Suppl.1):S7e15.

Non-Patent Document No. 4: Proc Natl Acad Sci U.S.A 2009; 106:20458e63.

Non-Patent Document No. 5: Gynecologic Oncology 146 (2017) 196-204

Non-Patent Document No. 6: Cell 1990; 63:1129e36

Non-Patent Document No. 7: Cancer Res 1996; 56:4620e4.

Non-Patent Document No. 8: J Virol, 1989, p. 2650-2656

Non-Patent Document No. 9: J Virol, 1992, p. 1329-1335

Non-Patent Document No. 10: J Virol, 1994, p. 5698-5705

Non-Patent Document No. 11: Nat Rev Cancer. 2006, 6(10): 753-763

Patent Document No. 1: JP 2016-512553

DISCLOSURE OF THE INVENTION

Problem for Solution by the Invention

It is an object of the present invention to provide a vaccine for preventing and/or treating infections with human papillomavirus (HPV).

Means to Solve the Problem

The present inventors administered a lipid particle encapsulating an mRNA molecule encoding the E6 and E7 antigens of HPV to cancer cell-transplanted mice and found that a regression effect in the cancer was observed. The present invention has been achieved based on this finding.

A summary of the present invention is described as below.

(1) A lipid particle encapsulating a nucleic acid molecule capable of expressing the E6 and E7 antigens of human papillomavirus, wherein the lipid comprises a cationic lipid represented by general formula (Ia) or a pharmaceutically acceptable salt thereof:

[Formula 1]

(Ia)

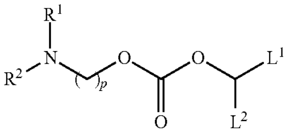

wherein $R^1$ and $R^2$ each independently represent a $C_1$-$C_3$ alkyl group;

$L^1$ represents a $C_{17}$-$C_{19}$ alkenyl group which may have one or a plurality of $C_2$-$C_4$ alkanoyloxy groups;

$L^2$ represents a $C_{10}$-$C_{19}$ alkyl group which may have one or a plurality of $C_2$-$C_4$ alkanoyloxy groups or a $C_{10}$-$C_{19}$ alkenyl group which may have one or a plurality of $C_2$-$C_4$ alkanoyloxy groups; and p is 3 or 4.

(2) The particle of (1) above, wherein both $R^1$ and $R^2$ in general formula (Ia) are a methyl group.

(3) The particle of (1) or (2) above, wherein p in general formula (Ia) is 3.

(4) The particle of any one of (1) to (3) above, wherein $L^1$ in general formula (Ta) is a $C_{17}$-$C_{19}$ alkenyl group which may have one or a plurality of acetoxy groups.

(5) The particle of any one of (1) to (4) above, wherein $L^2$ in general formula (Ta) is a $C_{10}$-$C_{12}$ alkyl group which may have one or a plurality of acetoxy groups or a $C_{10}$-$C_{19}$ alkenyl group which may have one or a plurality of acetoxy groups.

(6) The particle of any one of (1) to (4) above, wherein $L^2$ in general formula (Ta) is a $C_{10}$-$C_{12}$ alkyl group which may have one or a plurality of acetoxy groups or a $C_{17}$-$C_{19}$ alkenyl group which may have one or a plurality of acetoxy groups.

(7) The particle of any one of (1) to (6) above, wherein $L^1$ in general formula (Ta) is an (R)-11-acetyloxy-cis-8-heptadecenyl group, a cis-8-heptadecenyl group or a (8Z,11Z)-heptadecadienyl group.

(8) The particle of any one of (1) to (7) above, wherein $L^2$ in general formula (Ta) is a decyl group, a cis-7-decenyl group, a dodecyl group or an (R)-11-acetyloxy-cis-8-heptadecenyl group.

(9) The particle of (1), wherein the cationic lipid is represented by the following structural formula:

[Formula 2]

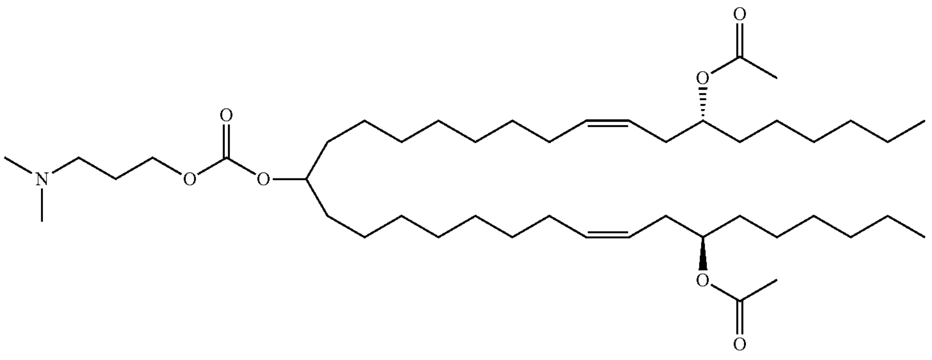

(10) The particle of (1), wherein the cationic lipid is represented by the following structural formula:

[Formula 3]

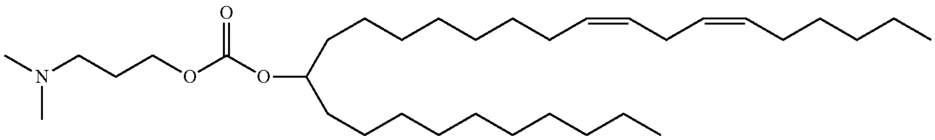

(11) The particle of (1), wherein the cationic lipid is represented by the following structural formula:

[Formula 4]

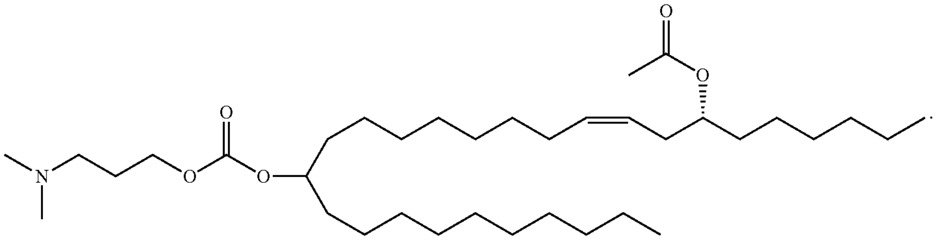

(12) The particle of any one of (1) to (11) above, wherein the lipid further comprises amphipathic lipids, sterols and PEG lipids.

(13) The particle of (12) above, wherein the amphipathic lipid is at least one selected from the group consisting of distearoyl phosphatidylcholine, dioleoyl phosphatidylcholine and dioleoyl phosphatidylethanolamine.

(14) The particle of (12) or (13) above, wherein the sterol is cholesterol.

(15) The particle of any one of (12) to (14) above, wherein the PEG lipid is 1,2-dimyristoyl-sn-glycerol methoxypolyethylene glycol and/or N-[methoxy poly(ethyleneglycol) 2000]carbamoyl]-1,2-dimyristyloxypropyl-3-amine.

(16) The particle of any one of (12) to (15) above, wherein the lipid composition of the amphipathic lipid, the sterol, the cationic lipid and the PEG lipid is 15% or less of the amphipathic lipid, 20 to 55% of the sterol, 40 to 65% of the cationic lipid and 1 to 5% of the PEG lipid in terms of molar quantity; and the ratio of the total lipid weight to the weight of nucleic acid is 15 to 30.

(17) The particle of (16) above, wherein the lipid composition of the amphipathic lipid, the sterol, the cationic lipid and the PEG lipid is 5 to 15% of the amphipathic lipid, 35 to 50% of the sterol, 40 to 55% of the cationic lipid and 1 to 3% of the PEG lipid in terms of molar quantity; and the ratio of the total lipid weight to the weight of nucleic acid is 15 to 25.

(18) The particle of (17) above, wherein the lipid composition of the amphipathic lipid, the sterol, the cationic lipid and the PEG lipid is 10 to 15% of the amphipathic lipid, 35 to 45% of the sterol, 40 to 50% of the cationic lipid and 1 to 2% of the PEG lipid in terms of molar quantity; and the ratio of the total lipid weight to the weight of nucleic acid is 17.5 to 22.5.

(19) The particle of (18) above, wherein the lipid composition of the amphipathic lipid, the sterol, the cationic lipid and the PEG lipid is 10 to 15% of the amphipathic lipid, 35 to 45% of the sterol, 45 to 50% of the cationic lipid and 1.5 to 2% of the PEG lipid in terms of molar quantity; and the ratio of the total lipid weight to the weight of nucleic acid is 17.5 to 22.5.

(20) The particle of any one of (1) to (19) above, wherein the human papillomavirus is HPV16.

(21) The particle of (20) above, wherein the human papillomavirus is HPV16 and the E6 antigen thereof consists of an amino acid sequence having at least 95% identity with the amino acid sequence as shown in SEQ ID NO: 8.

(22) The particle of (20) or (21) above, wherein the human papillomavirus is HPV16 and the E7 antigen thereof consists of an amino acid sequence having at least 95% identity with the amino acid sequence as shown in SEQ ID NO: 9.

(23) The particle of any one of (20) to (22) above, wherein the human papillomavirus is HPV16 and the nucleic acid molecule capable of expressing the E6 and E7 antigens of HPV16 is an mRNA molecule comprising a cap structure (Cap), 5' untranslated region (5'-UTR), a leader sequence, E6 coding region, a protease cleavage sequence (furin cleavage site), E7 coding region, 3' untranslated region (3'-UTR) and a polyA tail (polyA).

(24) The particle of (23) above, wherein the sequence of the nucleic acid molecule capable of expressing the E6 and E7 antigens of HPV16 consists of a nucleotide sequence having at least 90% identity with any one of the sequences as shown in SEQ ID NOS: 2, 4 or 6.

(25) The particle of any one of (1) to (24) above, wherein the nucleic acid molecule comprises at least one modified nucleotide.

(26) The particle of (25) above, wherein the modified nucleotide comprises at least one of 5-substituted pyrimidine nucleotide and/or pseudouridine optionally substituted at position 1.

(27) The particle of (25) above, wherein the modified nucleotide comprises at least one selected from the group consisting of 5-methylcytidine, 5-methoxyuridine, 5-methyluridine, pseudouridine and 1-alkylpseudouridine.

(28) The particle of any one of (1) to (27) above, wherein the mean particle size is 30 nm to 300 nm.

(29) Use of the particle of any one of (1) to (28) above for manufacturing a composition for preventing and/or treating infections with human papillomavirus.

(30) The use of (29) above, wherein the infections are infections with HPV16.

(31) A composition comprising the particle of any one of (1) to (28) above.

(32) The composition of (31) above for allowing the expression of the E6 and E7 antigens of human papillomavirus in vivo or in vitro.

(33) The composition of (31) or (32) above for use as a pharmaceutical drug.

(34) The composition of (33) above for inducing immune response to human papillomavirus.

(35) The composition of (33) or (34) above for preventing and/or treating infections with human papillomavirus.

(36) A method of expressing the E6 and E7 antigens of human papillomavirus in vitro, comprising introducing into cells the composition of (31) or (32) above.

(37) A method of expressing the E6 and E7 antigens of human papillomavirus in vivo, comprising administering to a mammal the composition of any one of (31) to (35) above.

(38) A method of inducing immune response to human papillomavirus, comprising administering to a mammal the composition of (33) or (34) above.

(39) A method of preventing and/or treating infections with human papillomavirus, comprising administering to a mammal the composition of any one of (33) to (35) above.

In another aspect of the present invention, a summary of the present invention is described as below.

(1-1) A lipid particle encapsulating a nucleic acid molecule capable of expressing the E6 and E7 antigens of human papillomavirus, wherein the lipid comprises a cationic lipid represented by general formula (Ia) or a pharmaceutically acceptable salt thereof:

[Formula 5]

(Ia)

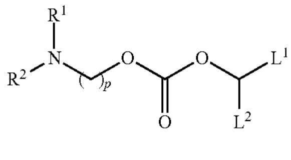

wherein $R^1$ and $R^2$ each independently represent a $C_1$-$C_3$ alkyl group;

$L^1$ represents a $C_{17}$-$C_{19}$ alkenyl group which may have one or a plurality of $C_2$-$C_4$ alkanoyloxy groups;

$L^2$ represents a $C_{10}$-$C_{19}$ alkyl group which may have one or a plurality of $C_2$-$C_4$ alkanoyloxy groups or a $C_{10}$-$C_{19}$ alkenyl group which may have one or a plurality of $C_2$-$C_4$ alkanoyloxy groups; and p is 3 or 4.

(1-2) The particle of (1-1) above, wherein both $R^1$ and $R^2$ in general formula (Ia) are a methyl group.

(1-3) The particle of (1-1) or (1-2) above, wherein p in general formula (Ia) is 3.

(1-4) The particle of any one of (1-1) to (1-3) above, wherein $L^1$ in general formula (Ia) is a $C_{17}$-$C_{19}$ alkenyl group which may have one or a plurality of acetoxy groups.

(1-5) The particle of any one of (1-1) to (1-4) above, wherein $L^2$ in general formula (Ia) is a $C_{10}$-$C_{12}$ alkyl group which may have one or a plurality of acetoxy groups or a $C_{10}$-$C_{19}$ alkenyl group which may have one or a plurality of acetoxy groups.

(1-6) The particle of any one of (1-1) to (1-4) above, wherein $L^2$ in general formula (Ta) is a $C_{10}$-$C_{12}$ alkyl group which may have one or a plurality of acetoxy groups or a $C_{17}$-$C_{19}$ alkenyl group which may have one or a plurality of acetoxy groups.

(1-7) The particle of any one of (1-1) to (1-6) above, wherein $L^1$ in general formula (Ta) is an (R)-11-acetyloxy-cis-8-heptadecenyl group, a cis-8-heptadecenyl group or a (8Z,11Z)-heptadecadienyl group.

(1-8) The particle of any one of (1-1) to (1-7) above, wherein $L^2$ in general formula (Ta) is a decyl group, a cis-7-decenyl group, a dodecyl group or an (R)-11-acetyloxy-cis-8-heptadecenyl group.

(1-9) The particle of (1-1), wherein the cationic lipid is represented by the following structural formula:

[Formula 6]

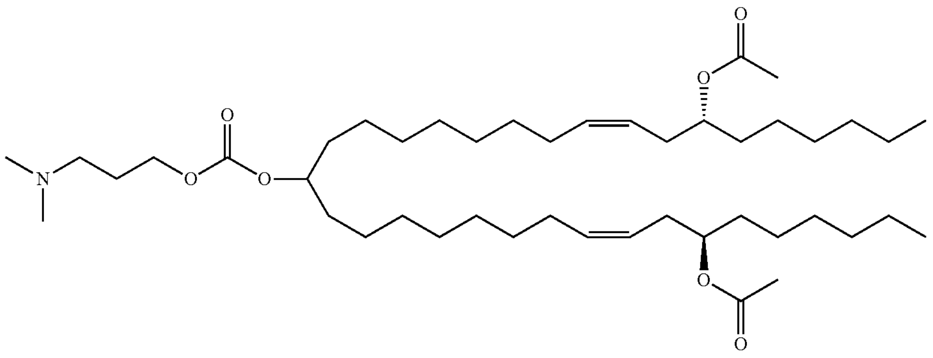

(1-10) The particle of (1-1), wherein the cationic lipid is represented by the following structural formula:

[Formula 7]

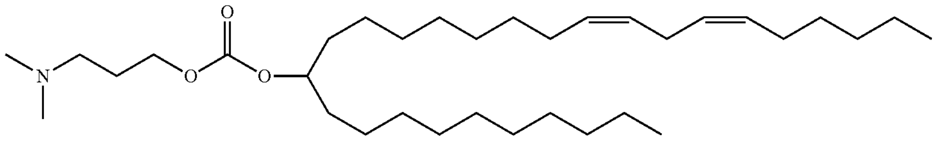

(1-11) The particle of (1-1), wherein the cationic lipid is represented by the following structural formula:

[Formula 8]

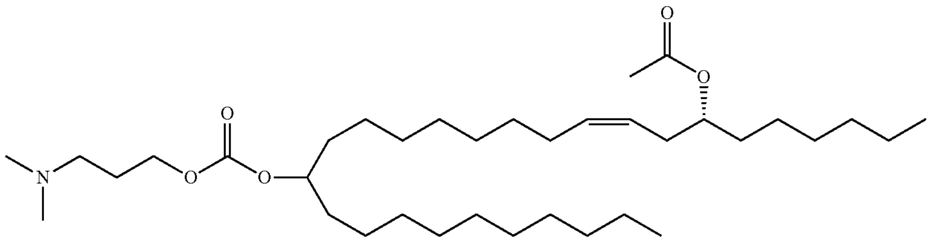

(1-12) The particle of (1-9) or (1-10) above, wherein the lipid further comprises amphipathic lipids, sterols and PEG lipids.

(1-13) The particle of (1-11) above, wherein the lipid further comprises amphipathic lipids, sterols and PEG lipids.

(1-14) The particle of (1-12) above, wherein the amphipathic lipid is at least one selected from the group consisting of distearoyl phosphatidylcholine, dioleoyl phosphatidylcholine and dioleoyl phosphatidylethanolamine.

(1-15) The particle of (1-13) above, wherein the amphipathic lipid is at least one selected from the group consisting of distearoyl phosphatidylcholine, dioleoyl phosphatidylcholine and dioleoyl phosphatidylethanolamine.

(1-16) The particle of (1-12) or (1-14) above, wherein the sterol is cholesterol.

(1-17) The particle of (1-13) or (1-15) above, wherein the sterol is cholesterol.

(1-18) The particle of any one of (1-12), (1-14) or (1-16) above, wherein the PEG lipid is 1,2-dimyristoyl-sn-glycerol methoxypolyethylene glycol and/or N-[methoxy poly(ethyleneglycol) carbamoyl]-1,2-dimyristyloxypropyl-3-amine.

(1-19) The particle of any on e of (1-13), (1-15) or (1-17) above, wherein the PEG lipid is 1,2-dimyristoyl-sn-glycerol methoxypolyethylene glycol and/or N-[methoxy poly(ethyleneglycol) carbamoyl]-1,2-dimyristyloxypropyl-3-amine.

(1-20) The particle of any one of (1-12) to (1-19) above, wherein the lipid composition of the amphipathic lipid, the sterol, the cationic lipid and the PEG lipid is 22.5% or less of the amphipathic lipid, 15 to 55% of the sterol, 40 to 65% of the cationic lipid and 1 to 5% of the PEG lipid in terms of molar quantity; and the ratio of the total lipid weight to the weight of nucleic acid is 15 to 30.

(1-21) The particle of (1-20) above, wherein the amphipathic lipid amounts to 5 to 22.5%.

(1-22) The particle of (1-21) above, wherein the amphipathic lipid amounts to 10 to 22.5%

(1-23) The particle of any one of (1-20) to (1-22) above, wherein the PEG lipid amounts to 1 to 3%.

(1-24) The particle of (1-23) above, wherein the PEG lipid amounts to 1 to 2%.

(1-25) The particle of any one of (1-12), (1-14), (1-16) or (1-18) above, wherein the lipid composition of the amphipathic lipid, the sterol, the cationic lipid and the PEG lipid is 5 to 15% of the amphipathic lipid, 35 to 50% of the sterol, 40 to 55% of the cationic lipid and 1 to 3% of the PEG lipid in terms of molar quantity; and the ratio of the total lipid weight to the weight of nucleic acid is 15 to 30.

(1-26) The particle of (1-25) above, wherein the amphipathic lipid amounts to 10 to 15%; the sterol amounts to 35 to 45%; the cationic lipid amounts to 40 to 50%; and the PEG lipid amounts to 1 to 2%.

(1-27) The particle of (1-26) above, wherein the amphipathic lipid amounts to 10 to 15%; the sterol amounts to 35 to 45%; the cationic lipid amounts to 45 to 50%; and the PEG lipid amounts to 1.5 to 2%.

(1-28) The particle of any one of (1-13), (1-15), (1-17) or (1-19) above, wherein the lipid composition of the amphipathic lipid, the sterol, the cationic lipid and the PEG lipid is 15 to 22.5% of the amphipathic lipid, 15 to 40% of the sterol, 40 to 60% of the cationic lipid and 1 to 3% of the PEG lipid in terms of molar quantity; and the ratio of the total lipid weight to the weight of nucleic acid is 15 to 30.

(1-29) The particle of (1-28) above, wherein the cationic lipid amounts to 45 to 60% and the PEG lipid amounts to 1 to 2%.

(1-30) The particle of (1-29) above, wherein the amphipathic lipid amounts to 17.5 to 22.5%.

(1-31) The particle of any one of (1-20) to (1-30) above, wherein the ratio of the total lipid weight to the weight of nucleic acid is 15 to 25.

(1-32) The particle of (1-31) above, wherein the ratio of the total lipid weight to the weight of nucleic acid is 15 to 22.5.

(1-33) The particle of (1-32) above, wherein the ratio of the total lipid weight to the weight of nucleic acid is 17.5 to 22.5.

(1-34) The particle of any one of (1-1) to (1-33) above, wherein the human papillomavirus is HPV16.

(1-35) The particle of (1-34) above, wherein the human papillomavirus is HPV16 and the E6 antigen thereof consists of an amino acid sequence having at least 95% identity with the amino acid sequence as shown in SEQ ID NO: 8.

(1-36) The particle of (1-34) or (1-35) above, wherein the human papillomavirus is HPV16 and the E7 antigen thereof consists of an amino acid sequence having at least 95% identity with the amino acid sequence as shown in SEQ ID NO: 9.

(1-37) The particle of any one of (1-34) to (1-36) above, wherein the human papillomavirus is HPV16 and the nucleic acid molecule capable of expressing the E6 and E7 antigens of human papillomavirus encodes an HPV16 E6/E7 fusion protein consisting of an amino acid sequence having at least 95% identity with the amino acid sequence as shown in SEQ ID NO: 17.

(1-38) The particle of any one of (1-34) to (1-37) above, wherein the human papillomavirus is HPV16 and the nucleic acid molecule capable of expressing the E6 and E7 antigens of HPV16 is an mRNA molecule comprising a cap structure (Cap), 5' untranslated region (5'-UTR), a leader sequence, E6 coding region, a protease cleavage sequence (furin cleavage site), E7 coding region, 3' untranslated region (3'-UTR) and a polyA tail (polyA).

(1-39) The particle of (1-38) above, wherein the sequence of the nucleic acid molecule capable of expressing the E6 and E7 antigens of HPV16 consists of a nucleotide sequence having at least 90% identity with any one of the sequences as shown in SEQ ID NOS: 2, 4 or 6.

(1-40) The particle of any one of (1-1) to (1-33) above, wherein the human papillomavirus is HPV18.

(1-41) The particle of (1-40) above, wherein the human papillomavirus is HPV18 and the E6 antigen thereof consists of an amino acid sequence having at least 95% identity with the amino acid sequence as shown in SEQ ID NO: 14.

(1-42) The particle of (1-40) or (1-41) above, wherein the human papillomavirus is HPV18 and the E7 antigen thereof consists of an amino acid sequence having at least 95% identity with the amino acid sequence as shown in SEQ ID NO: 15.

(1-43) The particle of any one of (1-40) to (1-42) above, wherein the human papillomavirus is HPV18 and the nucleic acid molecule capable of expressing the E6 and E7 antigens of human papillomavirus encodes an HPV18 E6/E7 fusion protein consisting of an amino acid sequence having 95% or more identity with the sequence as shown in SEQ ID NO: 18.

(1-44) The particle of any one of (1-40) to (1-43) above, wherein the human papillomavirus is HPV18 and the nucleic acid molecule capable of expressing the E6 and E7 antigens of HPV18 is an mRNA molecule comprising a cap structure (Cap), 5' untranslated region (5'-UTR), a leader sequence, E6 coding region, a protease cleavage sequence (furin cleavage site), E7 coding region, 3' untranslated region (3'-UTR) and a polyA tail (polyA).

(1-45) The particle of (1-44) above, wherein the sequence of the nucleic acid molecule capable of expressing the E6 and E7 antigens of HPV18 consists of a nucleotide sequence having at least 90% identity with the sequence as shown in SEQ ID NO: 11 or 13.

(1-46) The particle of any one of (1-1) to (1-45) above, wherein the nucleic acid molecule comprises at least one modified nucleotide.

(1-47) The particle of (1-46) above, wherein the modified nucleotide comprises at least one of 5-substituted pyrimidine nucleotide and/or pseudouridine optionally substituted at position 1.

(1-48) The particle of (1-46) above, wherein the modified nucleotide comprises at least one selected from the group consisting of 5-methylcytidine, 5-methoxyuridine, 5-methyluridine, pseudouridine and 1-alkylpseudouridine.

(1-49) The particle of (1-46) above, wherein the modified nucleotide comprises at least one selected from the group consisting of 5-methylcytidine, 5-methyluridine and 1-methylpseudouridine.

(1-50) The particle of any one of (1-1) to (1-49) above, wherein the mean particle size is 30 nm to 300 nm.

(1-51) Use of the particle of any one of (1-1) to (1-50) above for manufacturing a composition for preventing and/or treating infections with human papillomavirus.

(1-52) The use of (1-51) above, wherein the infections are infections with HPV16 or HPV18.

(1-53) A composition comprising the particle of any one of (1-1) to (1-50) above.

(1-54) The composition of (1-53) above for allowing the expression of the E6 and E7 antigens of human papillomavirus in vivo or in vitro.

(1-55) The composition of (1-53) or (1-54) above for use as a pharmaceutical drug.

(1-56) The composition of (1-55) above for inducing immune response to human papillomavirus.

(1-57) The composition of (1-55) or (1-56) above for preventing and/or treating infections with human papillomavirus.

(1-58) A method of expressing the E6 and E7 antigens of human papillomavirus in vitro, comprising introducing into cells the composition of (1-53) or (1-54) above.

(1-59) A method of expressing the E6 and E7 antigens of human papillomavirus in vivo, comprising administering to a mammal the composition of any one of (1-53) to (1-57) above.

(1-60) A method of inducing immune response to human papillomavirus, comprising administering to a mammal the composition of (1-55) or (1-56) above.

(1-61) A method of preventing and/or treating infections with human papillomavirus, comprising administering to a mammal the composition of any one of (1-55) to (1-57) above.

Effect of the Invention

According to the present invention, it becomes possible to prevent and/or treat infections with human papillomavirus. According to the present invention, it also becomes possible to prevent and/or treat diseases caused by infections with human papillomavirus (e.g., cervical cancer, cervical dysplasia, and the like). Further, the particle of the present invention has excellent property in terms of metabolic stability, in vitro activity, in vivo activity, rapidness in expression of drug efficacy, persistence of drug efficacy, physical stability, drug interaction, safety and so on, and is useful as a pharmaceutical drug for treating or preventing the above-mentioned diseases.

The present specification encompasses the contents disclosed in the specification and/or the drawings of Japanese Patent Application No. 2019-207001 based on which the present patent application claims priority.

BEST MODES FOR CARRYING OUT THE INVENTION

Figure 1:
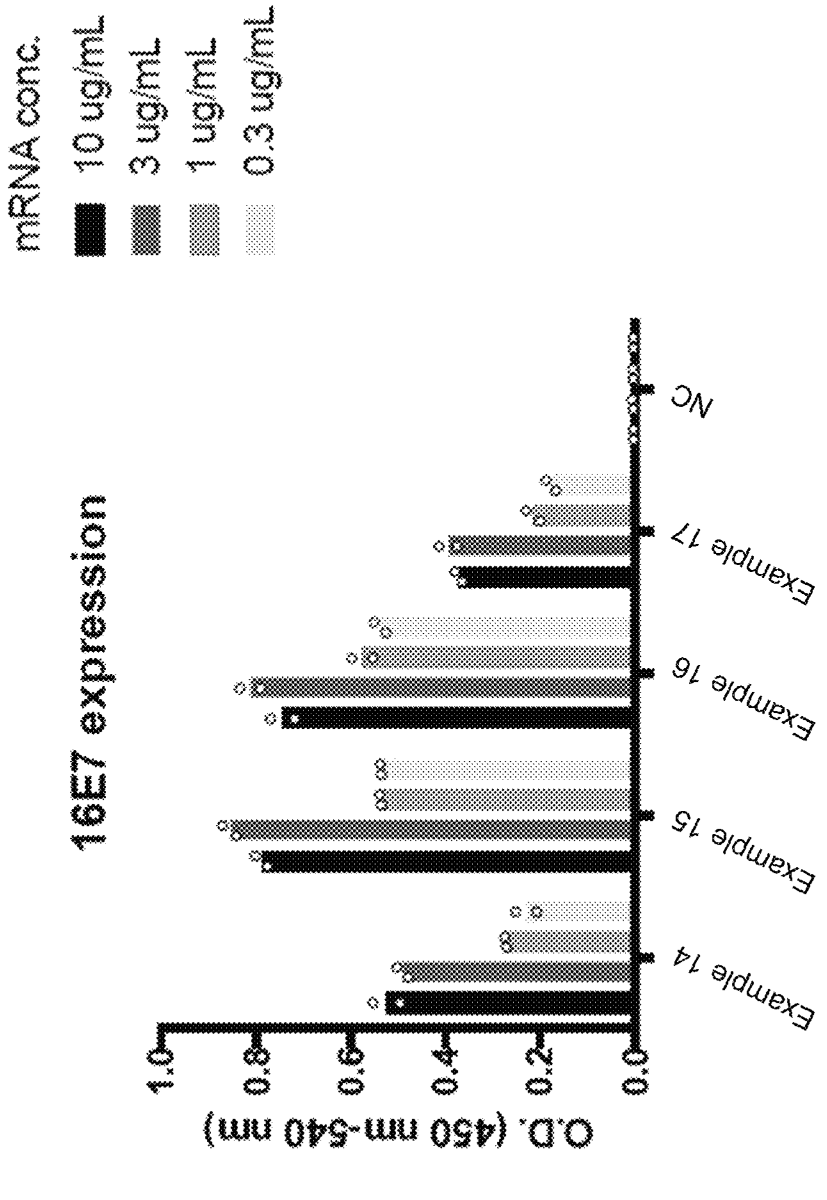
FIG. 1 Expression levels of HPV16 E7 protein from HEK293T cells transfected with nucleic acid lipid particles encapsulating mRNA. Examples 4-17: nucleic acid lipid particles encapsulating mRNA. NC: untreated negative control. Tests were carried out in duplicate. Bars indicate the averages and circle symbols do individual data.

Hereinbelow, embodiments of the present invention will be described in detail.

The present invention provides lipid particles encapsulating a nucleic acid molecule capable of expressing the E6 and E7 antigens of human papillomavirus, wherein the lipid comprises a cationic lipid represented by general formula (Ia) or a pharmaceutically acceptable salt thereof:

[Formula 9]

(Ia)

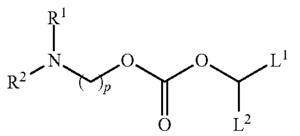

wherein $R^1$ and $R^2$ each independently represent a $C_1$-$C_3$ alkyl group;

$L^1$ represents a $C_{17}$-$C_{19}$ alkenyl group which may have one or a plurality of $C_2$-$C_4$ alkanoyloxy groups;

$L^2$ represents a $C_{10}$-$C_{19}$ alkyl group which may have one or a plurality of $C_2$-$C_4$ alkanoyloxy groups or a $C_{10}$-$C_{19}$ alkenyl group which may have one or a plurality of $C_2$-$C_4$ alkanoyloxy groups; and p is 3 or 4.

$R^1$ and $R^2$ in general formula (Ia) each independently represent a $C_1$-$C_3$ alkyl group. Preferably, both $R^1$ and $R^2$ are a methyl group.

p in general formula (Ia) is 3 or 4, preferably 3.

$L^1$ in general formula (Ia) represents a $C_{17}$-$C_{19}$ alkenyl group which may have one or a plurality of $C_2$-$C_4$ alkanoyloxy groups. Preferably, $L^1$ is a $C_{17}$-$C_{19}$ alkenyl group which may have one or a plurality of acetoxy groups. Specific examples of $L^1$ include, but are not limited to, (R)-11-acetyloxy-cis-8-heptadecenyl group, cis-8-heptadecenyl group and (8Z,11Z)-heptadecadienyl group.

$L^2$ in general formula (Ta) represents a $C_{10}$-$C_{19}$ alkyl group which may have one or a plurality of $C_2$-$C_4$ alkanoyloxy groups, or a $C_{10}$-$C_{19}$ alkenyl group which may have one or a plurality of $C_2$-$C_4$ alkanoyloxy groups. Preferably, $L^2$ is a $C_{10}$-$C_{12}$ alkyl group which may have one or a plurality of acetoxy groups, or a $C_{10}$-$C_{19}$ alkenyl group which may have one or a plurality of acetoxy groups. Alternatively, it is also preferable that $L^2$ in general formula (Ta) is a $C_{10}$-$C_{12}$ alkyl group which may have one or a plurality of acetoxy groups, or a $C_{17}$-$C_{19}$ alkenyl group which may have one or a plurality of acetoxy groups. Specific examples of $L^2$ include, but are not limited to, decyl group, cis-7-decenyl group, dodecyl group and (R)-11-acetyloxy-cis-8-heptadecenyl group.

With respect to cationic lipid (a component which constitutes the particle of the present invention), the following lipids may be enumerated as specific examples: (7R,9Z,26Z,29R)-18-({[3-(dimethylamino)propoxy]carbonyl}oxy)pentatriaconta-9,26-diene-7,29-diyl diacetate, 3-dimethylaminopropyl(9Z,12Z)-octacosa-19,22-dien-11-yl carbonate, and (7R,9Z)-18-({[3-(dimethylamino)propyloxy]carbonyl}oxy)octacosa-9-en-7-yl acetate, which are represented by the following structural formulas, respectively:

[Formula 10]

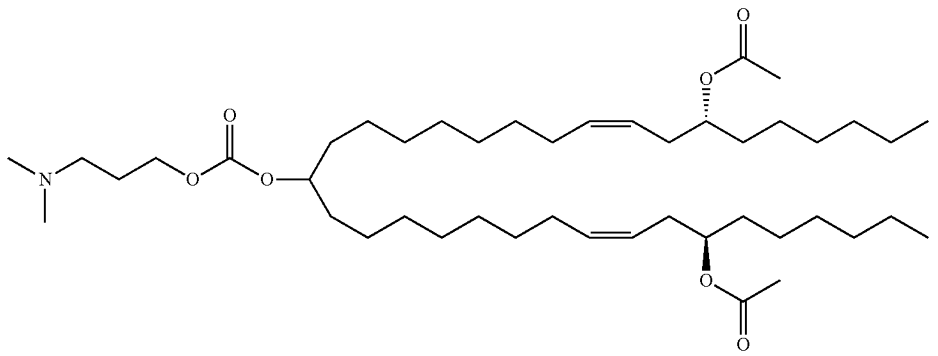

[Formula 11]

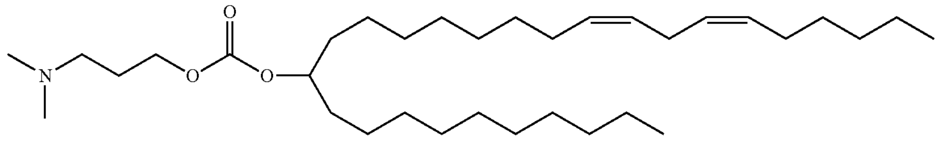

[Formula 12]

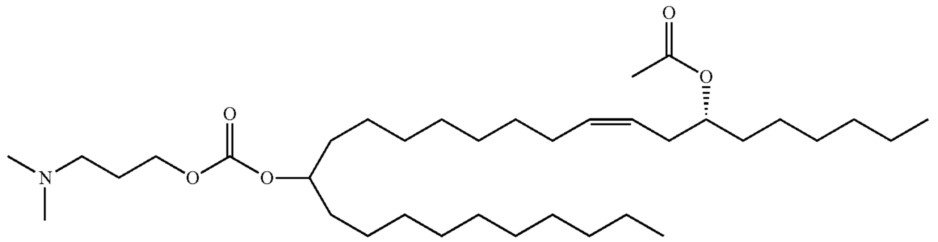

The cationic lipid represented by general formula (Ia) may be either a single compound or a combination of two or more compounds.

A method for preparing the cationic lipid represented by general formula (Ia) is disclosed in International Publication WO 2015/005253.

The lipid of the present invention may further comprise amphipathic lipids, sterols and PEG lipids.

The amphipathic lipid is a lipid which has affinity to both polar and non-polar solvents. Specific examples of the amphipathic lipid include, but are not limited to, distearoyl phosphatidylcholine, dioleoyl phosphatidylcholine, dioleoyl phosphatidylethanolamine and combinations thereof. As amphipathic lipid to be used in the particle of the present invention, distearoyl phosphatidylcholine and/or dioleoyl phosphatidylethanolamine is preferable. More preferable is distearoyl phosphatidylcholine.

The sterol is a sterol which has a hydroxy group. Specific examples of the sterol include, but are not limited to, cholesterol.

The PEG lipid is a lipid modified with PEG. Specific examples of the PEG lipid include, but are not limited to, 1,2-dimyristoyl-sn-glycerol methoxypolyethylene glycol and/or N-[methoxy poly(ethyleneglycol) 2000]carbamoyl]-1,2-dimyristyloxypropyl-3-amine, or a combination thereof. Preferably, 1,2-dimyristoyl-sn-glycerol methoxypolyethylene glycol is used.

The lipid composition of the amphipathic lipid, the sterol, the cationic lipid and the PEG lipid is not particularly limited. Preferably, the lipid composition of the amphipathic lipid, the sterol, the cationic lipid and the PEG lipid is 22.5% or less of the amphipathic lipid, 15 to 55% of the sterol, 40 to 65% of the cationic lipid and 1 to 5% of the PEG lipid in terms of molar quantity; and the ratio of the total lipid weight to the weight of nucleic acid is 15 to 30. More preferably, the lipid composition of the amphipathic lipid, the sterol, the cationic lipid and the PEG lipid is 5 to 22.5% of the amphipathic lipid, 15 to 55% of the sterol, 40 to 65% of the cationic lipid and 1 to 5% of the PEG lipid in terms of molar quantity; and the ratio of the total lipid weight to the weight of nucleic acid is 15 to 30. Still more preferably, the lipid composition of the amphipathic lipid, the sterol, the cationic lipid and the PEG lipid is 10 to 22.5% of the amphipathic lipid, 15 to 55% of the sterol, 40 to 65% of the cationic lipid and 1 to 5% of the PEG lipid in terms of molar quantity; and the ratio of the total lipid weight to the weight of nucleic acid is 15 to 30. In the above-described lipid composition, the PEG lipid more preferably amounts to 1 to 3%, still more preferably 1 to 2%, and especially preferably 1.5 to 2%, in terms of molar quantity. Further, in the above-described lipid composition, the ratio of the total lipid weight to the weight of nucleic acid is more preferably 15 to 25, still more preferably 15 to 22.5, and especially preferably 17.5 to 22.5.

When 3-dimethylaminopropyl(9Z,12Z)-octacosa-19,22-dien-11-yl carbonate or (7R,9Z,26Z,29R)-18-({[3-(dimethylamino)propoxy]carbonyl}oxy)pentatriaconta-9,26-diene-7,29-diyl diacetate is used as the cationic lipid, the lipid composition of the amphipathic lipid, the sterol, the cationic lipid and the PEG lipid is not particularly limited. Preferably, the lipid composition of the amphipathic lipid, the sterol, the cationic lipid and the PEG lipid is 15% or less of the amphipathic lipid, 20 to 55% of the sterol, 40 to 65% of the cationic lipid and 1 to 5% of the PEG lipid in terms of molar quantity. More preferably, the lipid composition of the amphipathic lipid, the sterol, the cationic lipid and the PEG lipid is 5 to 15% of the amphipathic lipid, 35 to 50% of the sterol, 40 to 55% of the cationic lipid and 1 to 3% of the PEG lipid in terms of molar quantity. Still more preferably, the lipid composition of the amphipathic lipid, the sterol, the cationic lipid and the PEG lipid is 10 to 15% of the amphipathic lipid, 35 to 45% of the sterol, 40 to 50% of the cationic lipid and 1 to 2% of the PEG lipid in terms of molar quantity. Further still more preferably, the lipid composition of the amphipathic lipid, the sterol, the cationic lipid and the PEG lipid is 10 to 15% of the amphipathic lipid, 35 to 45% of the sterol, 45 to 50% of the cationic lipid and 1.5 to 2% of the PEG lipid in terms of molar quantity. Especially preferably, the lipid composition of the amphipathic lipid, the sterol, the cationic lipid and the PEG lipid is 12.5% of the amphipathic lipid, 41% of the sterol, 45% of the cationic lipid and 1.5% of the PEG lipid in terms of molar quantity. In the above-described lipid composition, the ratio of the total lipid weight to the weight of nucleic acid is preferably 15 to 30, more preferably 15 to 25, still more preferably 15 to 22.5, and especially preferably 17.5 to 22.5.

When (7R,9Z)-18-({[3-(dimethylamino)propyloxy]carbonyl}oxy)octacosa-9-en-7-yl acetate is used as the cationic lipid, the lipid composition of the amphipathic lipid, the sterol, the cationic lipid and the PEG lipid is not particularly limited. Preferably, the lipid composition of the amphipathic lipid, the sterol, the cationic lipid and the PEG lipid is 12.5 to 22.5% of the amphipathic lipid, 15 to 45% of the sterol, 40 to 65% of the cationic lipid and 1 to 5% of the PEG lipid in terms of molar quantity. More preferably, the lipid composition of the amphipathic lipid, the sterol, the cationic lipid and the PEG lipid is 15 to 22.5% of the amphipathic lipid, 15 to 40% of the sterol, 40 to 60% of the cationic lipid and 1 to 3% of the PEG lipid in terms of molar quantity. Still more preferably, the lipid composition of the amphipathic lipid, the sterol, the cationic lipid and the PEG lipid is 15 to 22.5% of the amphipathic lipid, 15 to 40% of the sterol, 45 to 60% of the cationic lipid and 1 to 2% of the PEG lipid in terms of molar quantity. Further still more preferably, the lipid composition of the amphipathic lipid, the sterol, the cationic lipid and the PEG lipid is 17.5 to 22.5% of the amphipathic lipid, 15 to 40% of the sterol, 45 to 60% of the cationic lipid and 1 to 2% of the PEG lipid in terms of molar quantity. In the above-described lipid composition, the ratio of the total lipid weight to the weight of nucleic acid is preferably 15 to 30, more preferably 15 to 25, still more preferably 15 to 22.5, and especially preferably 17.5 to 22.5.

As regards specific combinations of lipids in the present invention, distearoyl phosphatidylcholine, dioleoyl phosphatidylcholine or dioleoyl phosphatidylethanolamine as the amphipathic lipid; cholesterol as the sterol; (7R,9Z,26Z,29R)-18-({[3-(dimethylamino)propoxy]carbonyl}oxy)pentatriaconta-9,26-diene-7,29-diyl diacetate, 3-dimethylaminopropyl(9Z,12Z)-octacosa-19,22-dien-11-yl carbonate, or (7R,9Z)-18-({[3-(dimethylamino)propyloxy]carbonyl}oxy)octacosa-9-en-7-yl acetate as the cationic lipid; and 1,2-dimyristoyl-sn-glycerol methoxypolyethylene glycol or N-[methoxy poly(ethyleneglycol) carbamoyl]-1,2-dimyristyloxypropyl-3-amine as the PEG lipid; may be used in combination.

The following combination is preferably used: distearoyl phosphatidylcholine or dioleoyl phosphatidylethanolamine as the amphipathic lipid; cholesterol as the sterol; (7R,9Z,26Z,29R)-18-({[3-(dimethylamino)propoxy]carbonyl}oxy)pentatriaconta-9,26-diene-7,29-diyl diacetate or (7R,9Z)-18-({[3-(dimethylamino)propyloxy]carbonyl}oxy)octacosa-9-en-7-yl acetate as the cationic lipid; and 1,2-dimyristoyl-sn-glycerol methoxypolyethylene glycol as the PEG lipid. More preferably, the following combination of lipids is used in the present invention: distearoyl phosphatidylcholine as the amphipathic lipid; cholesterol as the sterol; (7R,9Z,26Z,29R)-18-({[3-(dimethylamino)propoxy]carbonyl}oxy)pentatriaconta-9,26-diene-7,29-diyl diacetate or (7R,9Z)-18-({[3-(dimethylamino)propyloxy]carbonyl}oxy)octacosa-9-en-7-yl acetate as the cationic lipid; and 1,2-dimyristoyl-sn-glycerol methoxypolyethylene glycol as the PEG lipid.

The nucleic acid molecule to be encapsulated in the lipid particle in the present invention is one capable of expressing the E6 and E7 antigens of human papillomavirus. The E6 and E7 antigens of human papillomavirus to be expressed by the nucleic acid molecule encapsulated in lipid particles may be a fusion protein of the E6 and E7 antigens, and a protease cleavage sequence may be contained between the E6 and E7 antigens. The genotype of human papillomavirus is not particularly limited. HPV16, 18, 31, 33, 35, 39, 45, 51, 52, 56, 58, 59 and 68 may be enumerated, for example. It has been demonstrated that HPV16, 18, 31, 33, 35, 39, 45, 51, 52, 56, 58, 59 and 68 are associated with cancer development represented by cervical cancer.

The amino acid sequence of the E6 antigen of HPV16 is shown in SEQ ID NO: 8. The nucleic acid molecule to be encapsulated in the lipid particle may be one that encodes an E6 antigen of HPV16 consisting of an amino acid sequence having at least 95%, preferably 96% and more preferably 97% identity with the amino acid sequence as shown in SEQ ID NO: 8.

The amino acid sequence of the E7 antigen of HPV16 is shown in SEQ ID NO: 9. The nucleic acid molecule to be encapsulated in the lipid particle may be one that encodes an E7 antigen of HPV16 consisting of an amino acid sequence having at least 95%, preferably 96% and more preferably 97% identity with the amino acid sequence as shown in SEQ ID NO: 9.

The amino acid sequence of the E6 antigen of HPV18 is shown in SEQ ID NO: 14. The nucleic acid molecule to be encapsulated in the lipid particle may be one that encodes an E6 antigen of HPV18 consisting of an amino acid sequence having at least 95%, preferably 96% and more preferably 97% identity with the amino acid sequence as shown in SEQ ID NO: 14.

The amino acid sequence of the E7 antigen of HPV18 is shown in SEQ ID NO: 15. The nucleic acid molecule to be encapsulated in the lipid particle may be one that encodes an E7 antigen of HPV18 consisting of an amino acid sequence having at least 95%, preferably 96% and more preferably 97% identity with the amino acid sequence as shown in SEQ ID NO: 15.

The amino acid sequence of a protease cleavage sequence (furin cleavage site) is shown in SEQ ID NO: 16. As regards protease cleavage sequence, any sequence may be used as long as it is cleaved by furin protein. Specific examples of protease cleavage sequence include, but are not limited to, a sequence represented by R-X-K/R-R (wherein R is arginine, K is lysine, and X is any amino acid) (J. Biol. Chem. 1992, 267, 16396; J. Biol. Chem. 1991, 266, 12127).

The amino acid sequence of a fusion protein of the E6/E7 antigens of HPV16 is shown in SEQ ID NO: 17. The nucleic acid molecule to be encapsulated in the lipid particle may be one that encodes a fusion protein of the E6/E7 antigens of HPV16 consisting of an amino acid sequence having at least 95%, preferably 96% and more preferably 97% identity with the amino acid sequence as shown in SEQ ID NO: 17.

The amino acid sequence of a fusion protein of the E6/E7 antigens of HPV18 is shown in SEQ ID NO: 18. The nucleic acid molecule to be encapsulated in the lipid particle may be one that encodes a fusion protein of the E6/E7 antigens of HPV18 consisting of an amino acid sequence having at least 95%, preferably 96% and more preferably 97% identity with the amino acid sequence as shown in SEQ ID NO: 18.

The term "identity of amino acid sequence" refers to the rate of identical amino acid residues over full length sequence expressed in a numerical form, when the exactly matching amino acid residues at the corresponding position are taken as identical. The identity of amino acid sequence in the present invention is calculated with a sequence analysis software GENETYX-SV/RC (Genetyx Corporation). This algorism is commonly used in the art. The amino acid encoded by the nucleic acid molecule encapsulated in the particle of the present invention may have mutations (substitutions), deletions, insertions and/or additions of amino acids, as long as the encoded amino acid retains at least a certain degree of identity with SEQ ID NOS: 8, 9 and 14-18.

The amino acid encoded by the nucleic acid molecule encapsulated in the particle of the present invention retains the sequence identity as described above and may yet have substitutions, deletions, insertions and/or additions of several amino acids (preferably 10 or less, more preferably 7 or less, still more preferably 5, 4, 3, 2 or 1) per position at several positions (preferably 5 or less, more preferably 3, 2 or 1) in the amino acid sequences as shown in SEQ ID NOS: 8, 9 and 14-18.

The nucleic acid molecule capable of expressing the E6 and E7 antigens of human papillomavirus (e.g., HPV16 or HPV18) may be an mRNA molecule comprising a cap structure (Cap), 5' untranslated region (5'-UTR), a leader sequence, E6 coding region, a protease cleavage sequence (furin cleavage site), E7 coding region, 3' untranslated region (3'-UTR) and a polyA tail (polyA). A cap structure (Cap) is found at the 5' end of mRNA of many eukaryotes. This is a moiety having a 7-methylguanosine structure. Specific examples of the cap structure include, but are not limited to, cap0, cap1, cap2 and ARCA (Anti-Reverse Cap Analog), which are represented by the following structural formulas.

[Formula 13]

Cap 0

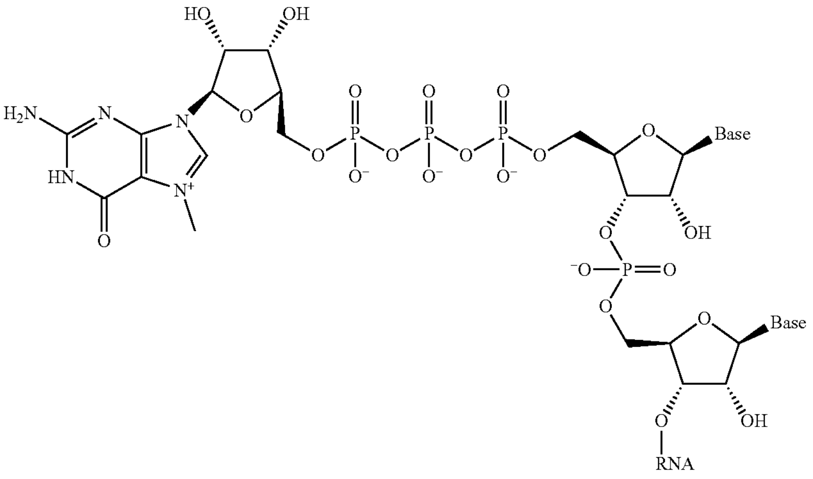

(wherein Base represents any nucleobase, either unmodified or modified; and RNA represents any polynucleotide.)

[Formula 14]

Cap 1

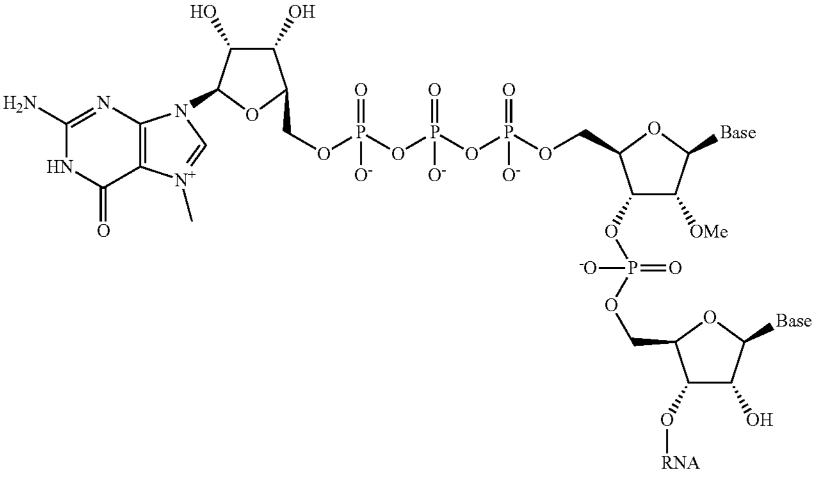

-continued

[Formula 15]

Cap 2

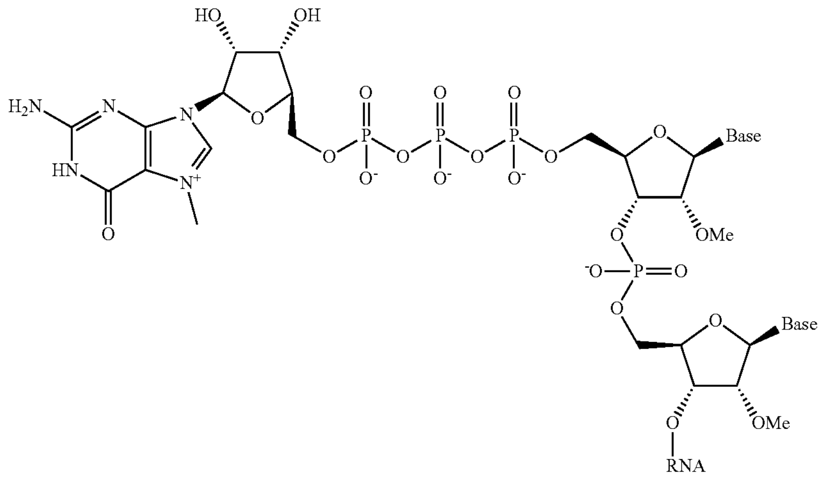

[Formula 16]

ARCA

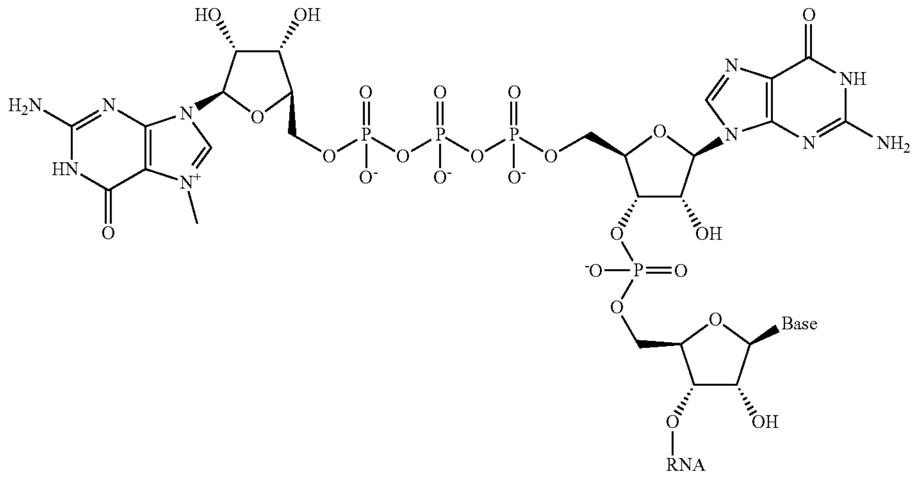

As a cap structure of the mRNA of the present invention, cap0 or cap1 is preferable, with cap1 being more preferable. Specific examples of the sequence of 5' untranslated region (5'-UTR) include, but are not limited to, a sequence represented by nucleotide numbers 2 to 70 in SEQ ID NO: 2, a sequence represented by nucleotide numbers 2 to 70 in SEQ ID NO: 4; and a sequence represented by nucleotide numbers 2 to 70 in SEQ ID NO: 6, a sequence represented by nucleotide numbers 2 to 70 in SEQ ID NO: 11, a sequence represented by nucleotide numbers 2 to 70 in SEQ ID NO: 13. Specific examples of the leader sequence include, but are not limited to, a sequence represented by nucleotide numbers 71 to 124 in SEQ ID NO: 2, a sequence represented by nucleotide numbers 71 to 124 in SEQ ID NO: 4; and a sequence represented by nucleotide numbers 71 to 124 in SEQ ID NO: 6, a sequence represented by nucleotide numbers 71 to 124 in SEQ ID NO: 11, a sequence represented by nucleotide numbers 71 to 124 in SEQ ID NO: 13. The sequence of E6 coding region is a sequence capable of expressing the whole or part of the amino acid sequence of E6 antigen and may comprise a start codon and/or a stop codon. Specific examples of the sequence of E6 coding region include, but are not limited to, a sequence represented by nucleotide numbers 125 to 574 in SEQ ID NO: 2, a sequence represented by nucleotide numbers 125 to 574 in SEQ ID NO: 4; and a sequence represented by nucleotide numbers 125 to 574 in SEQ ID NO: 6, a sequence represented by nucleotide numbers 125 to 589 in SEQ ID NO: 11, a sequence represented by nucleotide numbers 125 to 589 in SEQ ID NO: 13. Specific examples of the protease cleavage sequence (furin cleavage site) include, but are not limited to, a sequence represented by nucleotide numbers 575 to 595 in SEQ ID NO: 2, a sequence represented by nucleotide numbers 575 to 595 in SEQ ID NO: 4; and a sequence represented by nucleotide numbers 575 to 595 in SEQ ID NO: 6, a sequence represented by nucleotide numbers 590 to 610 in SEQ ID NO: 11, a sequence represented by nucleotide numbers 590 to 610 in SEQ ID NO: 13. The sequence of E7 coding region is a sequence capable of expressing the whole or part of the amino acid sequence of E7 antigen and may comprise a start codon and/or a stop codon. Specific examples of the sequence of E7 coding region include, but are not limited to, a sequence represented by nucleotide numbers 596 to 889 in SEQ ID NO: 2, a sequence represented by nucleotide numbers 596 to 889 in SEQ ID NO: 4; and a sequence represented by nucleotide numbers 596 to 889 in SEQ ID NO: 6, a sequence represented by nucleotide numbers 611 to 925 in SEQ ID NO: 11, a sequence represented by nucleotide numbers 611 to 925 in SEQ ID NO: 13. Specific examples of the sequence of 3' untranslated region (3'-UTR) include, but are not limited to, a sequence represented by nucleotide numbers 890 to 1021 in SEQ ID NO: 2, a sequence represented by nucleotide numbers 890 to 1021 in SEQ ID NO: 4; and a sequence represented by nucleotide numbers 890 to 1021 in SEQ ID NO: 6, a sequence represented by nucleotide numbers 926 to 1057 in SEQ ID NO: 11, a sequence represented by nucleotide numbers 926 to 1057 in SEQ ID NO: 13. Specific examples of the sequence of polyA tail (polyA) include, but are not limited to, a sequence represented by nucleotide numbers 1022 to 1123 in SEQ ID NO: 2, a sequence represented by nucleotide numbers 1022 to 1123 in SEQ ID NO: 4; and a sequence represented by nucleotide numbers 1022 to 1123 in SEQ ID NO: 6, a sequence represented by nucleotide numbers 1058 to 1159 in SEQ ID NO: 11, a sequence represented by nucleotide numbers 1058 to 1159 in SEQ ID NO: 13. Sequences of the cap structure (Cap), 5' untranslated region (5'-UTR), leader sequence, E6 coding region, protease cleavage sequence (furin cleavage site), E7 coding region, 3' untranslated region (3'-UTR) and polyA tail (polyA) may be modified; and the sequence of a nucleic acid molecule capable of expressing the E6 and E7 antigens of HPV16 may consist of a nucleotide sequence having at least 90%, preferably 95% and more preferably 97% identity with any one of the sequences as shown in SEQ ID NOS: 2, 4 and 6. Further, the sequence of a nucleic acid molecule capable of expressing the E6 and E7 antigens of HPV18 may consist of a nucleotide sequence having at least 90%, preferably 95% and more preferably 97% identity with any one of the sequences as shown in SEQ ID NOS: 11 and 13.

The nucleic acid molecule to be encapsulated in the lipid particle may be in any form, as long as it is a nucleic acid molecule capable of expressing the E6 and E7 antigens of human papillomavirus. Examples that may be enumerated include single-stranded DNA, single-stranded RNA (e.g., mRNA), single-stranded polynucleotide in which DNA and RNA are mixed, double-stranded DNA, double-stranded RNA, hybrid polynucleotide of DNA-RNA, and double-stranded polynucleotide consisting of two types of polynucleotides in which DNA and RNA are mixed. Preferably, mRNA is used.

Nucleotides constituting the nucleic acid molecule to be encapsulated in the lipid particle may be either natural or modified nucleotides. Preferably, at least one of the nucleotides is a modified nucleotide.

Modified nucleotides may be modified in any moiety, i.e., base, sugar or phosphodiester bond. The modification may be at either one or two or more sites.

Examples of modified bases include, but are not limited to, cytosine as 5-methylated, 5-fluorinated or N4-methylated; uracil as 5-methylated (thymine) or 5-fluorinated; adenine as N6-methylated; and guanine as N2-methylated.

Examples of modified sugars include, but are not limited to, D-ribofuranose as 2'-O-methylated.

Examples of the modification of phosphodiester bond include, but are not limited to, phosphorothioate bond.

Preferably, modified nucleotides are those in which the base is modified. For example, 5-substituted pyrimidine nucleotide or pseudouridine optionally substituted at position 1 may be given. Specific examples of such modified nucleotide include, but are not limited to, 5-methylcytidine, 5-methoxyuridine, 5-methyluridine, pseudouridine and 1-alkylpseudouridine. As 1-alkylpseudouridine, 1-($C_1$-$C_6$ alkyl) pseudouridine may be given; and preferably, 1-methylpseudouridine or 1-ethylpseudouridine may be enumerated. More preferable examples of modified nucleotide include, but are not limited to, 5-methylcytidine, 5-methyluridine and 1-methylpseudouridine. As examples of especially preferable modified nucleotides, a combination of 5-methylcytidine and 5-methyluridine or a combination of 5-methylcytidine and 1-methylpseudouridine may be given.

The nucleic acid molecule of the present invention capable of expressing the E6 and E7 antigens of human papillomavirus (such as HPV16 or HPV18) may be prepared from a DNA having a desired nucleotide sequence by in vitro transcription reaction. Enzymes, buffers and nucleoside-5'-triphosphate mixture [adenosine-5'-triphosphate (ATP), guanosine-5'-triphosphate (GTP), cytidine-5'-triphosphate (CTP) and uridine-5'-triphosphate (UTP)] that are necessary for in vitro transcription are commercially available (AmpliScribeT7 High Yield Transcription Kit (Epicentre), mMESSAGE mMACHINE T7 Ultra Kit (Life Technologies), and so forth). As regards the DNA to be used for preparing a single-stranded RNA, a cloned DNA (such as plasmid DNA or DNA fragment) is used. As regards plasmid DNA or DNA fragment, commercial products may be used. Alternatively, such DNA may be prepared by methods well known in the art (for example, see those methods described in Sambrook, J. et al., Molecular Cloning a Laboratory Manual second edition (1989); Rashtchian, A., Current Opinion in Biotechnology, 1995, 6(1), 30-36; and Gibson D. G. et al., Science, 2008, 319(5867), 1215-1220).

For the purpose of obtaining an mRNA with improved stability and/or safety, it is also possible to substitute the whole or part of unmodified nucleoside-5'-triphosphate with modified nucleoside-5'-triphosphate in in vitro transcription reaction to thereby substitute the whole or part of unmodified nucleotides in mRNA with modified nucleotides (Kormann, M., Nature Biotechnology, 2011, 29, 154-157).

For the purpose of obtaining an mRNA with improved stability and/or safety, it is also possible to introduce a cap structure (Cap0 structure as defined above) at the 5' end of mRNA after in vitro transcription reaction by a method using a capping enzyme. Further, it is possible to convert Cap0 to Cap1 by acting 2'-O-methyltransferase on mRNA having Cap0. As regards capping enzyme and 2'-O-methyltransferase, commercial products may be used (for example, Vaccinia Capping System, M2080 and mRNA Cap 2'-O-Methyltransferase, M0366, both of which are manufactured by New England Biolab). When commercial products are used, mRNA with a cap structure may be prepared according to the protocols attached to the products.

A cap structure at the 5' end of mRNA may also be introduced by a method different from the one using enzymes. For example, it is possible to introduce into mRNA the structure of a cap analogue which ARCA has or a Cap1 structure derived from CleanCap by adding ARCA or CleanCap to in vitro transcription reaction. As regards ARCA and CleanCap, commercial products may be used (ARCA, N-7003 and CleanCap Reagent AG, N-7113, both of which are manufactured by TriLink BioTechnologies). When commercial products are used, mRNA with a cap structure may be prepared according to the protocols attached to the products.

The lipid particle encapsulating a nucleic acid molecule according to the present invention may be prepared by various methods, such as a thin film method, a reverse phase evaporation method, an ethanol injection method, an ether injection method, a dehydration-rehydration method, a detergent dialysis method, a hydration method, a freezingthawing method, and so forth. For example, the lipid particle encapsulating a nucleic acid molecule may be prepared by the methods described in WO2015/005253. Alternatively, the lipid particle encapsulating a nucleic acid molecule according to the present invention can also be prepared by mixing a nucleic acid solution and a solution of lipids in a micro flow channel. For example, the lipid particle may be prepared with NanoAssemblr™ from Precision NanoSystems, according to the method described in the attached protocol.

The mean particle size of the particle of the present invention may be 30 nm to 300 nm, preferably 30 nm to 200 nm, and more preferably 30 nm to 100 nm. Mean particle size may be obtained by measuring volume mean particle size based on the principle of dynamic light scattering or the like using instruments such as Zeta Potential/Particle Sizer NICOMP™ 380ZLS (Particle Sizing Systems).

The particle of the present invention may be used for preparing a composition for preventing and/or treating those diseases caused by human papillomavirus infections (cervical cancer, cervical dysplasia, anal cancer, oropharyngeal cancer and condyloma acuminatum). The infection may be with a genotype of HPV16, 18, 31, 33, 35, 39, 45, 51, 52, 56, 58, 59, 68, 6 or 11. Infection with HPV16 and/or HPV18 is preferable; and infection with HPV16 is more preferable.

It is possible to express the E6 and E7 antigens of human papillomavirus in vivo or in vitro using the particle of the present invention. Therefore, the present invention provides a method of expressing the E6 and E7 antigens of human papillomavirus in vitro, comprising introducing into cells a composition containing the above-described lipid particle. Further, the present invention also provides a method of expressing the E6 and E7 antigens of human papillomavirus in vivo, comprising administering to a mammal a composition containing the above-described lipid particle. By expressing the E6 and E7 antigens of human papillomavirus in vivo, it is possible to induce immune response to human papillomavirus. As a result, it becomes possible to prevent and/or treat human papillomavirus infections. Therefore, the present invention provides a method of inducing immune response to human papillomavirus, comprising administering to a mammal a composition containing the above-described lipid particle. Further, the present invention provides a method of preventing and/or treating infections with human papillomavirus, comprising administering to a mammal a composition containing the above-described lipid particle.

The particle of the present invention may be used as a pharmaceutical drug or an experimental reagent. The particle of the present invention is usually added to a carrier (such as water, buffer, saline, etc.), and the resultant formulation (composition) may be introduced into a cell (in vitro) or administered to a mammal (in vivo). When the composition is administered to a mammal, the carrier may be a pharmacologically acceptable carrier (e.g., saline). Further, the particle of the present invention may also be prepared into such formulations as cream, paste, ointment, gel, lotion or the like that comprise fat, fatty oil, lanolin, vaseline, paraffin, wax, resin, plastic, glycols, higher alcohol, glycerol, water, emulsifier, suspending agent, and the like as base materials.

The particle of the present invention may be administered to a mammal such as human, mouse, rat, hamster, guinea pig, rabbit, pig, monkey, cat, dog, goat, sheep, cattle, etc. orally or parenterally through various routes such as intramuscular, intravenous, rectal, transdermal, transmucosal, subcutaneous or intradermal administration.

When the particle of the present invention is administered to a human, the particle may be administered, for example, at an approximate dose of 0.001-1 mg, preferably 0.01-0.2 mg per adult per administration either once or several times by intramuscular injection, subcutaneous injection, intradermal injection, intravenous infusion or intravenous injection. The dose and the number of times of administration may be changed appropriately depending on the type and symptoms of the disease, the age of the patient, administration route, etc.

When the particle of the present invention is used as an experimental reagent, it is possible to express the E6 and E7 antigens of human papillomavirus in vitro by introducing the particle into a cell in which expression of the E6 and E7 antigens of human papillomavirus is desired [e.g., HEK293 cells and cells derived therefrom (HEK293T cells, FreeStyle 293 cells, Expi293 cells, etc.), CHO cells, C2C12 mouse myoblast cells, immortalized mouse dendritic cells (MutuDC1940), or the like]. The expression of the E6 and E7 antigens of human papillomavirus may be analyzed by detecting the E6 and E7 antigen proteins of human papillomavirus in samples based on Western blotting or by detecting peptide fragments specific to the E6 and E7 antigens of human papillomavirus based on mass spectrometry.

As used herein, the term "treat" refers to recovery, amelioration, relaxation and/or delaying the progression of clinical symptoms of diseases in patients who are developing infections with viruses or bacteria or diseases caused by such infections (e.g., precancerous lesion or cancer).

As used herein, the term "prevent" refers to reducing the incidence rate of diseases caused by infections with viruses or bacteria. "Prevent" encompasses lowering the risk of progression of diseases caused by infections with viruses or bacteria, or reducing exacerbation of such diseases. Since the particle of the present invention induces protective immune response, the particle of the present invention shows effectiveness on prevention and/or treatment of the above-described diseases.

EXAMPLES

Hereinbelow, the present invention will be described specifically with reference to the following examples. These examples are given only for explanation and are not intended to limit the scope of the present invention.

[Example 1] Preparation of HPV16 E6-E7 fusion2 mRNA-001

(1) Preparation of a Template DNA for In Vitro Transcription (IVT) of HPV16 E6-E7 Fusion2

A plasmid was constructed in order to prepare a template DNA for in vitro transcription (IVT) of HPV16 E6-E7 fusion2. Briefly, a DNA fragment (SEQ ID NO: 1) containing GCTAGC (NheI site), T7 promoter sequence, 5'-UTR sequence of human β-globin, KOZAK sequence, coding region for IgE leader sequence-HPV16 E6-furin cleavage site-HPV16 E7, 3'-UTR sequence of human β-globin, polyA tail, and ACTAGT (SpeI site) was prepared by ligation in this order and then introduced into a plasmid to generate a plasmid of interest (pMA-HPV16_fusion2).

(2) Linearization of the Template DNA

The plasmid generated in Example 1-(1) (250 μg) was dissolved in Nnuclease-Free Water (2200 μl, Thermo Fisher catalog #AM9937). To this solution, 10× CutSmart Buffer (250 μl, New England Biolabs catalog #B7204S) and SpeI- HF (30 μl, New England Biolabs catalog #R3133L) were added, and the resultant mixture was incubated at 37° C. for 2 hours and then at 65° C. for 20 minutes. 7.5 M ammonium acetate (1250 μl) and ethanol (7500 μl) were added and mixed with the incubated solution, which was then left to stand overnight at −20° C. After centrifugation (4° C., 4000×g, 30 minutes), the supernatant was discarded and the precipitate obtained was suspended in 70% ethanol. After centrifugation (4° C., 4000×g, 10 minutes), the supernatant was discarded and the resultant precipitates were collected and air-dried. TE-Buffer was added to the dried precipitate to prepare a template DNA solution of 500 μg/ml.

(3) Preparation of HPV16 E6-E7 Fusion2 mRNA-001 by In Vitro Transcription

The 500 μg/ml template DNA solution from Example 1-(2) (200 μl), 100 mM CleanCap AG (200 μl, TriLink catalog #T-7113), 100 mM ATP (200 μl, Hongene catalog #R1331), 100 mM GTP (200 μl, Hongene catalog #R2331), 100 mM 5-Me-CTP (200 μl, Hongene catalog #R3-029), 100 mM 5-methyluridine triphosphate (200 μl), Nuclease-Free Water (1600 μl, Thermo Fisher catalog #AM9937), T7 Transcription 5× buffer (800 μl, Promega catalog #P140X), Enzyme mix, and T7 RNA Polymerase (400 μl, Promega catalog #P137X) were mixed, and incubated at 37° C. for 4 hours. RQ1 RNase-Free DNase (100 μl, Promega catalog #M6101) was added, and the resultant mixture was incubated at 37° C. for 15 minutes. 8 M LiCl solution (2000 μl, Sigma-Aldrich catalog #L7026) was also added, and the mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water, followed by purification using RNeasy Maxi kit (Qiagen catalog #75162) according to the attached manual. The eluate obtained (10.3 ml; corresponding to 17013 μg DNA on the basis of UV absorbance), Nuclease-Free Water (247 μl), and rApid Alkaline Phosphatase (3403 μl) and the buffer (1550 μl) for this enzyme (Roche catalog #04 898 141 001) were mixed, incubated at 37° C. for 1 hour and then at 75° C. for 15 minutes. 8M LiCl solution (7750 μl) was added, and the resultant mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water and passed through two-connected columns of reversed phase high performance liquid chromatography (Chromolith Semi-Prep (Merck catalog #1.52016.0001)) with 5% acetonitrile, 400 mM triethylamine acetate (pH 7.0)/25% acetonitrile, and 400 mM triethylamine acetate (pH 7.0, 80° C.) used as eluents to purify the mRNA of interest.

The resultant mRNA has the sequence as shown in SEQ ID NO: 2. The mRNA was analyzed with Experion RNA StdSens (BIO-RAD catalog #7007103JA) to thereby confirm that the mRNA has an anticipated nucleotide length.

[Example 2] Preparation of HPV16 E6-E7 Fusion10 mRNA-001

(1) Preparation of a Template DNA for IVT of HPV16 E6-E7 Fusion10

A plasmid was constructed in order to prepare a template DNA for IVT of HPV16 E6-E7 fusion10. Briefly, a DNA fragment (SEQ ID NO: 3) containing GCTAGC (NheI site), T7 promoter sequence, 5'-UTR sequence of $-globin, KOZAK sequence, coding region for IgE leader sequence-HPV16 E6-furin cleavage site-HPV16 E7, 3'-UTR sequence of $-globin, polyA tail, and ACTAGT (SpeI site) was prepared by ligation in this order and then introduced into a plasmid to generate a plasmid of interest (pMA-HPV16_fusion10).

(2) Preparation of HPV16 E6-E7 Fusion10 mRNA-001 by In Vitro Transcription

Using the plasmid from Example 2-(1) instead of the plasmid from Example 1-(1), the mRNA was obtained in the same manner as described in Example 1-(2) and -(3).

The resultant mRNA has the sequence as shown in SEQ ID NO: 4. It was confirmed by the analysis with Experion RNA StdSens that this mRNA has an anticipated nucleotide length.

[Example 3] Preparation of HPV16 E6-E7 Fusion10 mRNA-002

Using the plasmid from Example 2-(1) instead of the plasmid from Example 1-(1), a template DNA was obtained in the same manner as described in Example 1-(2). Subsequently, using the resultant template DNA and 100 mM Pseudo-UTP (Hongene catalog #R5-022) instead of the template DNA from Example 1-(3) and 100 mM 5-Me-UTP, respectively, the mRNA was obtained in the same manner as described in Example 1-(3).

The resultant mRNA has the sequence as shown in SEQ ID NO: 4. It was confirmed by the analysis with Experion RNA StdSens that this mRNA has an anticipated nucleotide length.

[Example 4] Preparation of HPV16 E6-E7 Fusion10 mRNA-003

Using the plasmid from Example 2-(1) instead of the plasmid from Example 1-(1), a template DNA was obtained in the same manner as described in Example 1-(2). Subsequently, using the resultant template DNA, 100 mM CTP (Hongene catalog #R3331), and 100 mM N1-methylpeseudouridine-5'-triphosphate (TriLink catalog #N-1081) instead of the template DNA from Example 1-(3), 100 mM 5-Me-CTP, and 100 mM 5-Me-UTP, respectively, the mRNA was obtained in the same manner as described in Example 1-(3).

The resultant mRNA has the sequence as shown in SEQ ID NO: 4. It was confirmed by the analysis with Experion RNA StdSens that this mRNA has an anticipated nucleotide length.

[Example 5] Preparation of HPV16 E6-E7 Fusion10 mRNA-004

Using the plasmid from Example 2-(1) instead of the plasmid from Example 1-(1), a template DNA was obtained in the same manner as described in Example 1-(2). Subsequently, using the resultant template DNA and 100 mM CTP (Hongene catalog #R3331) instead of the template DNA from Example 1-(3) and 100 mM 5-Me-CTP, respectively, the mRNA was obtained in the same manner as described in Example 1-(3).

The resultant mRNA has the sequence as shown in SEQ ID NO: 4. It was confirmed by the analysis with Experion RNA StdSens that this mRNA has an anticipated nucleotide length.

[Example 6] Preparation of HPV16 E6-E7 Fusion10 Opt2 mRNA-001

(1) Preparation of a Template DNA for IVT of HPV16 E6-E7 Fusion10 Opt2

A plasmid was constructed in order to prepare a template DNA for IVT of HPV16 E6-E7 fusion10 opt2. Briefly, a DNA fragment (SEQ ID NO: 5) containing GCTAGC (NheI site), T7 promoter sequence, 5'-UTR sequence of $-globin, KOZAK sequence, coding region for IgE leader sequence-HPV16 E6-furin cleavage site-HPV16 E7, 3'-UTR sequence of $-globin, polyA tail, and ACTAGT (SpeI site) was prepared by ligation in this order and then introduced into a plasmid to generate a plasmid of interest (pMA-HPV16_fusion10_opt2).

(2) Linearization of the Template DNA

The plasmid generated in Example 6-(1) (250 μg) was dissolved in Nnuclease-Free Water (2200 μl, Thermo Fisher catalog #AM9937). To this solution, 10× CutSmart Buffer (250 μl, New England Biolabs catalog #B7204S) and SpeI-HF (30 μl, New England Biolabs catalog #R3133L) were added, and the resultant mixture was incubated at 37° C. for 2 hours and then at 65° C. for 20 minutes. 7.5 M ammonium acetate (1250 μl) and ethanol (7500 μl) were added and mixed with the incubated solution, which was then left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the resultant precipitate was collected and air-dried. TE-Buffer was added to the dried precipitate to prepare a template DNA solution of 500 μg/ml.

(3) Preparation of HPV16 E6-E7 Fusion10 Opt2 mRNA-001 by In Vitro Transcription

500 μg/ml template DNA from Example 6-(2) (100 μl), 100 mM ATP (150 μl, Hongene catalog #R1331), 100 mM GTP (150 μl, Hongene catalog #R2331), 100 mM CTP (150 μl, Hongene catalog #R3331), 100 mM N1-methylpseudouridine-5'-triphosphate (150 μl, Hongene catalog #R5-027), Nuclease-Free Water (700 μl, Thermo Fisher catalog #AM9937), T7 Transcription 5× buffer (400 μl, Promega catalog #P140X), Enzyme mix, and T7 RNA Polymerase (200 μl, Promega catalog #P137X) were mixed, and-incubated at 37° C. for 4 hours. RQ1 RNase-Free DNase (50 μl, Promega catalog #M6101) was added, and the resultant mixture was incubated at 37° C. for 15 minutes. 8 M LiCl solution (1000 μl, Sigma-Aldrich catalog #L7026) was further added, and the mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water. To this solution (962 μl; corresponding to 5400 g of RNA on the basis of UV absorbance), Nuclease-Free Water (2818 μl) was added. The resultant solution was heated at 70° C. for 20 minutes and then cooled on ice for 10 minutes. To this solution, 540 μl of 10× capping buffer (500 mM Tris-HCl (pH 8.0), 50 mM KCl, 10 mM $MgCl_2$, 50 mM DTT), 20 mM GTP (270 μl; 100 mM GTP, prepared by diluting Hongene catalog #R2331 with Nuclease-FreeWater), 20 mM SAM (270 μl; 32 mM SAM, prepared by diluting New England Biolabs catalog #B9003S with Nuclease-Free Water), and Vaccinia Capping Enzyme (540 μl; Hongene catalog #ON-028) were added, and the resultant mixture was incubated at 37° C. for 4 hours. Then, 10× capping buffer (90 μl), 20 mM SAM (270 μl) and 2'-O-methyltransferase (540 μl; Hongene catalog #ON-014) were added thereto, and the resultant mixture was incubated at 37° C. for 4 hours. 8 M LiCl solution (6300 μl) was further added, and the mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water and passed through two-connected columns of reversed phase high performance liquid chromatography (Chromolith Semi-Prep (Merck catalog #1.52016.0001)) with 5% acetonitrile, 400 mM triethylamine acetate (pH 7.0)/25% acetonitrile, and 400 mM triethylamine acetate (pH 7.0, 80° C.) as eluents to thereby purify the mRNA of interest.

The resultant mRNA has the sequence as shown in SEQ ID NO: 6. It was confirmed by the analysis with Experion RNA StdSens that this mRNA has an anticipated nucleotide length.

(4) Preparation of HPV16 E6-E7 Fusion10 Opt2 mRNA-001 by In Vitro Transcription

500 μg/ml template DNA from Example 6-(2) (200 μl), 100 mM ATP (300 μl, Hongene catalog #R1331), 100 mM GTP (300 μl, Hongene catalog #R2331), 100 mM CTP (300 W, Hongene catalog #R3331), 100 mM N1-methylpseudouridine-5'-triphosphate (300 μl, Hongene catalog #R5-027), Nuclease-Free Water (1400 μl, Applied-Bio catalog #AM9937), T7 Transcription 5× buffer (800 μl) (400 mM HEPES-KOH (pH 7.5), 80 mM $MgCl_2$, 10 mM spermidine, 200 mM DTT), Enzyme mix, and T7 RNA Polymerase (400 μl, Promega catalog #P137X) were mixed and incubated at 37° C. for 8 hours. RQ1 RNase-Free DNase (100 μl, Promega catalog #M6101) was added, and the resultant mixture was incubated at 37° C. for 15 minutes. 8 M LiCl solution (2000 μl, Sigma-Aldrich catalog #L7026) was further added, and the resultant mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water. To this solution (1590 μl; corresponding to 6000 μg of RNA on the basis of UV absorbance), Nuclease-Free Water (2610 μl) was added. The resultant solution was heated at 70° C. for 10 minutes and then cooled on ice for 10 minutes. To this solution, 600 μl of 10× capping buffer (500 mM Tris-HCl (pH 8.0), 50 mM KCl, 10 mM $MgCl_2$, 50 mM DTT), 20 mM GTP (300 μl; 100 mM GTP, prepared by diluting Hongene catalog #R2331 with Nuclease-Free Water), 20 mM SAM [300 μl; prepared by dissolving S-adenosyl-L-methionine disulfate tosylate (OX-CHEM catalog #AX8250818)-in 10% ethanol solution of 0.005 M sulfuric acid] and Vaccinia Capping Enzyme (600 μl; Hongene catalog #ON-028) were added, and the resultant mixture was incubated at 37° C. for 4 hours. Then, 10× capping buffer (100 μl), 20 mM SAM (300 μl) and 2'-O-methyltransferase (600 μl; Hongene catalog #ON-014) were added thereto, and the resultant mixture was incubated at 37° C. for 4 hours. 8 M LiCl solution (7000 μl) was further added, and the mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water and passed through a column of reversed phase high performance liquid chromatography (Chromolith Performance (Merck catalog #1.02129.0001) with 5% acetonitrile, 400 mM triethylamine acetate (pH 7.0)/25% acetonitrile, 400 mM triethylamine acetate (pH 7.0, 45° C.) as eluents to thereby purify the mRNA of interest.

The resultant mRNA has the sequence as shown in SEQ ID NO: 6. It was confirmed by the analysis with LabChip GX Touch HT mRNA StdSens (PerkinElmer catalog #CLS960010) that this mRNA has an anticipated nucleotide length.

[Example 7] Preparation of HPV16 E6-E7 Fusion10 Opt2 mRNA-002

The mRNA was obtained in the same manner as described in Example 6-(3) except that 100 mM 5-Me-CTP and 100 mM 5-methyluridine triphosphate were used instead of 100 mM CTP and 100 mM N1-methylpseudouridine-5'-triphosphate, respectively. The resultant mRNA has the sequence as shown in SEQ ID NO: 6. It was confirmed by the analysis with Experion RNA StdSens that this mRNA has an anticipated nucleotide length.

[Example 8] Preparation of Nucleic Acid Lipid Particles Encapsulating the HPV mRNA of Example 1

(1) Preparation of Nucleic Acid Lipid Particles Encapsulating mRNA

Distearoyl phosphatidylcholine (1,2-Distearoyl-sn-glycero-3-phosphocholine; hereinafter, designated as DSPC; NOF CORPORATION), cholesterol (hereinafter, designated as Chol; Sigma-Aldrich, Inc.), (7R,9Z,26Z,29R)-18-({[3-(dimethylamino)propoxy]carbonyl}oxy)pentatriaconta-9,26-diene-7,29-diyl diacetate (a compound disclosed in Example 23 in WO2015/005253) (hereinafter, designated as LP) and 1,2-dimyristoyl-sn-glycerol-3-methoxypolyethylene glycol in which the polyethylene glycol part has the molecular weight of about 2000 (hereinafter, designated as PEG-DMG; NOF CORPORATION) were dissolved in ethanol so that a molar ratio of DSPC:Chol:LP:PEG-DMG is 10:43.5:45:1.5 to give a total lipid concentration of 5 mM.

On the other hand, HPV16 fusion2 mRNA-001 obtained in Example 1 was diluted with 20 mM citrate buffer (pH 4.0) to prepare a solution of 51.8 μg/ml.

The lipid solution and the mRNA solution described above were mixed to give a volume ratio of 1:3 in a micro flow channel using NanoAssemblr BenchTop (Precision Nanosystems Inc.) to thereby obtain a crude dispersion of nucleic acid lipid particles. This dispersion was dialyzed against about 25 to 50 volumes of phosphate buffer (pH 7.4) for 12 to 18 hours (Float-A-Lyzer G2, MWCO: 1,000 kD, Spectra/Por) to thereby remove ethanol and obtain a purified dispersion of nucleic acid lipid particles encapsulating mRNA.

LP was synthesized according to the method described in Example 23 of WO2015/005253.

(2) Characterization of Nucleic Acid Lipid Particles Encapsulating mRNA

The dispersion containing the nucleic acid lipid particles prepared in (1) above was characterized. Methods of characterization of each property will be described below.

(2-1) Encapsulation Rate of mRNA

Encapsulation rate of mRNA was measured with Quant-iT RiboGreen RNA Assay kit (Invitrogen) according to the attached protocol with necessary modifications.

Briefly, mRNA in the dispersion of nucleic acid lipid particles was quantified in the presence or absence of 0.015% Triton X-100 surfactant, and then encapsulation rate was calculated by the following formula.

{[amount of mRNA in the presence of surfactant]−[amount of mRNA in the absence of surfactant]}/[amount of mRNA in the presence of surfactant]}×100(%).

(2-2) Ratio of mRNA and Lipids

The amount of mRNA in the dispersion of nucleic acid lipid particles was measured by reversed phase chromatography (System: Agilent 1100 series; Column: Bioshell A400 Protein C4 (10 cm×4.6 mm, 3.4 μm) (SUPELCO); Buffer A: 0.1 M triethylamine acetate (pH 7.0); Buffer B: acetonitrile; (B %): 5-50% (0-15 min); Flow Rate: 1 ml/min; Temperature: 70° C.; Detection: 260 nm).

The amount of each lipid in the dispersion of nucleic acid lipid particles was measured by reversed phase chromatography (System: DIONEX UltiMate 3000; Column: XSelect CSH (50 mm×3 mm, 5 μm) (Thermo Fisher Scientific); Buffer A: 0.2% formic acid; Buffer B: 0.2% formic acid, methanol; (B %): 75-95% (0-15 min), 95% (15-17 min); Flow Rate: 0.4 ml/min; Temperature: 50° C.; Detection: Corona CAD (Charged Aerosol Detector)).

The ratio of the total lipid to mRNA was calculated by the following formula.

[Total lipid concentration]/[mRNA concentration] (wt/wt)

(2-3) Mean Particle Size

The mean particle size of nucleic acid lipid particles in a dispersion was measured with Zeta Potential/Particle Sizer NICOMP™ 380ZLS (Particle Sizing Systems). The mean particle size in the dispersion represents the volume mean particle sizes together with its deviation.

The results are shown in Table 1.

[Examples 9 to 13] Preparation of Nucleic Acid Lipid Particles Encapsulating HPV mRNA The nucleic acid lipid particles encapsulating the mRNA described in Example 2, 3, 4, 5 or 6 were prepared and characterized in the same manner as described in Example 8, except that the lipid composition used had a molar ratio of 12.5:41:45:1.5 for DSPC:Chol:LP:PEG-DMG. The results are shown in Table 1.

[Examples 14 to 17] Preparation of Nucleic Acid Lipid Particles Encapsulating HPV mRNA The nucleic acid lipid particles encapsulating the mRNA described in Example 2, 4, 6 or 7 were prepared and characterized in the same manner as described in Example 8, except that the lipid composition used had a molar ratio of 12.5:41:45:1.5 for DSPC:Chol:LP:PEG-DMG. The results are shown in Table 1.

[Example 18] Preparation of Nucleic Acid Lipid Particles Encapsulating the HPV mRNA of Example 2

The nucleic acid lipid particles encapsulating the mRNA described in Example 2 were prepared and characterized in the same manner as described in Example 8, except that the lipid composition used had a molar ratio of 12.5:41:45:1.5 for DSPC:Chol:LP:PEG-DMG and that the ratio of the total lipid weight to mRNA weight was 25. The results are shown in Table 1.

[Example 19] Preparation of Nucleic Acid Lipid Particles Encapsulating the HPV mRNA of Example 2

The nucleic acid lipid particles encapsulating the mRNA described in Example 2 were prepared and characterized in the same manner as described in Example 8, except that the lipid composition had a molar ratio of 12.5:41:45:1.5 for DSPC:Chol:LP:PEG-DMG, and the ratio of the total lipid weight to mRNA weight was 30. The results are shown in Table 1.

[Example 20] Preparation of Nucleic Acid Lipid Particles Encapsulating the HPV mRNA of Example 2

The nucleic acid lipid particles encapsulating the mRNA described in Example 2 were prepared and characterized in the same manner as described in Example 8. The results are shown in Table 1.

[Example 21] Preparation of Nucleic Acid Lipid Particles Encapsulating OVA mRNA (1) Preparation of Nucleic Acid Lipid Particles Encapsulating mRNA The nucleic acid lipid particles encapsulating an mRNA having the coding region of OVA (ovalbumin) as shown in SEQ ID NO: 7 were prepared in the same manner as described in Example 8-(1). However, instead of PEG-DMG, N-[methoxy poly(ethylene glycol)2000 carbamoyl]-1,2-dimyristyloxypropyl-3-amine in which the polyethylene glycol part has the molecular weight of about 2000 (hereinafter, designated as PEG-C-DMA; corresponding to compound 12 disclosed in Journal of Controlled Release 112 (2006) 280-290) was used, and the lipid composition of the nucleic acid lipid particles had a molar ratio of 10:38.5:50:1.5 for DSPC:Chol:LP:PEG-C-DMA.

(2) Characterization of Nucleic Acid Lipid Particles Encapsulating mRNA

A dispersion containing the nucleic acid lipid particles prepared in (1) above was characterized. Methods of characterization of each property will be described below.

(2-1) Encapsulation Rate of mRNA

Encapsulation rate of mRNA was measured with Quant-iT RiboGreen RNA Assay kit (Invitrogen) according to the attached protocol with necessary modifications.

Briefly, mRNA in the dispersion of the nucleic acid lipid particles was quantified in the presence or absence of 0.015% Triton X-100 surfactant, and then encapsulation rate was calculated by the following formula.

{[amount of mRNA in the presence of surfactant]−[amount of mRNA in the absence of surfactant]}/[amount of mRNA in the presence of surfactant]}×100(%)

(2-2) Ratio of mRNA and Lipids

The amount of mRNA in the presence of surfactant in (2-1) was regarded as the amount of mRNA in the dispersion of the nucleic acid lipid particles.

The amount of phospholipids in the dispersion of the nucleic acid lipid particles was measured with Phospholipids C-test Wako kit (Fuji Film Wako Purechemicals) according to the attached protocol with necessary modification. Briefly, the amount of phospholipids in the dispersion was measured in the presence of 2% Triton X-100 surfactant.

The amounts of cholesterol and LP in the dispersion of the nucleic acid lipid particles were measured by reversed phase chromatography (System: DIONEX UltiMate 3000; Column: Chromolith Performance RP-18 endcapped 100-3 monolithic HPLC-column (Merck, Cat. #1.52001.0001); Buffer A: 0.01% trifluoroacetate; Buffer B: 0.01% trifluoroacetate, methanol; (B %): 82-97% (0-17 min); Flow Rate: 2 ml/min; Temperature: 50° C.; Detection: Corona CAD (Charged Aerosol Detector)).

The amount of total lipid and the ratio of lipid components constituting the nucleic acid lipid particles was calculated from measured values of phospholipids, cholesterol and LP.

The ratio of the total lipid to mRNA was calculated by the following formula.

[total lipid concentration]/[mRNA concentration](wt/wt)

(2-3) Mean Particle Size

The mean particle size of nucleic acid lipid particles was measured with Zeta Potential/Particle Sizer NICOMP™ 380ZLS (Particle Sizing Systems). The mean particle size represents the volume mean particle sizes together with its deviation.

The results are shown in Table 2.

[Example 22] Preparation of Nucleic Acid Lipid Particles Encapsulating OVA mRNA

The nucleic acid lipid particles encapsulating the mRNA having the coding region of OVA (ovalbumin) as shown in SEQ ID NO: 7 were prepared and characterized in the same manner as described in Example 21, except that the lipid composition used had a molar ratio of 10:35:50:5 for DSPC:Chol:LP:PEG-C-DMA. The results are shown in Table 2.

[Example 23] Preparation of Nucleic Acid Lipid Particles Encapsulating OVA mRNA

The nucleic acid lipid particles encapsulating the mRNA having the coding region of OVA as shown in SEQ ID NO: 7 were prepared and characterized in the same manner as described in Example 21, except that the lipid composition used had a molar ratio of 10:23.5:65:1.5 for DSPC:Chol:LP:PEG-C-DMA. The results are shown in Table 2.

[Example 24] Preparation of Nucleic Acid Lipid Particles Encapsulating OVA mRNA

The nucleic acid lipid particles encapsulating the mRNA having the coding region of OVA as shown in SEQ ID NO: 7 were prepared and characterized in the same manner as described in Example 21, except that the lipid composition used had a molar ratio of 10:48.5:40:1.5 for DSPC:Chol:LP:PEG-C-DMA. The results are shown in Table 2.

[Example 25] Preparation of Nucleic Acid Lipid Particles Encapsulating OVA mRNA

The nucleic acid lipid particles encapsulating the mRNA having the coding region of OVA as shown in SEQ ID NO: 7 were prepared and characterized in the same manner as described in Example 21, except that the lipid composition used had a molar ratio of 5:43.5:50:1.5 for DSPC:Chol:LP:PEG-C-DMA The results are shown in Table 2.

[Example 26] Preparation of Nucleic Acid Lipid Particles Encapsulating OVA mRNA

The nucleic acid lipid particles encapsulating the mRNA having the coding region of OVA as shown in SEQ ID NO:

7 were prepared and characterized in the same manner as described in Example 21, except that the lipid composition used had a molar ratio of 15:33.5:50:1.5 for DSPC:Chol:LP:PEG-C-DMA. The results are shown in Table 2.

[Example 27] Preparation of Nucleic Acid Lipid Particles Encapsulating OVA mRNA

The nucleic acid lipid particles encapsulating the mRNA having the coding region of OVA as shown in SEQ ID NO: 7 were prepared and characterized in the same manner as described in Example 21, except that the lipid composition used had a molar ratio of 53.5:45:1.5 for Chol:LP:PEG-C-DMA. The results are shown in Table 2.

[Example 28] Preparation of Nucleic Acid Lipid Particles Encapsulating the HPV mRNA of Example 4

The nucleic acid lipid particles encapsulating the HPV mRNA described in Example 4 were prepared and characterized in the same manner as described in Example 8, except that dioleoyl phosphatidylcholine (1,2-Dioleoyl-sn-glycero-3-phosphocholine; hereinafter, designated as DOPC: NOF CORPORATION) was used instead of DSPC, so that the lipid composition had a molar ratio of 10:43.5:45:1.5 for DOPC:Chol:LP:PEG-DMG. The results are shown in Table 3.

[Example 29] Preparation of Nucleic Acid Lipid Particles Encapsulating the HPV mRNA of Example 4

The nucleic acid lipid particles encapsulating the HPV mRNA described in Example 4 were prepared and characterized in the same manner as described in Example 8, except that DOPC was used instead of DSPC, so that the lipid composition had a molar ratio of 15:38.5:45:1.5 for DOPC:Chol:LP:PEG-DMG. The results are shown in Table 3.

[Example 30] Preparation of Nucleic Acid Lipid Particles Encapsulating the HPV mRNA of Example 4

The nucleic acid lipid particles encapsulating the HPV mRNA described in Example 4 were prepared and characterized in the same manner as described in Example 8, except that dioleoyl phosphatidyl ethanolamine (1,2-Dioleoyl-sn-glycero-3-phosphoethanolamine; hereinafter, designated as DOPE; NOF CORPORATION) was used instead of DSPC, so that the lipid composition had a molar ratio of 10:43.5:45:1.5 for DOPE:Chol:LP:PEG-DMG. The results are shown in Table 3.

[Example 31] Preparation of Nucleic Acid Lipid Particles Encapsulating the HPV mRNA of Example 4

The nucleic acid lipid particles encapsulating the HPV mRNA described in Example 4 was prepared and characterized in the same manner as described in Example 8, except that DOPE was used instead of DSPC, so that the lipid composition had a molar ratio had a molar ratio of 15:38.5:45:1.5 for DOPE:Chol:LP:PEG-DMG. The results are shown in Table 3.

[Example 32] Preparation of Nucleic Acid Lipid Particles Encapsulating the HPV mRNA of Example 4

The nucleic acid lipid particles encapsulating the HPV mRNA described in Example 4 was prepared and characterized in the same manner as described in Example 8, except that the lipid composition used had a molar ratio of 12.5:41:45:1.5 for DSPC:Chol:LP:PEG-DMG. The results are shown in Table 3.

[Example 33] Preparation of HPV18 E6-E7 Fusion1 Opt1 mRNA-001

(1) Preparation of a Template DNA for In Vitro Transcription (IVT) of HPV18 E6-E7 Fusion1 Opt1

A plasmid was constructed in order to prepare a template DNA for IVT. Briefly, a DNA fragment (SEQ ID NO: 10) comprising GCTAGC (NheI site), T7 promoter sequence, 5'-UTR sequence of human β-globin, KOZAK sequence, ORF for IgE leader sequence-HPV18 E6-furin cleavage site-HPV18 E7, 3'-UTR sequence of human β-globin, polyA tail and ACTAGT (SpeI site) was prepared by ligation in this order and then introduced into a plasmid to generate a plasmid of interest (pMA-HPV18_fusion1_opt1).

(2) Linearization of the Template DNA

The plasmid generated in Example 33-(1) (350 μg) was dissolved in Nuclease-Free Water (3080 μl, Thermo Fisher catalog #AM9937). To this solution, 10× CutSmart Buffer (350 μl, New England Biolabs catalog #B7204S) and SpeI-HF (70 μl, New England Biolabs catalog #R3133L) were added, and the resultant mixture was incubated at 37° C. for 2 hours and then at 65° C. for 20 minutes. 7.5 M ammonium acetate (1750 μl) and ethanol (10500 μl) were added and mixed with the incubated solution, which was then left to stand overnight at −80° C. After centrifugation (−10° C., 4000×g, 30 minutes), the supernatant was discarded and 70% ethanol was added to the precipitate. After centrifugation (−10° C., 4000×g, 10 minutes), the supernatant was discarded and the precipitate obtained was collected and air-dried. TE-Buffer was added to the air-dried precipitate to prepare a template DNA solution of 500 μg/ml.

(3) Preparation of HPV18 E6-E7 Fusion1 Opt1 mRNA-001 by In Vitro Transcription

500 μg/ml template DNA from Example 33-(2) (150 μl), 100 mM CleanCap AG (150 μl, TriLink catalog #T-7113), 100 mM ATP (150 μl, Hongene catalog #R1331), 100 mM GTP (150 μl, Hongene catalog #R2331), 100 mM CTP (150 μl, Hongene catalog #R3331), 100 mM N1-Me-Pseudo UTP (150 μl, Hongene catalog #R5-027), Nuclease-Free Water (1200 μl, Thermo Fisher catalog #AM9937), T7 Transcription 5× buffer (600 μl, Promega catalog #P140X), Enzyme mix, and T7 RNA Polymerase (300 μl, Promega catalog #P137X) were mixed, and-incubated at 37° C. for 4 hours. RQ1 RNase-Free DNase (75 μl, Promega catalog #M6101) was added and the resultant mixture was incubated at 37° C. for 15 minutes. 8 M LiCl solution (1500 μl, Sigma-Aldrich catalog #L7026) was further added, and the resultant mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water, followed by purification using RNeasy Maxi kit (Qiagen catalog #75162) according to the attached manual. A portion of the eluate obtained (11.0 ml; corresponding to 9813 μg of RNA on the basis of UV absorbance), Nuclease-free water (537 μl), and rApid Alkaline Phosphatase and the buffer for (1500 μl) for this enzyme (Roche catalog #04 898 141 001) were mixed. The mixture was incubated at 37° C. for 30 minutes and then at 75° C. for 3 minutes. 8 M LiCl solution (15000 μl) was added, and the resultant mixture was left to stand for 3 hours at −20° C. After centrifugation (−8° C., 4000×g, 30 minutes), the supernatant was discarded and 70% ethanol was added to the precipitate. After centrifugation (−8° C., 4000×g, 10 minutes), the supernatant was discarded and the precipitate obtained was air-dried. The air-dried precipitate was dissolved in Nuclease-Free Water and passed through a column of reversed phase high performance liquid chromatography (YMC Triart-C8 5 μm 10×150 mm (YMC #TO12S05-1510WT)) with 5% acetonitrile, 400 mM triethylamine acetate (pH 7.0)/25% acetonitrile, 400 mM triethylamine acetate (pH 7.0, 75° C.) as eluents to thereby purify the mRNA of interest.

The resultant mRNA has the sequence as shown in SEQ ID NO: 11. It was confirmed by the analysis with LabChip GX Touch Standard RNA Reagent Kit (PerkinElmer catalog #CLS960010) that this mRNA has an anticipated nucleotide length.

[Example 34] Preparation of HPV18 E6-E7 Fusion1 Opt1 mRNA-002

The mRNA was obtained in the same manner as described in Example 33-(3) except that 100 mM 5-Me-CTP (Hongene catalog #R3-029) and 100 mM 5-methyluridine triphosphate were used instead of 100 mM CTP and 100 mM N1-Me-Pseudo UTP, respectively.

The resultant mRNA has the sequence as shown in SEQ ID NO: 11. It was confirmed by the analysis with LabChip GX Touch Standard RNA Reagent Kit (PerkinElmer catalog #CLS960010) that this mRNA has an anticipated nucleotide length.

[Example 35] Preparation of HPV18 E6-E7 Fusion1 Opt2 mRNA-001

(1) Preparation of a Template DNA for IVT of HPV18 E6-E7 Fusion1 Opt2

A plasmid was constructed in order to prepare a template DNA for IVT. Briefly, a DNA fragment (SEQ ID NO: 12) containing GCTAGC (NheI site), T7 promoter sequence, 5'-UTR sequence of β-globin, KOZAK sequence, ORF for IgE leader sequence-HPV18 E6-furin cleavage site-HPV18 E7, 3'-UTR sequence of $-globin, polyA tail and ACTAGT (SpeI site) was prepared by ligation in this order and then introduced into a plasmid to generate the plasmid of interest (pMA-HPV18_fusion1_opt2).

(2) Linearization of the Template DNA

The plasmid generated in Example 35-(1) (400 μg) was dissolved in Nuclease-Free Water (3520 μl, Thermo Fisher catalog #AM9937). To this solution, 10× CutSmart Buffer (400 μl, New England Biolabs catalog #B7204S) and SpeI-HF (80 μl, New England Biolabs catalog #R3133L) were added, and the resultant mixture was incubated at 37° C. for 2 hours and then at 65° C. for 20 minutes. 7.5 M ammonium acetate (1750 μl) and ethanol (10500 μl) were added and mixed with the incubated solution, which was then left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the resultant precipitate was collected and air-dried. TE-Buffer was added to the air-dried precipitate to prepare a template DNA solution of 500 μg/ml.

(3) Preparation of HPV16 E6-E7 Fusion1 Opt2 mRNA-001 by In Vitro Transcription

500 μg/ml template DNA from Example 35-(2) (150 μl), 100 mM ATP (225 μl, Hongene catalog #R1331), 100 mM GTP (225 μl, Hongene catalog #R2331), 100 mM CTP (225 μl, Hongene catalog #R3331), 100 mM N1-Me-Pseudo UTP (225 μl, Hongene catalog #R5-027), Nuclease-Free Water (1050 μl, Thermo Fisher catalog #AM9937), T7 Transcription 5× buffer (600 μl, Promega catalog #P140X), Enzyme mix, and T7 RNA Polymerase (300 μl, Promega catalog #P137X) were mixed, and incubated at 37° C. for 4 hours. RQ1 RNase-Free DNase (75 μl, Promega catalog #M6101) was added, and the resultant mixture was incubated at 37° C. for 15 minutes. 8 M LiCl solution (1500 μl, Sigma-Aldrich catalog #L7026) was further added, and the resultant mixture was left to stand overnight at −20° C. After centrifugation (4° C., 4000×g, 30 minutes), the supernatant was discarded and 70% ethanol was added to the precipitate. After centrifugation (4° C., 4000×g, 10 minutes), the supernatant was discarded and the precipitate obtained was air-dried. The air-dried precipitate was dissolved in Nuclease-Free Water. Nuclease-Free Water (2780 μl) was added to a portion of this solution (2470 μl; corresponding to 7500 μg of RNA on the basis of UV absorbance). The resultant solution was heated at 70° C. for 10 minutes and then cooled on ice for 5 minutes. 750 μl of 10× capping buffer (500 mM Tris-HCl (pH 8.0), 50 mM KCl, 10 mM $MgCl_2$, 50 mM DTT), 20 mM GTP (375 μl; 100 mM GTP; prepared by diluting Hongene catalog #R2331 with Nuclease-Free Water), 20 mM SAM (375 μl; 32 mM SAM; prepared by diluting New England Biolabs catalog #B9003S with Nuclease-Free Water), and Vaccinia Capping Enzyme (750 μl; Hongene catalog #ON-028) were added thereto, and the resultant mixture was incubated at 37° C. for 4 hours. Then, 10× capping buffer (125 μl), 20 mM SAM (375 μl), and 2'-O-methyltransferase (750 μl; Hongene catalog #ON-014) were added thereto, and the resultant mixture was incubated at 37° C. for 4 hours. 8 M LiCl solution (8750 μl) was further added, and the resultant mixture was left to stand overnight at −20° C. After centrifugation (−8° C., 4000×g, 30 minutes), the supernatant was discarded and 70% ethanol was added to the precipitate. After centrifugation (−8° C., 4000×g, 10 minutes), the supernatant was discarded and the precipitate obtained was air-dried. The air-dried precipitate was dissolved in Nuclease-Free Water and passed through a column of reversed phase high performance liquid chromatography (YMC Triart-C8 5 μm 10×150 mm (YMC #TO12S05-1510WT) with 5% acetonitrile, 400 mM triethylamine acetate (pH 7.0)/25% acetonitrile, and 400 mM triethylamine acetate (pH 7.0, 75° C.) as eluents to thereby purify the mRNA of interest.

The resultant mRNA has the sequence as shown in SEQ ID NO: 13. It was confirmed by the analysis with LabChip GX Touch Standard RNA Reagent Kit (PerkinElmer catalog #CLS960010) that this mRNA has an anticipated nucleotide length.

[Example 36] Preparation of HPV18 E6-E7 Fusion1 Opt2 mRNA-002

The mRNA was obtained in the same manner as described in Example 35-(3) except that 100 mM 5-Me-CTP (Hongene catalog #R3-029) and 100 mM 5-methyluridine triphosphate were used instead of 100 mM CTP and-100 mM N1-Me-Pseudo UTP, respectively.

The resultant mRNA has the sequence as shown in SEQ ID NO: 13. It was confirmed by the analysis with LabChip GX Touch Standard RNA Reagent Kit (PerkinElmer catalog #CLS960010) that this mRNA has an anticipated nucleotide length.

[Examples 37 to 40] Preparation of Nucleic Acid Lipid Particles Encapsulating HPV mRNA (1) Preparation of Nucleic Acid Lipid Particles Encapsulating mRNA Nucleic acid lipid particles encapsulating mRNA were prepared and characterized in the same manner as described in Example 8, except that the mRNAs from Examples 33 to 36 were used instead of the mRNA of Example 1. The molar ratio of the lipids used for each preparation is indicated in Table 4. The results are shown in Table 4.

[Examples 41 to 52] Preparation of Nucleic Acid Lipid Particles Encapsulating HPV mRNA (1) Preparation of Nucleic Acid Lipid Particles Encapsulating mRNA Nucleic acid lipid particles encapsulating the mRNA of Example 4 were prepared in the same manner as described in Example 8, except that (7R,9Z)-18-({[3-(dimethylamino)propyloxy]carbonyl}oxy)octacosa-9-ene-7-yl acetate (a compound disclosed in Example 28 in WO2015/005253) (hereinafter, designated as LP2) was used instead of (7R,9Z,26Z,29R)-18-({[3-(dimethylamino)propoxy]carbonyl}oxy)pentatriaconta-9,26-diene-7,29-diyl diacetate. The molar ratio of the lipids used is indicated in Table 5.

LP2 was synthesized according to the method described in Example 28 of-WO2015/005253.

(2) Characterization of Nucleic Acid Lipid Particles Encapsulating mRNA

Nucleic acid lipid particles encapsulating mRNA were characterized in the same manner as described in Example 8, and the amount of mRNA encapsulated was analyzed as described below.

Briefly, a dispersion of nucleic acid lipid particles was dissolved in 90% methanol, and the amount of mRNA was measured with a UV-visible spectrophotometer (LAMBDA™ 465, PerkinElmer, Inc.). Then, the mRNA concentration was calculated by the following formula.

$$\{[\text{absorbance at 260 nm}]-[\text{absorbance at 350 nm}]\}\times 40\times\text{dilution rate } (\mu g/ml)$$

The results are shown in Table 5.

[Reference Example 1] DNA Vaccine Model

A plasmid for the expression of HPV16 E6-E7 fusion protein was constructed with reference to J. Yan et al., Vaccine 27 (2009) 431-440. As the coding region, the sequence registered under GenBank Accession Number: Fj229356 was used.

TABLE 1

| Example | mRNA | DSPC/Chol/LP/PEG-DMG (mol %) | mRNA Encapsulation Rate | lipid/mRNA (wt/wt) | Mean particle size (nm) |
|---|---|---|---|---|---|
| 8 | Example 1 | 10/43.5/45/1.5 | 97% | 18 | 107 ± 17 |
| 9 | Example 2 | 12.5/41/45/1.5 | 97% | 19 | 102 ± 26 |
| 10 | Example 3 | 12.5/41/45/1.5 | 95% | 21 | 124 ± 18 |
| 11 | Example 4 | 12.5/41/45/1.5 | 96% | 19 | 108 ± 16 |
| 12 | Example 5 | 12.5/41/45/1.5 | 96% | 19 | 111 ± 13 |
| 13 | Example 6 | 12.5/41/45/1.5 | 96% | 20 | 111 ± 14 |
| 14 | Example 2 | 12.5/41/45/1.5 | 94% | 17 | 110 ± 27 |
| 15 | Example 4 | 12.5/41/45/1.5 | 94% | 19 | 111 ± 22 |
| 16 | Example 6 | 12.5/41/45/1.5 | 95% | 18 | 107 ± 21 |
| 17 | Example 7 | 12.5/41/45/1.5 | 94% | 17 | 109 ± 10 |
| 18 | Example 2 | 12.5/41/45/1.5 | 94% | 24 | 120 ± 15 |
| 19 | Example 2 | 12.5/41/45/1.5 | 97% | 29 | 119 ± 11 |
| 20 | Example 2 | 10/43.5/45/1.5 | 97% | 17 | 107 ± 23 |

The results shown in Table 1 clearly reveal that more than 90% of mRNA is encapsulated in lipid particles with mean particle sizes of approximately 100 to 130 nm.

TABLE 2

| Example | mRNA | DSPC/Chol/LP/PEG-C-DMA (mol %) | mRNA Encapsulation Rate | lipid/mRNA (wt/wt) | Mean particle size (nm) |
|---|---|---|---|---|---|
| 21 | OVA | 10/38.5/50/1.5 | 93% | 17 | 116 ± 27 |
| 22 | OVA | 10/35/50/5 | 95% | 14 | 71 ± 4 |
| 23 | OVA | 10/23.5/65/1.5 | 87% | 15 | 147 ± 66 |
| 24 | OVA | 10/48.5/40/1.5 | 79% | 22 | 167 ± 41 |
| 25 | OVA | 5/43.5/50/1.5 | 95% | 19 | 138 ± 46 |
| 26 | OVA | 15/33.5/50/1.5 | 94% | 17 | 112 ± 30 |
| 27 | OVA | 0/53.5/45/1.5 | 97% | 17 | 132 ± 51 |

The results shown in Table 2 clearly reveal that more than 75% of mRNA is encapsulated in lipid particles with mean particle sizes of approximately 70 to 170 nm.

TABLE 3

| Example | mRNA | Phospholipid/Chol/LP/PEG-DMG (mol %) | mRNA Encapsulation Rate | lipid/mRNA (wt/wt) | Mean particle size (nm) |
|---|---|---|---|---|---|
| 28 | Example 4 | 10(DOPC)/43.5/45/1.5 | 97% | 18 | 105 ± 12 |
| 29 | Example 4 | 15(DOPC)/38.5/45/1.5 | 97% | 18 | 99 ± 28 |
| 30 | Example 4 | 10(DOPE)/43.5/45/1.5 | 98% | 21 | 83 ± 20 |
| 31 | Example 4 | 15(DOPE)/38.5/45/1.5 | 98% | 20 | 81 ± 33 |
| 32 | Example 4 | 12.5(DSPC)/41/45/1.5 | 97% | 17 | 102 ± 26 |

The results shown in Table 3 clearly reveal that more than 95% of mRNA is encapsulated in lipid particles with-mean particle sizes of approximately 80 to 110 nm.

TABLE 4

| Example | mRNA | DSPC/Chol/LP/PEG-DMG (mol %) | mRNA Encapsulation Rate | lipid/mRNA (wt/wt) | Mean particle size (nm) |
|---|---|---|---|---|---|
| 37 | Example 33 | 12.5/41/45/1.5 | 99% | 22 | 122 ± 26 |
| 38 | Example 34 | 12.5/41/45/1.5 | 99% | 24 | 104 ± 24 |
| 39 | Example 35 | 12.5/41/45/1.5 | 99% | 20 | 99 ± 25 |
| 40 | Example 36 | 12.5/41/45/1.5 | 99% | 22 | 122 ± 6 |

The results shown in Table 4 clearly reveal that more than 95% of mRNA is encapsulated in lipid particles with mean particle sizes of approximately 90 to 130 nm.

TABLE 5

| Example | mRNA | DSPC/Chol/ LP2/PEG-DMG (mol %) | mRNA Encapsulation Rate | lipid/ mRNA (wt/wt) | Mean particle size (nm) |
|---|---|---|---|---|---|
| 41 | Example 4 | 12.5/41/45/1.5 | 98% | 17 | 101 ± 24 |
| 42 | Example 4 | 17.5/36/45/1.5 | 98% | 17 | 97 ± 29 |
| 43 | Example 4 | 22.5/31/45/1.5 | 99% | 16 | 115 ± 22 |
| 44 | Example 4 | 12.5/33.5/52.5/1.5 | 98% | 16 | 105 ± 33 |
| 45 | Example 4 | 17.5/28.5/52.5/1.5 | 98% | 16 | 102 ± 21 |
| 46 | Example 4 | 22.5/23.5/52.5/1.5 | 98% | 15 | 114 ± 36 |
| 47 | Example 4 | 17.5/28/52.5/2 | 97% | 14 | 110 ± 16 |
| 48 | Example 4 | 17.5/27.5/52.5/2.5 | 98% | 16 | 80 ± 33 |
| 49 | Example 4 | 17.5/27/52.5/3 | 97% | 16 | 71 ± 32 |
| 50 | Example 4 | 12.5/26/60/1.5 | 97% | 16 | 110 ± 46 |
| 51 | Example 4 | 17.5/21/60/1.5 | 98% | 16 | 106 ± 26 |
| 52 | Example 4 | 22.5/16/60/1.5 | 97% | 16 | 102 ± 34 |

The results shown in Table 5 clearly reveal that more than 95% of mRNA is encapsulated in lipid particles with mean particle sizes of approximately 70 to 120 nm.

Test Example 1

Expression Levels of HPV16 E7 Vaccine Antigen in Cultured Cells Transfected with Nucleic Acid Particles Encapsulating mRNA (FIG. 1)

HEK293T cells (human embryonic kidney cell line) were seeded in 96-well plates at $2\times10^4$ cells/well and cultured overnight at 37° C. in an atmosphere of 5% $CO_2$. Subsequently, the nucleic acid lipid particles encapsulating mRNA prepared in Examples 14 to 17 were added respectively to the HEK293T cells at 0.3 to 10 μg/ml as final mRNA concentration. The cells were cultured at 37° C. in an atmosphere of 5% $CO_2$ for 48 hours. After the 96-well plates were left to stand for 1 hour at 4° C., each well was washed 3 times with 300 μl of PBS (−) containing 0.05% Tween 20 (PBST). Subsequently, HPV16 E7 protein (16E7) coated on the wells of the plates was reacted with horse radish peroxidase (HRP)-labeled anti-16E7 antibody at room temperature for 2 hours. After washing the wells 3 times with PBST, HRP substrate was added to the wells for the detection of 16E7. Expression levels of 16E7 protein were calculated by subtracting the absorbance at 540 nm (background absorption) from that at 450 nm in each well.

Test Example 2

Induction Levels of Cytotoxic T Lymphocytes (CTL) Specific to HPV16 E7 Vaccine Antigen (FIGS. 2, 3, 5 and 9

C57BL/6J mice were purchased from CLEA Japan. Every animal experiment was conducted according to the institutional guideline of the National Institute of Biomedical Innovation, Health and Nutrition, Japan. All treatments of animals was conducted under anesthesia by inhalation of isoflurane or by subcutaneous administration of Ketalar/Seractal.

Four to ten microgram mRNA of Nucleic acid lipid particles encapsulating mRNA was inoculated into the gastrocnemius muscle of each 7 week-old C57BL/6 mouse twice 10 days apart. Administration of plasmid DNA into the gastrocnemius muscle was perfumed by electroporation at 40 μg of DNA per mouse. The conditions for the electroporation were as follows: 30 V; 50 ms ON/100 ms OFF; and 3 cycles. Administration by electroporation was also conducted twice 10 days apart. Peripheral blood was collected in the presence of heparin at one week after the final immunization, while the spleen was collected at one or two weeks after the final immunization to prepare peripheral blood mononuclear cells (PBMCs) and splenocytes for evaluation. The induction levels of cytotoxic T lymphocytes (CTL) specific to HPV16 E7 vaccine antigen in PBMCs and splenocytes were measured by FACS through immunostaining with antibodies to T cell surface markers and tetramer complex of 16E7 epitope.

Test Example 3

Figure 4:
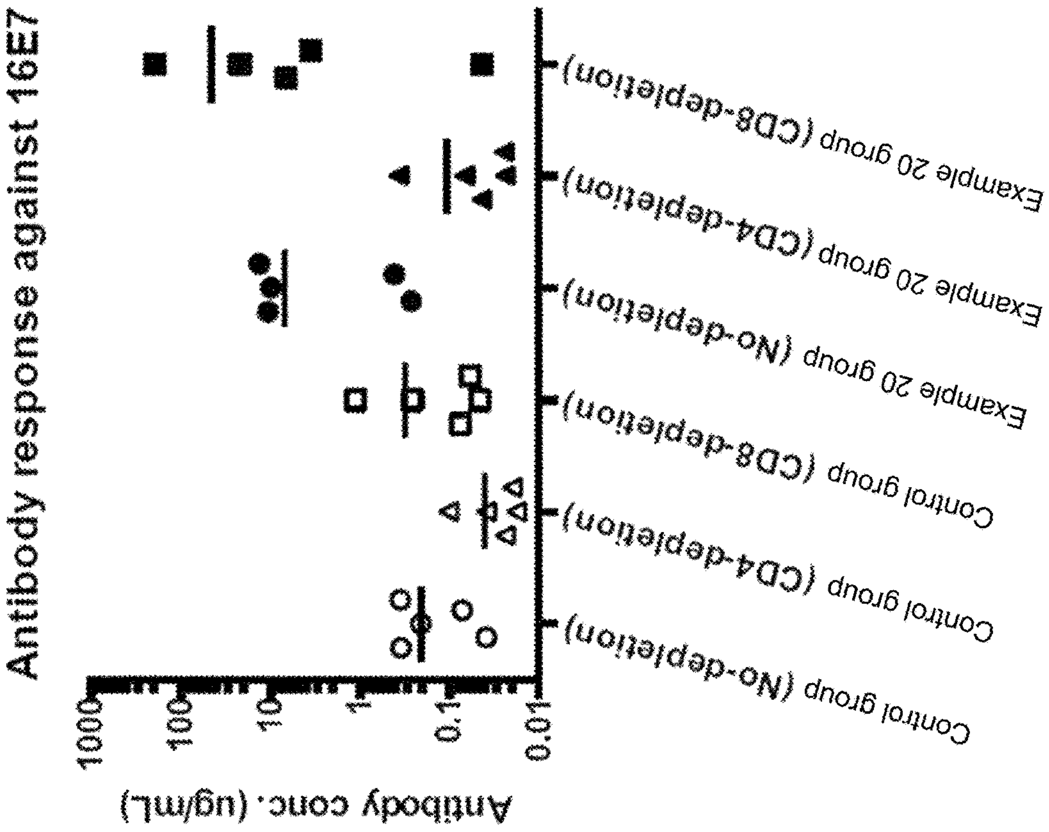
FIG. 4 Antibody responses in mice administered with nucleic acid lipid particles encapsulating mRNA in $CD4^+$ cell- or $CD8^+$ cell-depleted mice. Control groups: mice not administered with nucleic acid lipid particles encapsulating mRNA; Example 20 groups: mice administered with the nucleic acid lipid particles encapsulating mRNA, Example 20. Control group (No-depletion) and Example 20 (No-depletion): mice not administered with depletion antibodies. Control group (CD4 depletion) and Example 20 (CD4 depletion): mice administered with $CD4^+$ cell depletion antibody. Control group (CD8 depletion) and Example 20 (CD8 depletion): mice administered with $CD8^+$ cell depletion antibody.

Measurement of Serum Anti-HPV16 E7 Antibody Titer (FIG. 4)

Ten microgram mRNA of Nucleic acid lipid particles encapsulating mRNA was inoculated into the gastrocnemius muscle of each 7 week-old C57BL/6 mice twice 10 days apart. Peripheral blood was collected in the presence of heparin at one week after the final immunization, and plasma was prepared. Anti-HPV16 E7 IgG titer of plasma was measured by ELISA. ELISA was briefly conducted as followed. The 16E7 recombinant protein was coated on each well of 96-well plates at a concentration of 0.5 μg/ml at 4° C. overnight. Simultaneously, a dilution series of mouse IgG protein for standard curve was also prepared and coated on the same plates. Subsequently, the wells were washed 3 times with PBST and then blocked with 1% BSA-containing PBST (1% BSA/PBST) for 1 hour. Serial dilutions of plasma samples were prepared with 1% BSA/PBST, added to 16E7-immobilized wells, and reacted at room temperature for 2 hours. One percent of BSA in PBST was added to the wells for mouse IgG standard curves and reacted in the same manner. After washing 3 times with PBST, HRP-labeled anti-mouse IgG antibody was added to each well and reacted at room temperature for 1 hour. After washing 3 times with PBST, HRP substrate was added to each well for color development, followed by addition of 1N sulfuric acid solution to terminate the color development. The concentration of mouse IgG bound to 16E7 in each well was calculated using standard curves after subtracting absorbance at 540 nm as a background—from absorbance at 450 nm.

Test Example 4

Figure 5:
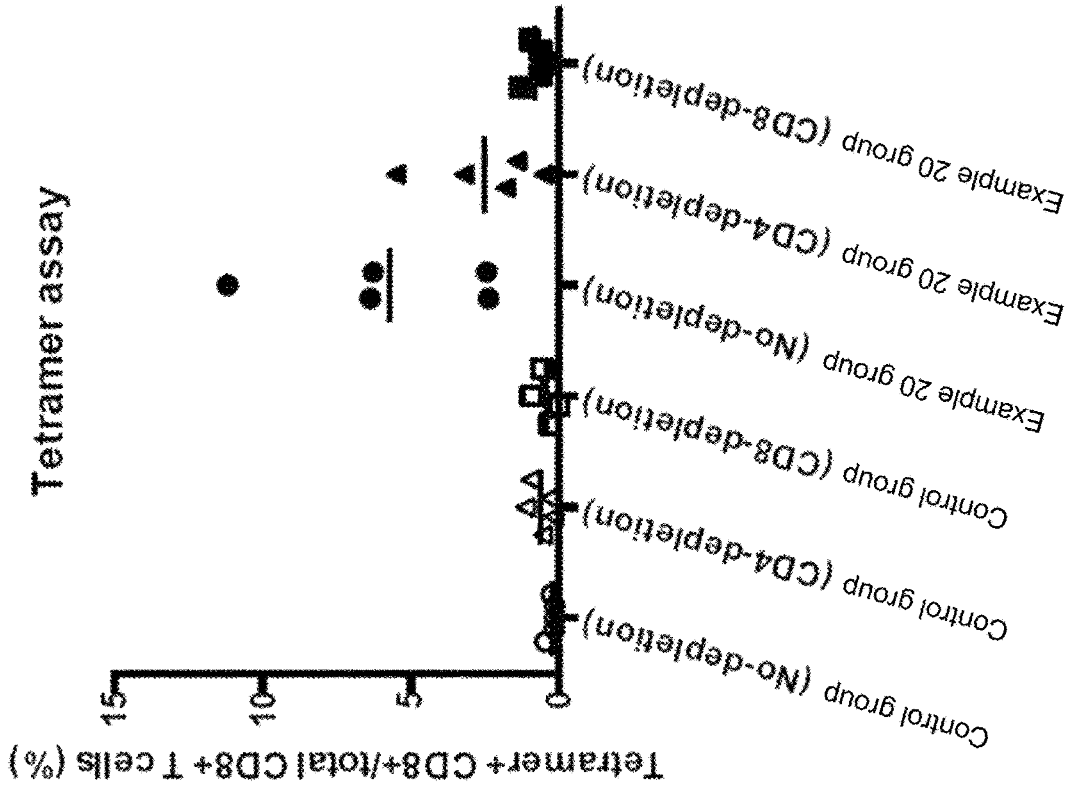
FIG. 5 CTL levels in $CD4^+$ cell and $CD8^+$ cell-depleted mice administered with nucleic acid lipid particles encapsulating mRNA. Control groups: mice not administered with nucleic acid lipid particles encapsulating mRNA; Example 20 groups: mice administered with nucleic acid lipid particles encapsulating mRNA, Example 20. Control group (No-depletion) and Example 20 (No-depletion): mice not administered with depletion antibodies. Control group (CD4 depletion) and Example 20 (CD4 depletion): mice administered with $CD4^+$ cell depletion antibody. Control group (CD8 depletion) and Example 20 (CD8 depletion): mice administered with $CD8^+$ cell depletion antibody.
Figure 6:
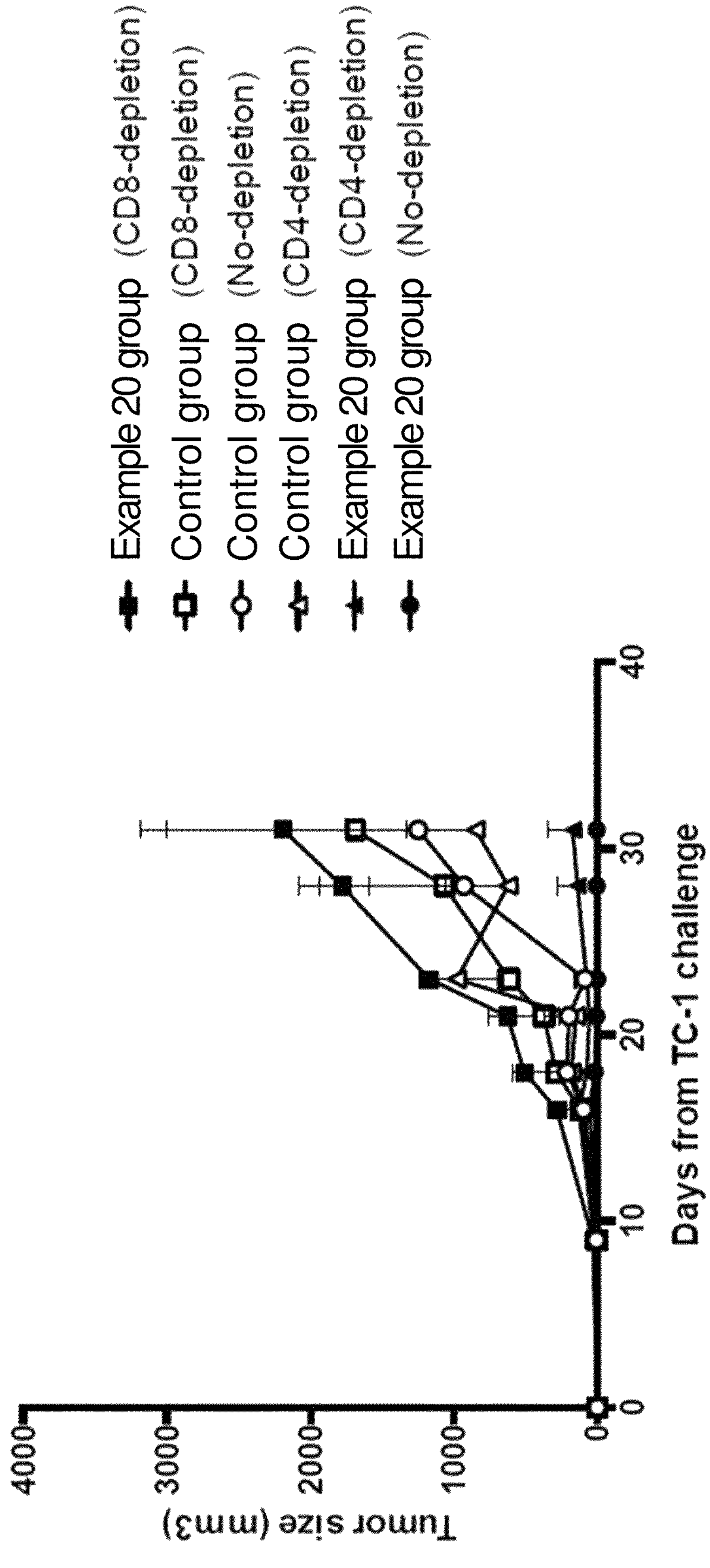
FIG. 6 Anti-tumor effect of nucleic acid lipid particles encapsulating mRNA in the model of mice transplanted with TC-1 cells. Control groups: mice not administered with nucleic acid lipid particles encapsulating mRNA; Example 20 groups: mice administered with nucleic acid lipid particles encapsulating mRNA, Example 20. Control group (No-depletion) and Example 20 (No-depletion): mice not administered with depletion antibodies. Control group (CD4 depletion) and Example 20 (CD4 depletion): mice administered with $CD4^+$ cell depletion antibody. Control group (CD8 depletion) and Example 20 (CD8 depletion): mice administered with $CD8^+$ cell depletion antibody. Tumor size is represented by volume, i.e., tumor length (mm)×tumor width (mm)×tumor height (mm).

Regression of TC-1 Tumour Cell Growth in C57BL/6 Mice Administered with Nucleic Acid Lipid Particles Encapsulating mRNA (FIGS. 4 to 6)

TC-1 cells which was established from lung epithelial cells of C57BL/6 mice and express HPV16 E6 and E7 were transplanted subcutaneously to the lateral abdomen of C57BL/6 mice, and tumor size was measured over time. The transplantation site was shaved prior to transplantation of TC-1 cells, and $1\times10^5$ of TC-1 cells were transplanted into each mouse. Ten microgram mRNA of the nucleic acid lipid particles encapsulating the mRNA of Example 20 was administered intramuscularly into each mouse at 8 days after-the transplantation of TC-1 cells. Administration of antibodies to deplete CD4 positive cells or CD8 positive cells was conducted at 2 days before the administration of the nucleic acid lipid particles encapsulating mRNA.

Test Example 5

Depletion of CD4 Positive or CD8 Positive Cells by Administration of Anti-CD4 Antibody and Anti-CD8 Antibody (FIGS. 4 to 6)

A hundred microgram of anti-CD4 antibody (GK1.5) or anti-CD8 antibody (53-6.72) were administered intraperitoneally to each 7 week-old C57BL/6 mice for 3 consecutive days at 2 days before the administration of nucleic acid lipid particles encapsulating mRNA. At 3 days after antibody administration, 10 μg mRNA of the nucleic acid lipid particles encapsulating mRNA from Example 20 was administered into the gastrocnemius muscle of each mouse.

Test Example 6

Figure 7:
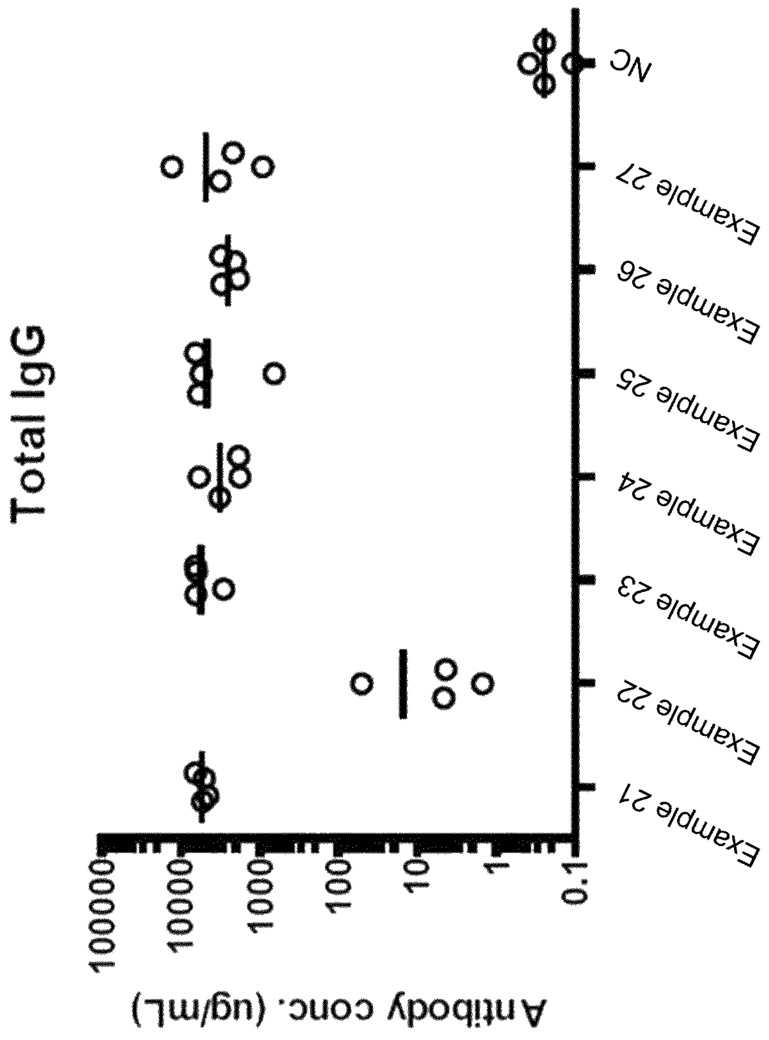
FIG. 7 Anti-OVA antibody responses in C57BL/6 mice administered with nucleic acid lipid particles encapsulating mRNA. Examples 21-27: mice administered with nucleic acid lipid particles encapsulating mRNA. NC: untreated negative control group.

Measurement of Anti-OVA Antibody Titer (FIG. 7)

Fifteen microgram mRNA of Nucleic acid lipid particles encapsulating mRNA was administered subcutaneously to the tail base of each 7 week-old C57BL/6 mouse 2 weeks apart. One week after the final immunization, peripheral blood was collected and serum was prepared. Anti-OVA IgG titer in plasma was measured by ELISA. ELISA was briefly conducted as followed. OVA recombinant protein was coated at a concentration of 1 μg/ml on each well of 96-well plates at 4° C. overnight. Simultaneously, a dilution series of mouse IgG protein was also coated on the same plates for standard curves. Subsequently, the wells were washed 3 times with PBST and then blocked with 1% BSA-containing PBST (1% BSA/PBST) for 1 hour. Serial dilutions of serum samples were prepared with 1% BSA/PBST, were added to OVA-immobilized wells, and were reacted at room temperature for 2 hours. One percent of BSA in PBST was added to the wells for mouse IgG standard curves and reacted in the same manner. After washing with PBST 3 times, HRP-labeled anti-mouse IgG antibody was added to each well and reacted at room temperature for 1 hour. After washing with PBST 3 times, HRP substrate was added to each well for color development, followed by addition of 1N sulfuric acid solution to terminate the color development. The concentration of mouse anti-OVA IgG titer in each well was calculated using standard curves after subtracting absorbance at 540 nm as a background from absorbance at 450 nm.

Test Example 7

Figure 8:
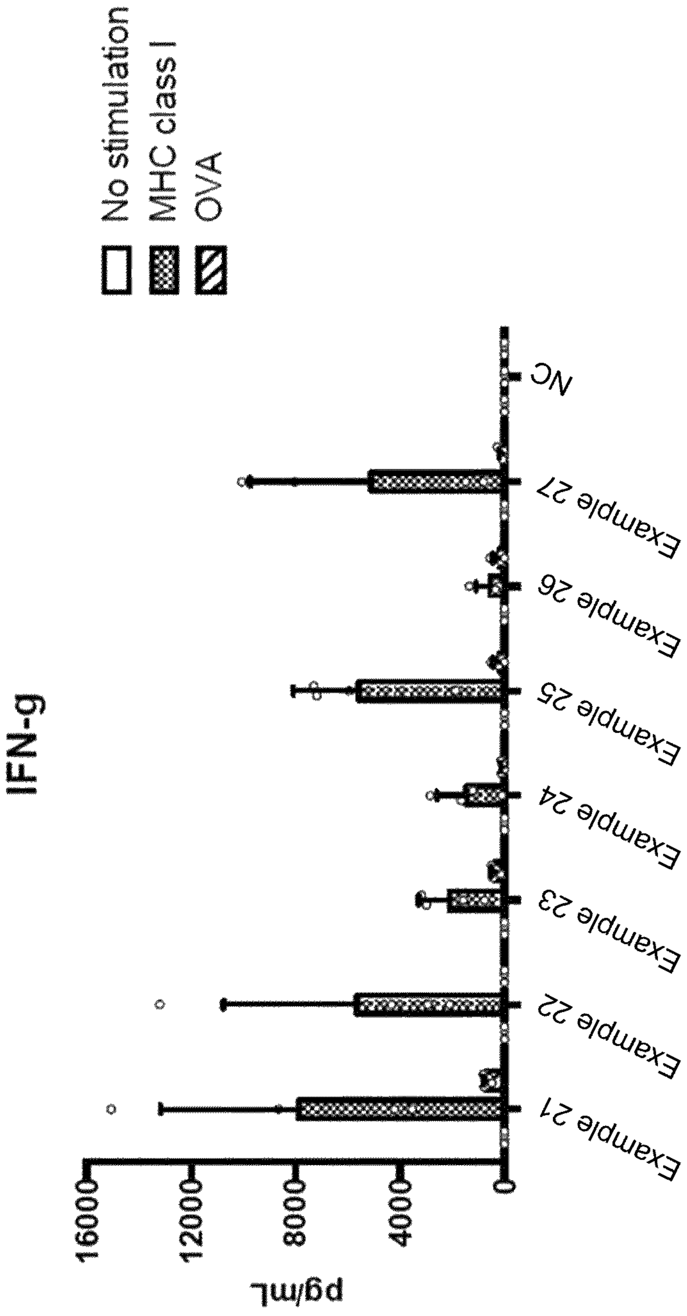
FIG. 8 OVA-specific IFN-γ production from splenocytes of C57BL/6 mice administered with nucleic acid lipid particles encapsulating mRNA. Examples 21-27: mice administered with nucleic acid lipid particles encapsulating mRNA; NC: untreated negative control group. No-stimulation: negative control group without any stimulation; MHC class I: stimulation with the epitope peptide restricted by MHC class I of C57BL/6 mice; OVA: stimulation with OVA protein.

OVA-Specific Cytokine Production from T Cells (FIG. 8)

Fifteen microgram mRNA of Nucleic acid lipid particles encapsulating mRNA was administered subcutaneously to the tail base of each 7 week-old C57BL/6 mouse twice 2 weeks apart. One week after the final immunization, the spleen was collected and splenocytes were prepared. Splenocytes were seeded in 96-well culture plates, were stimulated with MHC class I-restricted epitope peptide of OVA antigen or with OVA protein, and then were cultured for 24 hours. The IFN-γ level in culture supernatant was measured by cytokine ELISA.

Test Example 8

Figure 10:
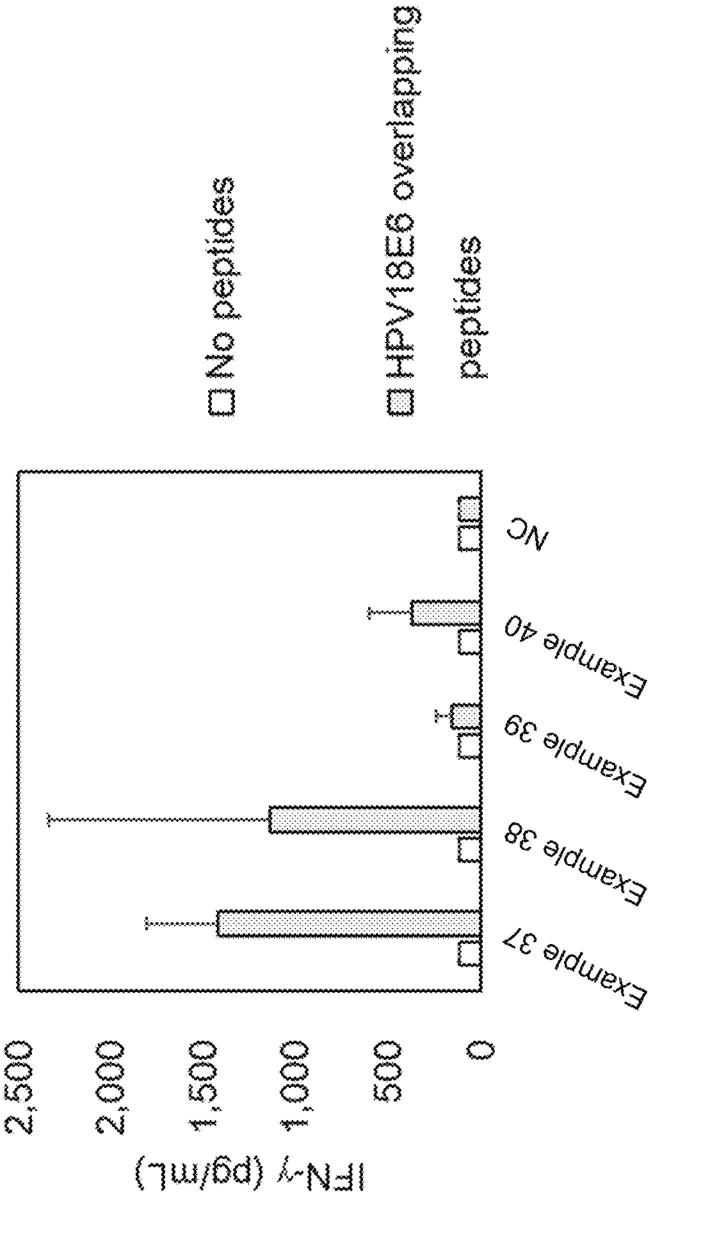

HPV18E6- or HPV18E7-Specific Cytokine Production from T Cells (FIG. 10)

C57BL/6J mice were purchased from CLEA Japan. Every treatment of animals was conducted under anesthesia by inhalation of isoflurane.

Five microgram mRNA of Nucleic acid lipid particles encapsulating mRNA was administered into the gastrocnemius muscle of each 6 week-old C57BL/6 mouse twice 2 weeks apart. One week after the final immunization, the spleen was collected and splenocytes were prepared. Splenocytes were treated with HPV18 E6 pool peptide (JPT Peptide Technologies, catalog #PM-HPV18-E6). IFN-γ level in culture supernatant after 48-hour culture was measured by cytokine ELISA.

Test Example 9

Figure 11:
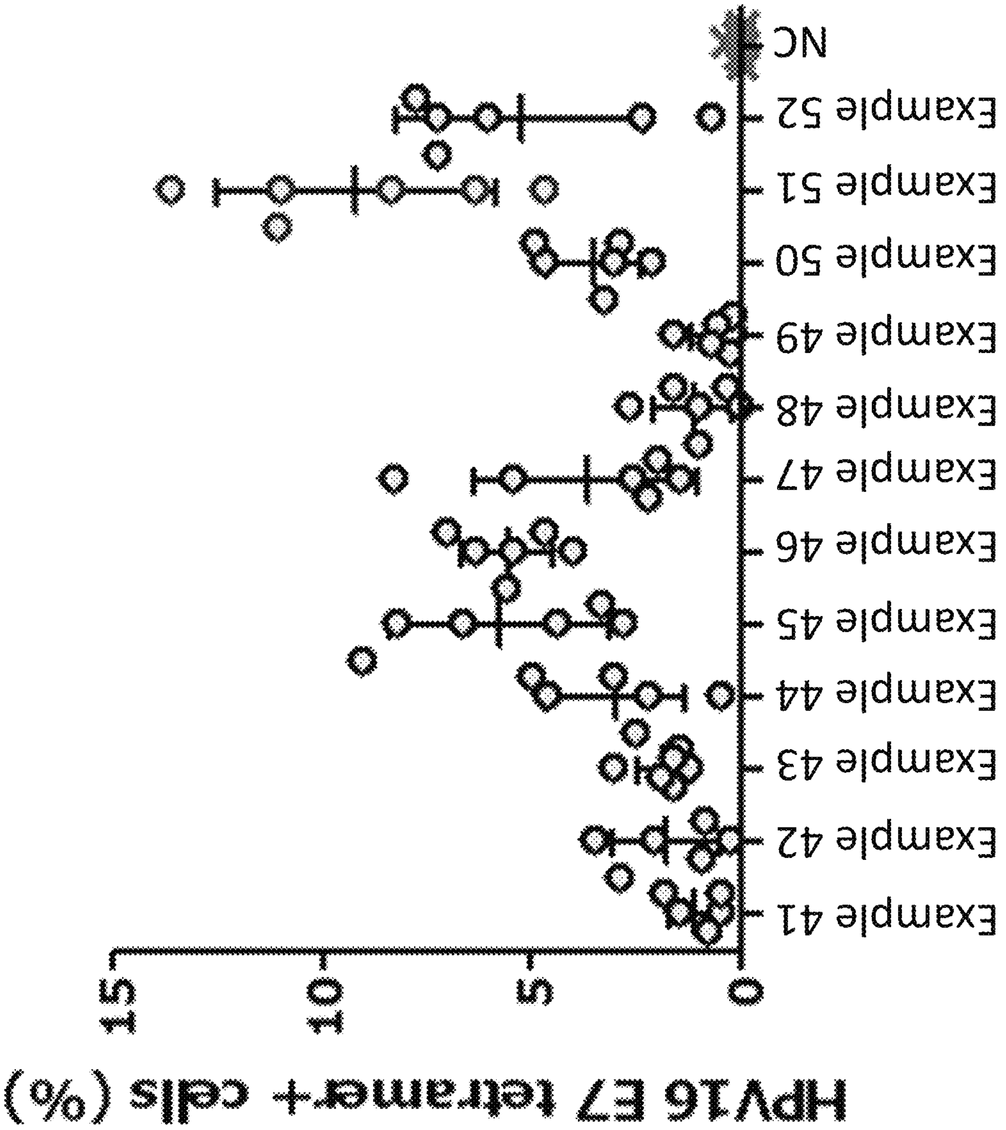
FIG. 11 CTL levels in C57BL/6 mice administered with nucleic acid lipid particles encapsulating mRNA. Examples 41-52: mice administered with nucleic acid lipid particles encapsulating mRNA; NC: negative control mice administered with buffer.

The Levels of Cytotoxic T Lymphocytes (CTL) Specific to HPV16 E6 or E7 Antigen (FIG. 11)

C57BL/6J mice were purchased from CLEA Japan. Every treatment of animals was conducted under anesthesia by inhalation of isoflurane.

Five microgram mRNA of Nucleic acid lipid particles encapsulating mRNA was administered into the gastrocnemius muscle of each 6 week-old C57BL/6J mouse twice 2 weeks apart. One week after the final immunization, the spleen was collected and splenocytes were prepared. The levels CTL specific to E7 of HPV16 genotype (HPV16E7) in splenocytes were measured by flow cytometry through the immunostaining with antibodies to T lymphocyte surface markers and complex of MHC class I with HPV16E7 epitope.

Test Example 10

Figure 12:
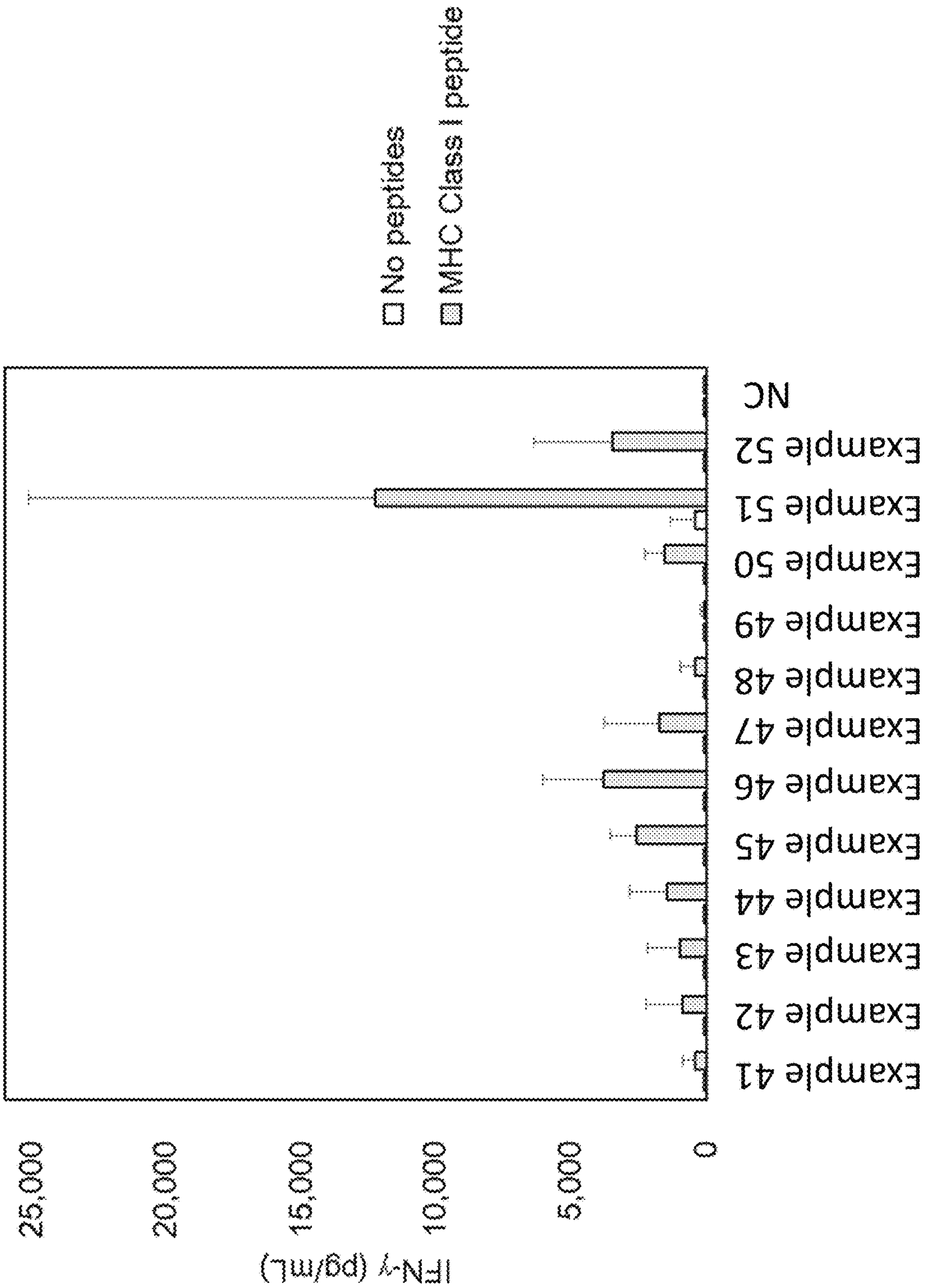
FIG. 12 HPV16E7-specific IFN-γ production from splenocytes of C57BL/6 mice administered with nucleic acid lipid particles encapsulating mRNA. Examples 41-52: mice administered with nucleic acid lipid particles encapsulating mRNA; NC: negative control mice administered with buffer. No peptides: negative control groups stimulated with no peptides; MHC class I peptide: groups stimulated with the HPV16E7 epitope peptide restricted by MHC class I of C57BL/6 mice.

HPV16 E6- or E7-Specific Cytokine Production from T Cells (FIG. 12)

Five microgram mRNA of Nucleic acid lipid particles encapsulating mRNA was administered into the gastrocnemius muscle of each 6 week-old C57BL/6J mouse twice 2 weeks apart. One week after the final immunization, the spleen was collected and splenocytes were prepared. Splenocytes were seeded in 96-well culture plates and cultured for 24 hours under the treatment with MHC class I-restricted epitope peptide of HPV16E7. Subsequently, IFN-γ levels in the culture supernatant was measured by cytokine ELISA.

Results of Test Examples 1 to 10

Expression Levels of HPV16 E7 from HEK293T Cells Transfected with Nucleic Lipid Particles Encapsulating mRNA of Examples 14 to 17 (FIG. 1)

HPV16 E7 expression levels from HEK293T cells transfected with nucleic lipid particles encapsulating mRNA in cultured cells were evaluated. The results are shown in FIG. 1. Expression levels of the E7 protein of HPV16 (16E7) are higher in the cells transfected with the particles of Examples 15 and 16 than in those of Examples 14 and 17. When compared with those cells transfected with no nucleic lipid particles encapsulating mRNA, any of the cells transfected with the lipid particles of these Examples showed higher HPV16E7 expressions, indicating clearly the protein expression capacity of nucleic acid lipid particles encapsulating mRNA in cultured cells.

Figure 2:
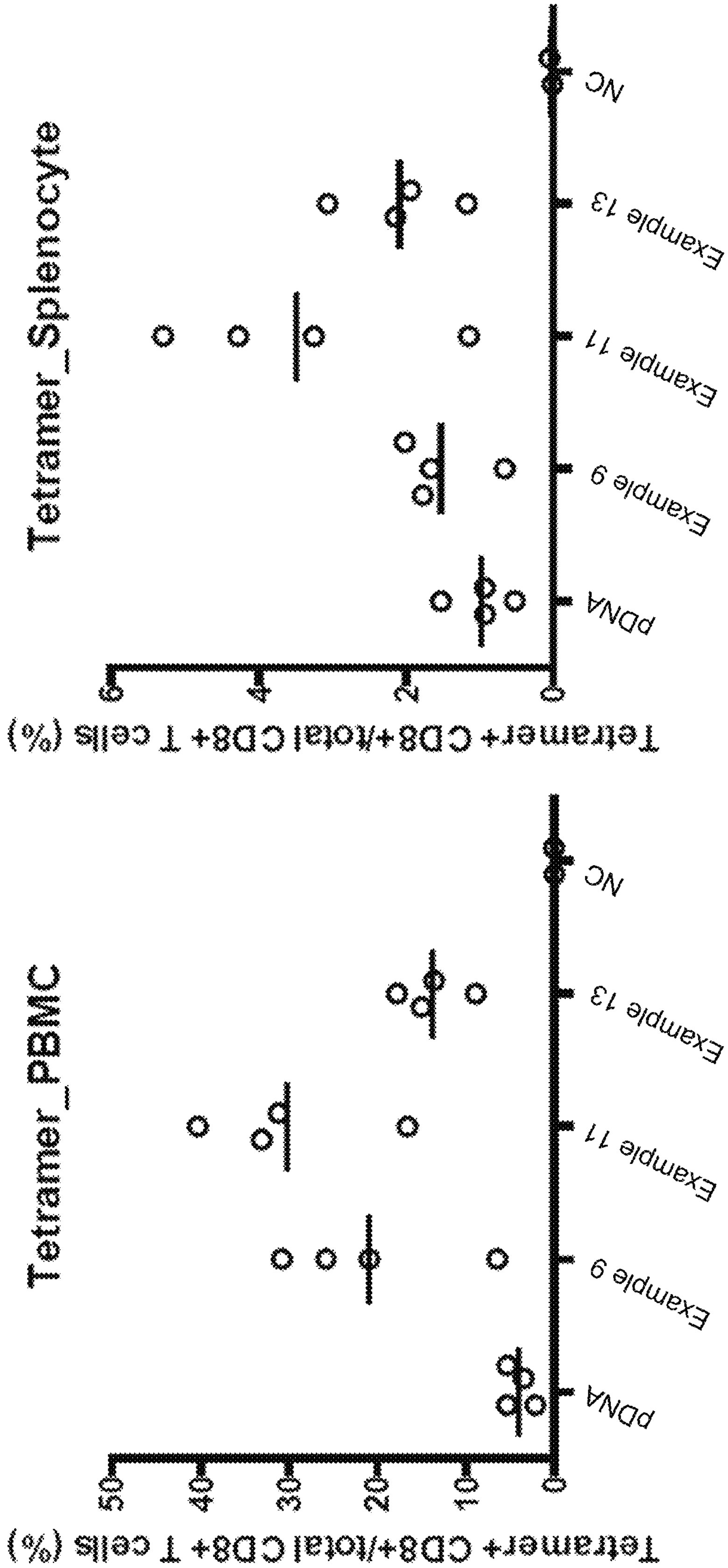
FIG. 2 CTL levels in C57BL/6 mice administered with DNA vaccines or nucleic acid lipid particles encapsulating mRNA. pDNA: mice administered with the DNA vaccine of Reference Example 1. Examples 9, 11 and 13: mice administered with nucleic acid lipid particles encapsulating mRNA. NC: untreated negative control group. PBMC: peripheral blood mononuclear cells. Splenocyte: spleen cells.

Comparison of CTL Levels Between the DNA Vaccine and Nucleic Acid Lipid Particles Encapsulating mRNA (FIG. 2)

Construction of the DNA vaccine is described in Reference Example 1. The levels of CTL specific to HPV16E7 in mice administered with the DNA vaccine or the nucleic acid lipid particles encapsulating mRNA of Examples 9, 11 and 13 were evaluated. The results are shown in FIG. 2. When the levels of CTL specific to 16E7 in peripheral blood were evaluated one week after the final immunization, all the three types of nucleic acid lipid particles encapsulating mRNA exhibited higher CTL levels than the DNA vaccine model (pDNA) (see left panel). Further, when the levels of CTL specific to 16E7 in splenocytes were evaluated at 2 weeks after the final immunization, the nucleic acid lipid particles encapsulating mRNA of Examples 9, 11 and 13 exhibited a CTL induction level equivalent to or higher than that of pDNA (see right panel).

Figure 3:
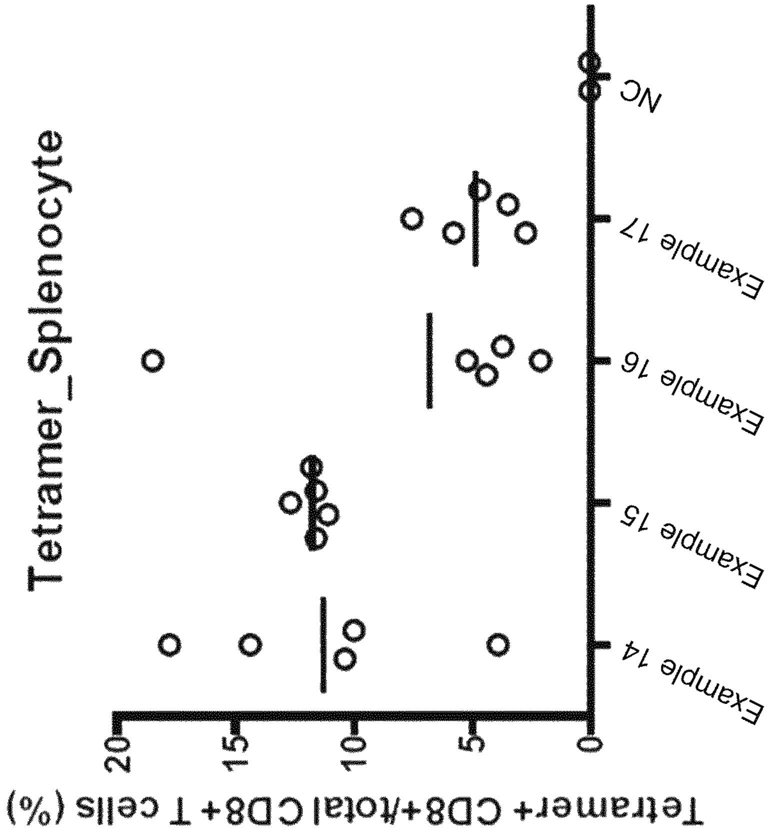
FIG. 3 CTL levels in C57BL/6 mice administered with nucleic acid lipid particles encapsulating mRNA. Examples 14-17: mice administered with nucleic acid lipid particles encapsulating mRNA. NC: untreated negative control group. Splenocyte: spleen cells.

The CTL Levels in Mice Administered with Nucleic Acid Lipid Particles Encapsulating mRNA of Examples 14 to 17 (FIG. 3)

16E7-specific CTL levels in C57BL/6 mice administered with four types of nucleic acid lipid particles encapsulating mRNA were examined. The results are shown in FIG. 3. The 16E7-specific CTL levels was detected in mice administered with all the four types of nucleic acid lipid particles encapsulating mRNA.

Importance of CD4 Positive Cells but not CD8 Positive Cells for the Antibody Responses in Mice Administered with Nucleic Acid Lipid Particles Encapsulating mRNA (FIG. 4)

Antibody responses were examined in mice administered with nucleic acid lipid particles encapsulating mRNA under depletion of CD4 positive cells or CD8 positive cells after transplantation of TC-1 tumor cells. The results are shown in FIG. 4. While less antibody responses were detected in the mice without treatments for depletion of CD4- or CD8-positive cells (control (No-depletion) group), those mice administered with the nucleic acid lipid particles encapsulating mRNA of Example 20 (Example 20 (No-depletion) group) showed a considerable anti-HPV16E7 antibody responses. Further, when CD8 positive cells-depleted mice were administered with nucleic acid lipid particles encapsulating mRNA of Example 20 (Example 20 (CD8-depletion) group), the mice also showed antibody responses equivalent to that of the Example 20 (No-depletion) mice. However, when CD4 positive cells-depleted mice were administered with nucleic acid lipid particles encapsulating mRNA (Example 20 (CD4-depletion) group), anti-16E7 antibody response in those mice was clearly reduced compared with those of the Example 20 (No-depletion) and Example 20 (CD8-depletion) groups. These results suggested that CD4 positive cells are important for the anti-HPV16E7 antibody responses in mice administered with the nucleic acid lipid particles encapsulating mRNA.

Importance of CD4 Positive Cells and CD8 Positive Cells for the CTL Induction in Mice Administered with Nucleic Acid Lipid Particles Encapsulating mRNA (FIG. 5)

The levels of CTL specific to 16E7 in mice administered with nucleic acid lipid particles encapsulating mRNA were examined under depletion of CD4 positive cells or CD8 positive cells after transplantation of TC-1 tumor cells. The results are shown in FIG. 5. While less HPV16E7-specific CTL responses were detected in the mice without treatments for depletion of CD4- or CD8-positive cells (control (No-depletion) group), those mice administered with nucleic acid lipid particles encapsulating mRNA of Example 20 (Example 20 (No-depletion) group) showed a considerable HPV16E7-CTL induction. Further, when CD4 positive cells-depleted mice were administered with nucleic acid lipid particles encapsulating mRNA of Example 20 (Example 20 (CD4-depletion) group), the mice also showed slight lower CTL induction than that of the Example 20 (No-depletion) mice. However, when CD8 positive cells-depleted mice were administered with nucleic acid lipid particles encapsulating mRNA (Example 20 (CD8-depletion) group), HPV16E7-specific CTL induction in those mice was clearly reduced compared with those of the Example 20 (No-depletion) and Example 20 (CD4-depletion) groups. These results suggested that CD8 positive cells are important for the HPV16E7-specific CTL induction in mice administered with nucleic acid lipid particles encapsulating mRNA.

Importance of CD4 Positive Cells and CD8 Positive Cells for TC-1 Tumor Regression Effect in Mice Administered with Nucleic Acid Lipid Particles Encapsulating mRNA (FIG. 6)

TC-1 tumor regression effect in mice administered with nucleic acid lipid particles encapsulating mRNA were examined under depletion of CD4 positive cells or CD8 positive cells after transplantation of TC-1 tumor cells. The results are shown in FIG. 6. While less tumor regression effect were detected in the mice without treatments for depletion of CD4- or CD8-positive cells (control (No-depletion) group), those mice administered with nucleic acid lipid particles encapsulating mRNA of Example 20 (Example 20 (No-depletion) group) showed strong tumor regression effect. Further, when CD4 positive cells-depleted mice were administered with nucleic acid lipid particles encapsulating mRNA of Example 20 (Example 20 (CD4-depletion) group), the mice also showed tumor regression effect equivalent to that of the Example 20 (No-depletion) mice. However, when CD8 positive cells-depleted mice were administered with nucleic acid lipid particles encapsulating mRNA (Example 20 (CD8-depletion) group), tumor regression effect in those mice was clearly reduced compared with those of the Example 20 (No-depletion) and Example 20 (CD4-depletion) groups. These results suggested that CD8 positive cells are important for TC-1 tumor regression effect in mice administered with nucleic acid lipid particles encapsulating mRNA.

Anti-OVA Antibody Responses in Mice Administered with by Nucleic Acid Lipid Particles Encapsulating mRNA of Examples 21 to 27 with Different Lipid Compositions (FIG. 7)

The nucleic acid lipid particles encapsulating mRNA of Examples 21 to 27 were administered intramuscularly to C57BL/6 mice. One week after the final immunization, anti-OVA antibody responses in blood were examined. The results are shown in FIG. 7. The anti-OVA antibody responses was low in mice administered with nucleic acid lipid particles encapsulating mRNA of Example 22, whereas the antibody levels were equivalent among the mice administered with the other Examples.

OVA-Specific IFN-γProduction from Splenocytes of Mice Administered with Nucleic Acid Lipid Particles Encapsulating mRNA of Examples 21 to 27 with Different Lipid Compositions (FIG. 8)

The nucleic acid lipid particles encapsulating mRNA of Examples 21 to 27 were administered intramuscularly to C57BL/6 mice. One week after the final immunization, levels of OVA-specific-cytokines from splenocytes were examined. The results are shown in FIG. 8. In the mice administered with the nucleic acid lipid particles encapsulating mRNA of Example 26, the levels of IFN-γ specific to MHC class I restricted epitope peptide of OVA and OVA protein were the lowest among the Examples, whereas the OVA-specific IFN-γ levels in the mice administered with the nucleic acid lipid particles encapsulating mRNA of Examples 21, 22, 25, and 27 were equivalent.

Figure 9:
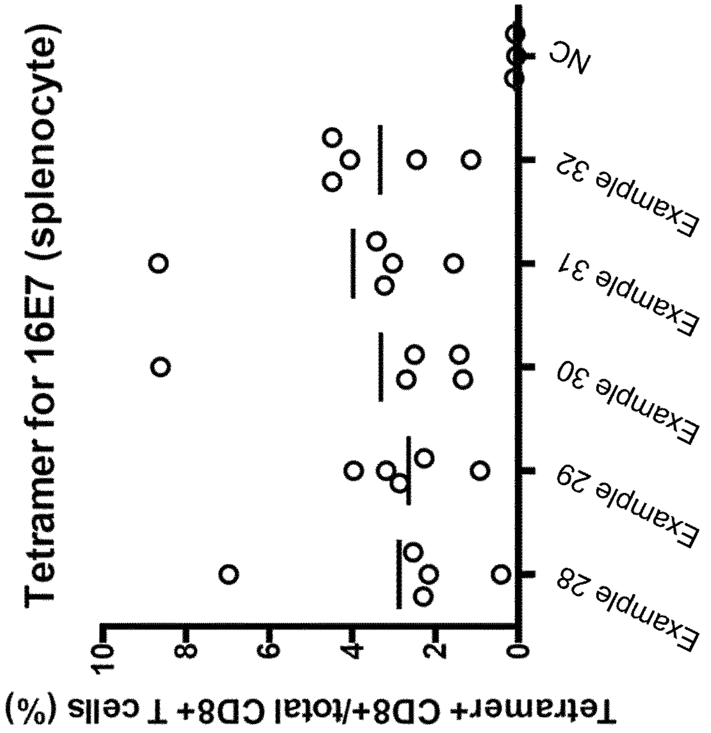
FIG. 9 CTL levels in C57BL/6 mice administered with nucleic acid lipid particles encapsulating mRNA. Examples 28-32: mice administered with nucleic acid lipid particles encapsulating mRNA; NC: untreated negative control group. Splenocyte: spleen cells FIG. 10 HPV18E6-specific IFN-γ production from splenocytes of C57BL/6 mice administered with nucleic acid lipid particles encapsulating mRNA. Examples 37-40: mice administered with nucleic acid lipid particles encapsulating mRNA; NC: negative control mice administered with buffer. No peptides: negative control groups stimulated with no peptides; HPV18E6 overlapping peptides: groups stimulated with HPV18E6 pool peptides.

CTL Levels in Mice Administered with Nucleic Acid Lipid Particles Encapsulating mRNA of Examples 28 to 32 with Different Phospholipid Species and its Content (FIG. 9)

The levels of HPV16E7-specific CTL in C57BL/6 mice administered with five types of nucleic acid lipid particles encapsulating mRNA were examined. The results are shown in FIG. 9. The levels of HPV16E7-specific CTL were equivalent among Examples 28 and 29 with DOPC used as a phospholipid, Examples of 30 and 31 with DOPE used as a phospholipid, and Example 32 with DSPC used as a phospholipid.

HPV18E6-Specific Cytokine Production from Splenocytes in Mice Administered with Nucleic Acid Lipid Particles Encapsulating mRNA of Examples 37 to 40 with Different mRNA Modification (FIG. 10)

Nucleic acid lipid particles encapsulating mRNA of Examples 37 to 40 were administered intramuscularly to C57BL/6 mice. One week after the final immunization, the levels of HPV18 E6-specific T cell cytokine production from splenocytes were examined. The results are shown in FIG. 10. The production of IFN-γ was observed in mice administered with nucleic acid lipid particles encapsulating mRNA of Examples 37 to 40, compared with the NC group, when treated with HPV18 E6 pool peptide (FIG. 10).

CTL Levels in Mice Administered with of Nucleic Acid Lipid Particles Encapsulating mRNA of Examples 41 to 52 with Different Lipid Composition Ratios (FIG. 11)

Nucleic acid lipid particles encapsulating mRNA of Examples 41 to 52 were administered intramuscularly to C57BL/6 mice. One week after the final immunization, the levels of HPV16E7-specific CTL in splenocytes were evaluated. The results are shown in FIG. 11. The levels of HPV16E7-specific CTL were higher in all mice administered with the nucleic acid lipid particles encapsulating mRNA, compared with the NC group.

HPV16E7-Specific IFN-γ Production from Splenocytes of Mice Administered with Nucleic Acid Lipid Particles Encapsulating mRNA of Examples 41 to 52 with Different Lipid Composition Ratios (FIG. 12)

Nucleic acid lipid particles encapsulating mRNA of Examples 41 to 52 were administered intramuscularly to C57BL/6 mice. One week after the final immunization, levels of HPV16 E7-specific T cell cytokine production from splenocytes were examined. The results are shown in FIG. 12. In any mice administered with nucleic acid lipid particles encapsulating mRNA, IFN-γ production specific to MHC class I restricted HPV16E7 epitope peptide was induced, compared with the NC group.

All publications, patents and patent applications cited herein are incorporated herein by reference in their entirety.

INDUSTRIAL APPLICABILITY

The present invention is applicable to prevention and/or treatment of infections with human papillomavirus.

```
SEQUENCE LISTING FREE TEXT
<SEQ ID NO: 1> Template DNA for IVT of HPV16 E6-E7 fusion2.
GCTAGC (NheI site): nucleotide numbers 1-6
T7 promoter sequence: nucleotide numbers 8-27
5'-UTR sequence of human β-globin: nucleotide numbers 39-88
KOZAK sequence: nucleotide numbers 89-94
Coding region of IgE leader sequence: nucleotide numbers 95-148
Coding region of HPV16 E6: nucleotide numbers 149-598
Furin cleavage site: nucleotide numbers 599-619
Coding region of HPV16 E7: nucleotide numbers 620-913
3'-UTR sequence of human β-globin: nucleotide numbers 914-1045
PoylA: nucleotide numbers 1046-1147
ACTAGT (SpeI site): nucleotide numbers 1152-1157
gctagcgtaatacgactcactataaggagacccaagctacatttgcttctgacacaactgtgttcac

tagcaacctcaaacagacaccgccaccatggactggacctggatcctgtttctggtggccgctgcca

cacgggtgcacagctttcaggaccctcaagagaggcccagaaagctgcctcagctgtgtaccgagct

gcagaccaccatccacgacatcatcctggaatgcgtgtactgcaagcagcagctcctgcggagagag

gtgtacgatttcgccttccgggacctgtgcatcgtgtacagagatggcaacccctacgccgtgtgcg

acaagggcctgaagttctacagcaagatcagcgagtaccggcactactgctacagcctgtacggcac

cacactggaacagcagtacaacaagcccctgtgcgacctgctgatccggtgcatcaactgccagaaa

cctctgtgccccgaggaaaagcagcggcacctggacaagaagcagcggttccacaacatcagaggcc

ggtggacaggcagaggcatgagctgttgtcggagcagccggaccagaagagaaacccagctgagagg

ccggaagagaagaagccacggcgatacccctacactgcacgagtacatgctggacctgcagcctgag

acaaccgatctgtacggctacggccagctgaacgacagctctgaggaagaggacgagatcgacggac

ctgctggacaggccgaacctgatagagcccactacaatatcgtgaccttctgctgcaagtgcgacag

caccctgagactgtgtgtgcagagcacccacgtggacatcagaaccctggaagatctgctgatgggc

accctgggaatcgtgggccctatctgtagccagaagccttgagctcgctttcttgctgtccaatttc

tattaaaggttcctttgttccctaagtccaactactaaactgggggatattatgaagggccttgagc

atctggattctgcctaataaaaaacatttattttcattgcaaaaaaaaaaaaaaaaaaaa

aaaaaaaaaaaaaaaaaaaaaaaaaaaaaaaaaaaaaaaaaaaaaaaaaaaaaaaaaaaa

aaaaaaagagcactagt
```

-continued

<SEQ ID NO: 2> HPV16 E6-E7 fusion2 mRNA-001
aggagacccaagcuacauuugcuucugacacaacuguguucacuagcaaccucaaacagacaccgcc accauggacuggaccuggauccuguuucugguggccgcugccacacgggugcacagcuuucaggacc cucaagagaggcccagaaagcugccucagcuguguaccgagcugcagaccaccauccacgacaucau ccuggaaugcguguacugcaagcagcagcuccugcggagagagguguacgauuucgccuuccgggac cugugcaucguguacagagauggcaaccccuacgccgugugcgacaagggccugaaguucuacagca agaucagcgaguaccggcacuacugcuacagccuguacggcaccacacuggaacagcaguacaacaa gccccugugcgaccugcugauccggugcaucaacugccagaaaccucugugccccgaggaaaagcag cggcaccuggacaagaagcagcgguuccacaacaucagaggccgguggacaggcagaggcaugagcu guugucggagcagccggaccagaagagaaacccagcugagaggccggaagagaagaagccacggcga uaccccuacacugcacgaguacaugcuggaccugcagccugagacaaccgaucuguacggcuacggc cagcugaacgacagcucugaggaagaggacgagaucgacggaccugcuggacaggccgaaccugaua gagcccacuacaauaucgugaccuucugcugcaagugcgacagcacccugagacugugugugcagag cacccacguggacaucagaacccuggaagaucugcugaugggcacccugggaaucgugggcccuauc uguagccagaagccuugagcucgcuuucuugcuguccaauuucuauuaaagguuccuuuguucccua aguccaacuacuaaacugggggauauuaugaagggccuugagcaucuggauucugccuaauaaaaaa cauuuauuuucauugcaaaaaaaaaaaaaaaaaaaaaaaaaaaaaaaaaaaaaaaaaaaa aaaaaaaaaaaaaaaaaaaaaaaaaaaaaaaaaaaaaaaaaaaaagagcacuag <SEQ ID NO: 3> Template DNA for IVT of HPV16 E6-E7 fusion10.
GCTAGC (NheI site): nucleotide numbers 1-6
T7 promoter sequence: nucleotide numbers 8-27
5'-UTR sequence of human β-globin: nucleotide numbers 39-88
KOZAK sequence: nucleotide numbers 89-94
Coding region of IgE leader sequence: nucleotide numbers 95-148
Coding region of HPV16 E6: nucleotide numbers 149-598
Furin cleavage site: nucleotide numbers 599-619
Coding region of HPV16 E7: nucleotide numbers 620-913
3'-UTR sequence of human β-globin: nucleotide numbers 914-1045
PoylA: nucleotide numbers 1046-1147
ACTAGT (SpeI site): nucleotide numbers 1152-1157
gctagcgtaatacgactcactataaggagacccaagctacatttgcttctgacacaactgtgttcac tagcaacctcaaacagacaccgccaccatggactggacctggatcctgttcctggtggccgccgcca cacgggtgcacagcttccaggacccccaagagaggcccagaaagctgccccagctgtgcaccgagct gcagaccaccatccacgacatcatcctggaatgcgtgtactgcaagcagcagctcctgcggagagag gtgtacgacttcgccttccgggacctgtgcatcgtgtacagagacggcaacccctacgccgtgtgcg acaagggcctgaagttctacagcaagatcagcgagtaccggcactactgctacagcctgtacggcac cacactggaacagcagtacaacaagcccctgtgcgacctgctgatccggtgcatcaactgccagaaa cccctgtgccccgaggaaaagcagcggcacctggacaagaagcagcggttccacaacatcagaggcc ggtggacaggcagaggcatgagctgctgccggagcagccggaccagaagagaaacccagctgagagg ccggaagagaagaagccacggcgacacccccacactgcacgagtacatgctggacctgcagcccgag acaaccgacctgtacggctacggccagctgaacgacagcagcgaggaagaggacgagatcgacggac ccgccggacaggccgaacccgacagagcccactacaacatcgtgaccttctgctgcaagtgcgacag caccctgagactgtgcgtgcagagcacccacgtggacatcagaaccctggaagacctgctgatgggc accctgggaatcgtgggccccatctgcagccagaagccctgagctcgctttcttgctgtccaatttc tattaaaggttcctttgttccctaagtccaactactaaactgggggatattatgaagggccttgagc atctggattctgcctaataaaaaacatttattttcattgcaaaaaaaaaaaaaaaaaaaa aaaaaaaaaaaaaaaaaaaaaaaaaaaaaaaaaaaaaaaaaaaaaaaaaaaaaaaaaaaa -continued aaaaaaaagagcactagt <SEQ ID NO: 4> HPV16 E6-E7 fusion10 mRNA-001 to 006
aggagacccaagcuacauuugcuucugacacaacuguguucacuagcaaccucaaacagacaccgcc accauggacuggaccuggauccuguuccugguggccgccgccacacgggugcacagcuuccaggacc cccaagagaggcccagaaagcugccccagcugugcaccgagcugcagaccaccauccacgacaucau ccuggaaugcguguacugcaagcagcagcuccugcggagagagguguacgacuucgccuuccgggac cugugcaucguguacagagacggcaaccccuacgccgugugcgacaagggccugaaguucuacagca agaucagcgaguaccggcacuacugcuacagccuguacggcaccacacuggaacagcaguacaacaa gccccugugcgaccugcugauccggugcaucaacugccagaaaccccugugccccgaggaaaagcag cggcaccuggacaagaagcagcgguuccacaacaucagaggccgguggacaggcagaggcaugagcu gcugccggagcagccggaccagaagagaaacccagcugagaggccggaagagaagaagccacggcga cacccccacacugcacgaguacaugcuggaccugcagcccgagacaaccgaccuguacggcuacggc cagcugaacgacagcagcgaggaagaggacgagaucgacggacccgccggacaggccgaacccgaca gagcccacuacaacaucgugaccuucugcugcaagugcgacagcacccugagacugugcgugcagag cacccacguggacaucagaacccuggaagaccugcugaugggcacccugggaaucgugggccccauc ugcagccagaagcccugagcucgcuuucuugcuguccaauuucuauuaaagguuccuuuguucccua aguccaacuacuaaacugggggauauuaugaagggccuugagcaucuggauucugccuaauaaaaaa cauuuauuuucauugcaaaaaaaaaaaaaaaaaaaaaaaaaaaaaaaaaaaaaaaaaaaaaaaaaaa aaaaaaaaaaaaaaaaaaaaaaaaaaaaaaaaaaaaaaaaaaaaaaaaaaaaagagcacuag <SEQ ID NO: 5> HPV16 E6-E7 fusion10 opt2 template DNA
GCTAGC (NheI site): nucleotide numbers 1-6
T7 promoter sequence: nucleotide numbers 8-27
5'-UTR sequence of human β-globin: nucleotide numbers 39-88
KOZAK sequence: nucleotide numbers 89-94
Coding region of IgE leader sequence: nucleotide numbers 95-148
Coding region of HPV16 E6: nucleotide numbers 149-598
Furin cleavage site: nucleotide numbers 599-619
Coding region of HPV16 E7: nucleotide numbers 620-913
3'-UTR sequence of human β-globin: nucleotide numbers 914-1045
PoylA: nucleotide numbers 1046-1147
ACTAGT (SpeI site): nucleotide numbers 1152-1157
gctagcgtaatacgactcactatagggagacccaagctacatttgcttctgacacaactgtgttcac tagcaacctcaaacagacaccgccaccatggactggacctggatcctgttcctggtggccgccgcca cacgggtgcacagcttccaggacccccaagagaggcccagaaagctgccccagctgtgcaccgagct gcagaccaccatccacgacatcatcctggaatgcgtgtactgcaagcagcagctcctgcggagagag gtgtacgacttcgccttccgggacctgtgcatcgtgtacagagacggcaacccctacgccgtgtgcg acaagggcctgaagttctacagcaagatcagcgagtaccggcactactgctacagcctgtacggcac cacactggaacagcagtacaacaagcccctgtgcgacctgctgatccggtgcatcaactgccagaaa cccctgtgccccgaggaaaagcagcggcacctggacaagaagcagcggttccacaacatcagaggcc ggtggacaggcagaggcatgagctgctgccggagcagccggaccagaagagaaacccagctgagagg ccggaagagaagaagccacggcgacacccccacactgcacgagtacatgctggacctgcagcccgag acaaccgacctgtacggctacggccagctgaacgacagcagcgaggaagaggacgagatcgacggac ccgccggacaggccgaacccgacagagcccactacaacatcgtgaccttctgctgcaagtgcgacag -continued caccctgagactgtgcgtgcagagcacccacgtggacatcagaaccctggaagacctgctgatgggc accctgggaatcgtgggccccatctgcagccagaagccctgagctcgctttcttgctgtccaatttc tattaaaggttcctttgttccctaagtccaactactaaactgggggatattatgaagggccttgagc atctggattctgcctaataaaaaacatttattttcattgcaaaaaaaaaaaaaaaaaaaa aaaaaaaaaaaaaaaaaaaaaaaaaaaaaaaaaaaaaaaaaaaaaaaaaaaaaaaaaaaa aaaaaaaagagcactagt <SEQ ID NO: 6> HPV16 E6-E7 fusion10 opt2 mRNA-001
gggagacccaagcuacauuugcuucugacacaacuguguucacuagcaaccucaaacagacaccgcc accauggacuggaccuggauccuguuccugguggccgccgccacacgggugcacagcuuccaggacc cccaagagaggcccagaaagcugccccagcugugcaccgagcugcagaccaccauccacgacaucau ccuggaaugcguguacugcaagcagcagcucccugcggagagagguguacgacuucgccuuccgggac cugugcaucguguacagagacggcaaccccuacgccgugugcgacaagggccugaaguucuacagca agaucagcgaguaccggcacuacugcuacagccuguacggcaccacacuggaacagcaguacaacaa gccccugugcgaccugcugauccggugcaucaacugccagaaaccccugugccccgaggaaaagcag cggcaccuggacaagaagcagcgguuccacaacaucagaggccgguggacaggcagaggcaugagcu gcugccggagcagccggaccagaagagaaacccagcugagaggccggaagagaagaagccacggcga cacccccacacugcacgaguacaugcuggaccugcagcccgagacaaccgaccuguacggcuacggc cagcugaacgacagcagcgaggaagaggacgagaucgacggacccgccggacaggccgaacccgaca gagcccacuacaacaucgugaccuucugcugcaagugcgacagcacccugagacugugcgugcagag cacccacguggacaucagaacccuggaagaccugcugaugggcacccugggaaucguggccccauc ugcagccagaagcccugagcucgcuuucuugcuguccaauuucuauuaaagguuccuuuguucccua aguccaacuacuaaacugggggauauuaugaagggccuugagcaucuggauucugccuaauaaaaaa cauuuauuuucauugcaaaaaaaaaaaaaaaaaaaaaaaaaaaaaaaaaaaaaaaaaaaa aaaaaaaaaaaaaaaaaaaaaaaaaaaaaaaaaaaaaaaaaaaaagagcacuag <SEQ ID NO: 7> Coding region of OVA (Ovalbumin).
atgggctccatcggcgcagcaagcatggaattttgttttgatgtattcaaggagctcaaagtccacc atgccaatgagaacatcttctactgccccattgccatcatgtcagctctagccatggtatacctggg tgcaaaagacagcaccaggacacagataaataaggttgttcgctttgataaacttccaggattcgga gacagtattgaagctcagtgtggcacatctgtaaacgttcactcttcacttagagacatcctcaacc aaatcaccaaaccaaatgatgtttattcgttcagccttgccagtagactttatgctgaagagagata cccaatcctgccagaatacttgcagtgtgtgaaggaactgtatagaggaggcttggaacctatcaac tttcaaacagctgcagatcaagccagagagctcatcaattcctgggtagaaagtcagacaaatggaa ttatcagaaatgtccttcagccaagctccgtggattctcaaactgcaatggttctggttaatgccat tgtcttcaaaggactgtgggagaaaacatttaaggatgaagacacacaagcaatgcctttcagagtg actgagcaagaaagcaaacctgtgcagatgatgtaccagattggtttatttagagtggcatcaatgg cttctgagaaaatgaagatcctggagcttccatttgccagtgggacaatgagcatgttggtgctgtt gcctgatgaagtctcaggccttgagcagcttgagagtataatcaactttgaaaaactgactgaatgg accagttctaatgttatggaagagaggaagatcaaagtgtacttacctcgcatgaagatggaggaaa aatacaacctcacatctgtcttaatggctatgggcattactgacgtgtttagctcttcagccaatct gtctggcatctcctcagcagagagcctgaagatatctcaagctgtccatgcagcacatgcagaaatc aatgaagcaggcagagaggtggtagggtcagcagaggctggagtggatgctgcaagcgtctctgaag -continued aatttagggctgaccatccattcctcttctgtatcaagcacatcgcaaccaacgccgttctcttctt tggcagatgtgtttccccttaa <SEQ ID NO: 8> Amino acid sequence of the E6 antigen of HPV16.
FQDPQERPRKLPQLCTELQTTIHDIILECVYCKQQLLRREVYDFAFRDLCIVYRDGNPYAVCD

KGLKFYSKISEYRHYCYSLYGTTLEQQYNKPLCDLLIRCINCQKPLCPEEKQRHLDKKQRFHN

IRGRWTGRGMSCCRSSRTRRETQL

<SEQ ID NO: 9> Amino acid sequence of the E7 antigen of HPV16.
HGDTPTLHEYMLDLQPETTDLYGYGQLNDSSEEEDEIDGPAGQAEPDRAHYNIVTFCCKCDS

TLRLCVQSTHVDIRTLEDLLMGTLGIVGPICSQKP

<SEQ ID NO: 10> pMA-HPV18_fusion1_opt1
GCTAGCGTAATACGACTCACTATAAGGAGACCCAAGCTACATTTGCTTCTGACACAACTG

TGTTCACTAGCAACCTCAAACAGACACCGCCACCATGGACTGGACCTGGATCCTGTTCCT

GGTGGCCGCCGCCACAAGAGTGCACAGCTTCGAGGACCCCACCAGACGGCCCTACAAGC

TGCCCGACCTGTGCACCGAGCTGAACACCAGCCTGCAGGACATCGAGATCACCTGCGTG

TACTGCAAGACCGTGCTGGAACTGACCGAGGTGTTCGAGTTCGCCTTCAAGGACCTGTTC

GTGGTGTACCGGGACAGCATCCCCCACGCCGCCTGCCACAAGGGCATCGACTTCTACAG

CCGGATCAGAGAGCTGCGGCACTACAGCGACAGCGTGTACGGCGACACCCTGGAAAAGC

TGACCAACACCGGCCTGTACAACCTGCTGATCCGGTGCCTGAGATGCCAGAAGCCCCTG

AACCCCGCCGAGAAGCTGAGACACCTGAACGAGAAGCGGCGGTTCCACAACATCGCCGG

CCACTACAGAGGCCAGGGCCACAGCTGCTGCAACCGGGCCAGACAAGAGAGACTGCAG

CGGCGGAGAGAAACCCAAGTGCGGGGCAGAAAGAGAAGAAGCCACGGCCCCAAGGCCA

CACTGCAGGACATCGTGCTGCACCTGGAACCCCAGAACGAGATCCCCGTGGACCTGCTC

GGACACGGCCAGCTGAGCGACAGCGAGGAAGAGAACGACGAGATCGACGGCGTGAACC

ACCAGCACCTGCCCGCCAGAAGGGCCGAACCACAGAGACACACCATGCTGTGCATGTGC

TGCAAGTGCGAGGCCCGGATCAAGCTGGTGGTGGAAAGCAGCGCCGACGACCTGAGAGC

CTTCCAGCAGCTGTTCCTGAACACCCTGAGCTTCGTGGGACCCTGGTGCGCCAGCCAGCA

GTGAGCTCGCTTTCTTGCTGTCCAATTTCTATTAAAGGTTCCTTTGTTCCCTAAGTCCAAC

TACTAAACTGGGGGATATTATGAAGGGCCTTGAGCATCTGGATTCTGCCTAATAAAAAAC

ATTTATTTTCATTGCAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

AAAGAGCACTAGT
NheI sequence: nucleotide numbers 1-6
T7 promoter: nucleotide numbers 7-24
A: transcription start site: nucleotide number 25
5'-UTR: nucleotide numbers 39-88
Kozak sequence: nucleotide numbers 89-94
IgE leader sequence: nucleotide numbers 95-148
HPV18 E6 sequence: nucleotide numbers 149-613
Furin recognition sequence: nucleotide numbers 614-634
HPV18 E7 sequence: nucleotide numbers 635-949
3'-UTR: nucleotide numbers 950-1081
PolyA sequence: nucleotide numbers 1082-1183
SpeI sequence: nucleotide numbers 1188-1193

<SEQ ID NO: 11> HPV18 E6-E7 fusion1 opt1 mRNA-001 and 002
AGGAGACCCAAGCUACAUUUGCUUCUGACACAACUGUGUUCACUAGCAACCUCAAACA

GACACCGCCACCAUGGACUGGACCUGGAUCCUGUUCCUGGUGGCCGCCGCCACAAGAG

UGCACAGCUUCGAGGACCCCACCAGACGGCCCUACAAGCUGCCCGACCUGUGCACCGA

GCUGAACACCAGCCUGCAGGACAUCGAGAUCACCUGCGUGUACUGCAAGACCGUGCUG

GAACUGACCGAGGUGUUCGAGUUCGCCUUCAAGGACCUGUUCGUGGUGUACCGGGAC

-continued

AGCAUCCCCCACGCCGCCUGCCACAAGGGCAUCGACUUCUACAGCCGGAUCAGAGAGC

UGCGGCACUACAGCGACAGCGUGUACGGCGACACCCUGGAAAAGCUGACCAACACCGG

CCUGUACAACCUGCUGAUCCGGUGCCUGAGAUGCCAGAAGCCCCUGAACCCCGCCGAG

AAGCUGAGACACCUGAACGAGAAGCGGCGGUUCCACAACAUCGCCGGCCACUACAGAG

GCCAGGGCCACAGCUGCUGCAACCGGGCCAGACAAGAGAGACUGCAGCGGCGGAGAGA

AACCCAAGUGCGGGGCAGAAAGAGAAGAAGCCACGGCCCCAAGGCCACACUGCAGGAC

AUCGUGCUGCACCUGGAACCCCAGAACGAGAUCCCCGUGGACCUGCUCGGACACGGCC

AGCUGAGCGACAGCGAGGAAGAGAACGACGAGAUCGACGGCGUGAACCACCAGCACCU

GCCCGCCAGAAGGGCCGAACCACAGAGACACACCAUGCUGUGCAUGUGCUGCAAGUGC

GAGGCCCGGAUCAAGCUGGUGGUGGAAAGCAGCGCCGACGACCUGAGAGCCUUCCAGC

AGCUGUUCCUGAACACCCUGAGCUUCGUGGGACCCUGGUGCGCCAGCCAGCAGUGAGC

UCGCUUUCUUGCUGUCCAAUUUCUAUUAAAGGUUCCUUUGUUCCCUAAGUCCAACUAC

UAAACUGGGGGAUAUUAUGAAGGGCCUUGAGCAUCUGGAUUCUGCCUAAUAAAAAAC

AUUUAUUUUCAUUGCAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

AAAAAGAGCACUAG

<SEQ ID NO: 12> pMA-HPV18_fusion1_opt2
GCTAGCGTAATACGACTCACTATAGGGAGACCCAAGCTACATTTGCTTCTGACACAACTG

TGTTCACTAGCAACCTCAAACAGACACCGCCACCATGGACTGGACCTGGATCCTGTTCCT

GGTGGCCGCCGCCACAAGAGTGCACAGCTTCGAGGACCCCACCAGACGGCCCTACAAGC

TGCCCGACCTGTGCACCGAGCTGAACACCAGCCTGCAGGACATCGAGATCACCTGCGTG

TACTGCAAGACCGTGCTGGAACTGACCGAGGTGTTCGAGTTCGCCTTCAAGGACCTGTTC

GTGGTGTACCGGGACAGCATCCCCCACGCCGCCTGCCACAAGGGCATCGACTTCTACAG

CCGGATCAGAGAGCTGCGGCACTACAGCGACAGCGTGTACGGCGACACCCTGGAAAAGC

TGACCAACACCGGCCTGTACAACCTGCTGATCCGGTGCCTGAGATGCCAGAAGCCCCTG

AACCCCGCCGAGAAGCTGAGACACCTGAACGAGAAGCGGCGGTTCCACAACATCGCCGG

CCACTACAGAGGCCAGGGCCACAGCTGCTGCAACCGGGCCAGACAAGAGAGACTGCAG

CGGCGGAGAGAAACCCAAGTGCGGGGCAGAAAGAGAAGAAGCCACGGCCCCAAGGCCA

CACTGCAGGACATCGTGCTGCACCTGGAACCCCAGAACGAGATCCCCGTGGACCTGCTC

GGACACGGCCAGCTGAGCGACAGCGAGGAAGAGAACGACGAGATCGACGGCGTGAACC

ACCAGCACCTGCCCGCCAGAAGGGCCGAACCACAGAGACACACCATGCTGTGCATGTGC

TGCAAGTGCGAGGCCCGGATCAAGCTGGTGGTGGAAAGCAGCGCCGACGACCTGAGAGC

CTTCCAGCAGCTGTTCCTGAACACCCTGAGCTTCGTGGGACCCTGGTGCGCCAGCCAGCA

GTGAGCTCGCTTTCTTGCTGTCCAATTTCTATTAAAGGTTCCTTTGTTCCCTAAGTCCAAC

TACTAAACTGGGGGATATTATGAAGGGCCTTGAGCATCTGGATTCTGCCTAATAAAAAAC

ATTTATTTTCATTGCAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

-continued

AAAGAGCACTAGT
NheI sequence: nucleotide numbers 1-6
T7 promoter: nucleotide numbers 7-24
G: transcription start site: nucleotide number 25
5'-UTR: nucleotide numbers 39-88
Kozak sequence: nucleotide numbers 89-94
IgE leader sequence: nucleotide numbers 95-148
HPV18 E6 sequence: nucleotide numbers 149-613
Furin recognition sequence: nucleotide numbers 614-634
HPV18 E7 sequence: nucleotide numbers 635-949
3'-UTR: nucleotide numbers 950-1081
PolyA sequence: nucleotide numbers 1082-1183
SpeI sequence: nucleotide numbers 1188-1193

<SEQ ID NO: 13> HPV18 E6-E7 fusion1 opt2 mRNA-001 and 002
GGGAGACCCAAGCUACAUUUGCUUCUGACACAACUGUGUUCACUAGCAACCUCAAACA

GACACCGCCACCAUGGACUGGACCUGGAUCCUGUUCCUGGUGGCCGCCGCCACAAGAG

UGCACAGCUUCGAGGACCCCACCAGACGGCCCUACAAGCUGCCCGACCUGUGCACCGA

GCUGAACACCAGCCUGCAGGACAUCGAGAUCACCUGCGUGUACUGCAAGACCGUGCUG

GAACUGACCGAGGUGUUCGAGUUCGCCUUCAAGGACCUGUUCGUGGUGUACCGGGAC

AGCAUCCCCCACGCCGCCUGCCACAAGGGCAUCGACUUCUACAGCCGGAUCAGAGAGC

UGCGGCACUACAGCGACAGCGUGUACGGCGACACCCUGGAAAAGCUGACCAACACCGG

CCUGUACAACCUGCUGAUCCGGUGCCUGAGAUGCCAGAAGCCCCUGAACCCCGCCGAG

AAGCUGAGACACCUGAACGAGAAGCGGCGGUUCCACAACAUCGCCGGCCACUACAGAG

GCCAGGGCCACAGCUGCUGCAACCGGGCCAGACAAGAGAGACUGCAGCGGCGGAGAGA

AACCCAAGUGCGGGGCAGAAAGAGAAGAAGCCACGGCCCCAAGGCCACACUGCAGGAC

AUCGUGCUGCACCUGGAACCCCAGAACGAGAUCCCCGUGGACCUGCUCGGACACGGCC

AGCUGAGCGACAGCGAGGAAGAGAACGACGAGAUCGACGGCGUGAACCACCAGCACCU

GCCCGCCAGAAGGGCCGAACCACAGAGACACACCAUGCUGUGCAUGUGCUGCAAGUGC

GAGGCCCGGAUCAAGCUGGUGGUGGAAAGCAGCGCCGACGACCUGAGAGCCUUCCAGC

AGCUGUUCCUGAACACCCUGAGCUUCGUGGGACCCUGGUGCGCCAGCCAGCAGUGAGC

UCGCUUUCUUGCUGUCCAAUUUCUAUUAAAGGUUCCUUUGUUCCCUAAGUCCAACUAC

UAAACUGGGGGAUAUUAUGAAGGGCCUUGAGCAUCUGGAUUCUGCCUAAUAAAAAAC

AUUUAUUUUCAUUGCAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

AAAAAGAGCACUAG

<SEQ ID NO: 14> Amino acid sequence of the E6 antigen of HPV18.
FEDPTRRPYKLPDLCTELNTSLQDIEITCVYCKTVLELTEVFEFAFKDLFVVYRDSIPHAACHK

GIDFYSRIRELRHYSDSVYGDTLEKLTNTGLYNLLIRCLRCQKPLNPAEKLRHLNEKRRFHNI

AGHYRGQGHSCCNRARQERLQRRRETQV

<SEQ ID NO: 15> Amino acid sequence of the E7 antigen of HPV18.
HGPKATLQDIVLHLEPQNEIPVDLLGHGQLSDSEEENDEIDGVNHQHLPARRAEPQRHTMLC

MCCKCEARIKLVVESSADDLRAFQQLFLNTLSFVGPWCASQQ

<SEQ ID NO: 16> Amino acid sequence of protease cleavage sequence.
RGRKRRS

<SEQ ID NO: 17> Amino acid sequence of HPV16 E6/E7 antigen fusion protein.
MDWTWILFLVAAATRVHSFQDPQERPRKLPQLCTELQTTIHDIILECVYCKQQLLRREVYDF

AFRDLCIVYRDGNPYAVCDKGLKFYSKISEYRHYCYSLYGTTLEQQYNKPLCDLLIRCINCQK

PLCPEEKQRHLDKKQRFHNIRGRWTGRGMSCCRSSRTRRETQLRGRKRRSHGDTPTLHEYM

-continued

LDLQPETTDLYGYGQLNDSSEEEDEIDGPAGQAEPDRAHYNIVTFCCKCDSTLRLCVQSTHV

DIRTLEDLLMGTLGIVGPICSQKP

<SEQ ID NO: 18> Amino acid sequence of HPV18 E6/E7 antigen fusion protein.

MDWTWILFLVAAATRVHSFEDPTRRPYKLPDLCTELNTSLQDIEITCVYCKTVLELTEVFEFA

FKDLFVVYRDSIPHAACHKGIDFYSRIRELRHYSDSVYGDTLEKLTNTGLYNLLIRCLRCQKP

LNPAEKLRHLNEKRRFHNIAGHYRGQGHSCCNRARQERLQRRRETQVRGRKRRSHGPKATL

QDIVLHLEPQNEIPVDLLGHGQLSDSEEENDEIDGVNHQHLPARRAEPQRHTMLCMCCKCEA

RIKLVVESSADDLRAFQQLFLNTLSFVGPWCASQQ

---

The invention claimed is:

1. A lipid particle comprising a cationic lipid having the structure:

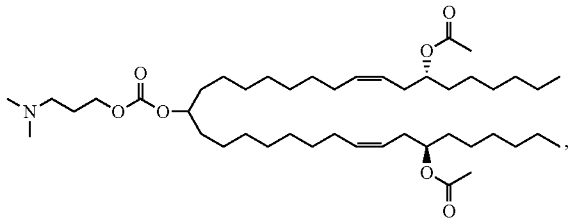 [SMILES: CCCCCC[C@H](C/C=C\CCCCCCCC(CCCCCCC/C=C\C[C@@H](CCCCCC)OC(C)=O)OC(=O)OCCCN(C)C)OC(C)=O]

or a pharmaceutically acceptable salt thereof, wherein the lipid particle encapsulates a nucleic acid molecule capable of expressing the E6 and E7 antigens of human papillomavirus, wherein the human papillomavirus is HPV16 and the nucleic acid molecule capable of expressing the E6 and E7 antigens of human papillomavirus encodes an HPV16 E6/E7 fusion protein consisting of an amino acid sequence having at least 95% identity with the amino acid sequence as shown in SEQ ID NO: 17, and wherein the nucleic acid molecule capable of expressing the E6 and E7 antigens of human papillomavirus is an mRNA molecule comprising a cap structure (Cap), 5' untranslated region (5'-UTR), a coding region of a leader sequence, E6 coding region, a protease cleavage sequence (furin cleavage site), E7 coding region, and 3' untranslated region (3'-UTR).

2. The lipid particle of claim 1, wherein the lipid particle further comprises amphipathic lipids, sterols and PEG lipids.

3. The lipid particle of claim 2, wherein the amphipathic lipid is at least one selected from the group consisting of distearoyl phosphatidylcholine, dioleoyl phosphatidylcholine and dioleoyl phosphatidylethanolamine.

4. The lipid particle of claim 2, wherein the sterol is cholesterol.

5. The lipid particle of claim 2, wherein the PEG lipid is 1,2-dimyristoyl-sn-glycerol methoxypolyethylene glycol and/or N-[methoxy poly(ethyleneglycol) carbamoyl]-1,2-dimyristyloxypropyl-3-amine.

6. The lipid particle of claim 2, wherein a total lipid content of the lipid particle is 22.5% or less of the amphipathic lipid, 15 to 55% of the sterol, 40 to 65% of the cationic lipid and 1 to 5% of the PEG lipid, each in terms of molar quantity; and the ratio of a total lipid weight to the weight of nucleic acid is 15 to 30.

7. The lipid particle of claim 6, wherein the amphipathic lipid is present at 5 to 22.5% of the total lipid content.

8. The lipid particle of claim 7, wherein the amphipathic lipid is present at 10 to 22.5% of the total lipid content.

9. The lipid particle of claim 2, wherein a total lipid content of the lipid particle is 5 to 15% of the amphipathic lipid, 35 to 50% of the sterol, 40 to 55% of the cationic lipid and 1 to 3% of the PEG lipid, each in terms of molar quantity; and the ratio of a total lipid weight of the lipid particle to the weight of nucleic acid is 15 to 30.

10. The lipid particle of claim 9, wherein the amphipathic lipid is present at 10 to 15% of the total lipid content; the sterol is present at 35 to 45% of the total lipid content; the cationic lipid is present at 40 to 50% of the total lipid content; and the PEG lipid is present at 1 to 2% of the total lipid content.

11. The lipid particle of claim 6, wherein the ratio of the total lipid weight to the weight of nucleic acid is 15 to 25.

12. The lipid particle of claim 11, wherein the ratio of the total lipid weight to the weight of nucleic acid is 15 to 22.5.

13. The lipid particle of claim 1, wherein the mRNA molecule further comprises a polyA tail (polyA).

14. The lipid particle of claim 13, wherein the sequence of the nucleic acid molecule capable of expressing the E6 and E7 antigens of HPV16 consists of a nucleotide sequence having at least 90% identity with any one of the sequences as shown in SEQ ID NOS: 2, 4 or 6.

15. The lipid particle of claim 1, wherein the nucleic acid molecule comprises at least one modified nucleotide.

16. The lipid particle of claim 15, wherein the modified nucleotide comprises at least one of 5-substituted pyrimidine nucleotide and/or pseudouridine optionally substituted at position 1.

17. The lipid particle of claim 15, wherein the modified nucleotide comprises at least one selected from the group consisting of 5-methylcytidine, 5-methoxyuridine, 5-methyluridine, pseudouridine and 1-alkylpseudouridine.

18. The lipid particle of claim 15, wherein the modified nucleotide comprises at least one selected from the group consisting of 5-methylcytidine, 5-methyluridine and 1-methylpseudouridine.

19. The lipid particle of claim 1, wherein the mean particle size is 30 nm to 300 nm.

20. A composition comprising the lipid particle of claim 1.

21. A pharmaceutical composition comprising the composition of claim 20 and a pharmaceutically acceptable carrier.

22. The lipid particle of claim 1, wherein the sequence of the nucleic acid molecule capable of expressing the E6 and E7 antigens of HPV16 consists of a nucleotide sequence having at least 90% identity with nucleotide numbers 1 to 1021 of any one of the sequences as shown in SEQ ID NOS: 2, 4 or 6.

23. A method of expressing the E6 and E7 antigens of human papillomavirus in vitro, comprising introducing into cells the composition of claim 20.

24. A method of expressing the E6 and E7 antigens of human papillomavirus in vivo, comprising administering to a mammal the composition of claim 20.

25. A method of inducing an immune response to human papillomavirus, comprising administering to a mammal the pharmaceutical composition of claim 21.

26. A method of preventing and/or treating infections with human papillomavirus, comprising administering to a mammal the pharmaceutical composition of claim 21.

27. The method of claim 26, wherein the infections are infections with HPV16.

* * * * *

SEQUENCE LISTING

<160> NUMBER OF SEQ ID NOS: 18

<210> SEQ ID NO 1
<211> LENGTH: 1157
<212> TYPE: DNA
<213> ORGANISM: Artificial Sequence
<220> FEATURE:
<223> OTHER INFORMATION: template DNA

<400> SEQUENCE: 1
gctagcgtaa tacgactcac tataaggaga cccaagctac atttgcttct gacacaactg 60
tgttcactag caacctcaaa cagacaccgc caccatggac tggacctgga tcctgtttct 120
ggtggccgct gccacacggg tgcacagctt tcaggaccct caagagaggc ccagaaagct 180
gcctcagctg tgtaccgagc tgcagaccac catccacgac atcatcctgg aatgcgtgta 240
ctgcaagcag cagctcctgc ggagagaggt gtacgatttc gccttccggg acctgtgcat 300
cgtgtacaga gatggcaacc cctacgccgt gtgcgacaag ggcctgaagt tctacagcaa 360
gatcagcgag taccggcact actgctacag cctgtacggc accacactgg aacagcagta 420
caacaagccc ctgtgcgacc tgctgatccg gtgcatcaac tgccagaaac ctctgtgccc 480
cgaggaaaag cagcggcacc tggacaagaa gcagcggttc cacaacatca gaggccggtg 540
gacaggcaga ggcatgagct gttgtcggag cagccggacc agaagagaaa cccagctgag 600
aggccggaag agaagaagcc acggcgatac ccctacactg cacgagtaca tgctggacct 660
gcagcctgag acaaccgatc tgtacggcta cggccagctg aacgacagct ctgaggaaga 720
ggacgagatc gacggacctg ctggacaggc cgaacctgat agagcccact acaatatcgt 780
gaccttctgc tgcaagtgcg acagcaccct gagactgtgt gtgcagagca cccacgtgga 840
catcagaacc ctggaagatc tgctgatggg caccctggga atcgtgggcc ctatctgtag 900
ccagaagcct tgagctcgct ttcttgctgt ccaatttcta ttaaaggttc ctttgttccc 960
taagtccaac tactaaactg ggggatatta tgaagggcct tgagcatctg gattctgcct 1020
aataaaaaac atttattttc attgcaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaagag cactagt 1157

<210> SEQ ID NO 2
<211> LENGTH: 1132
<212> TYPE: RNA
<213> ORGANISM: Artificial Sequence
<220> FEATURE:
<223> OTHER INFORMATION: HPV E6-E7 fusion 2 mRNA -continued

<400> SEQUENCE: 2

```
aggagaccca agcuacauuu gcuucugaca caacuguguu cacuagcaac cucaaacaga     60
caccgccacc auggacugga ccuggauccu guuucuggug gccgcugcca cacgggugca    120
cagcuuucag gacccucaag agaggcccag aaagcugccu cagcugugua ccgagcugca    180
gaccaccauc cacgacauca uccuggaaug cguguacugc aagcagcagc uccugcggag    240
agagguguac gauuucgccu uccgggaccu gugcaucgug uacagagaug gcaaccccua    300
cgccgugugc gacaagggcc ugaaguucua cagcaagauc agcgaguacc ggcacuacug    360
cuacagccug uacggcacca cacuggaaca gcaguacaac aagccccugu gcgaccugcu    420
gauccggugc aucaacugcc agaaaccucu gugccccgag gaaaagcagc ggcaccugga    480
caagaagcag cgguuccaca acaucagagg ccgguggaca ggcagaggca ugagcuguug    540
ucggagcagc cggaccagaa gagaaaccca gcugagaggc cggaagagaa gaagccacgg    600
cgauaccccu acacugcacg aguacaugcu ggaccugcag ccugagacaa ccgaucugua    660
cggcuacggc cagcugaacg acagcucuga ggaagaggac gagaucgacg gaccugcugg    720
acaggccgaa ccugauagag cccacuacaa uaucgugacc uucugcugca agugcgacag    780
cacccugaga cugugugugc agagcaccca cguggacauc agaacccugg aagaucugcu    840
gaugggcacc cugggaaucg ugggcccuau cuguagccag aagccuugag cucgcuuucu    900
ugcuguccaa uuucuauuaa agguuccuuu guucccuaag uccaacuacu aaacuggggg    960
auauuaugaa gggccuugag caucuggauu cugccuaaua aaaaacauuu auuuucauug   1020
caaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaagagcacu ag           1132
```

<210> SEQ ID NO 3
<211> LENGTH: 1157
<212> TYPE: DNA
<213> ORGANISM: Artificial Sequence
<220> FEATURE:
<223> OTHER INFORMATION: template DNA

<400> SEQUENCE: 3

```
gctagcgtaa tacgactcac tataaggaga cccaagctac atttgcttct gacacaactg     60
tgttcactag caacctcaaa cagacaccgc caccatggac tggacctgga tcctgttcct    120
ggtggccgcc gccacacggg tgcacagctt ccaggacccc caagagaggc ccagaaagct    180
gccccagctg tgcaccgagc tgcagaccac catccacgac atcatcctgg aatgcgtgta    240
ctgcaagcag cagctcctgc ggagagaggt gtacgacttc gccttccggg acctgtgcat    300
cgtgtacaga gacggcaacc cctacgccgt gtgcgacaag ggcctgaagt tctacagcaa    360
gatcagcgag taccggcact actgctacag cctgtacggc accacactgg aacagcagta    420
caacaagccc ctgtgcgacc tgctgatccg gtgcatcaac tgccagaaac ccctgtgccc    480
cgaggaaaag cagcggcacc tggacaagaa gcagcggttc cacaacatca gaggccggtg    540
gacaggcaga ggcatgagct gctgccggag cagccggacc agaagagaaa cccagctgag    600
aggccggaag agaagaagcc acggcgacac ccccacactg cacgagtaca tgctggacct    660
gcagcccgag acaaccgacc tgtacggcta cggccagctg aacgacagca gcgaggaaga    720
ggacgagatc gacggacccg ccggacaggc cgaacccgac agagcccact acaacatcgt    780
gaccttctgc tgcaagtgcg acagcaccct gagactgtgc gtgcagagca cccacgtgga    840
catcagaacc ctggaagacc tgctgatggg caccctggga atcgtgggcc ccatctgcag    900
```

-continued

```
ccagaagccc tgagctcgct ttcttgctgt ccaatttcta ttaaaggttc ctttgttccc    960

taagtccaac tactaaactg ggggatatta tgaagggcct tgagcatctg gattctgcct   1020

aataaaaaac atttattttc attgcaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaagag cactagt                                                  1157


<210> SEQ ID NO 4
<211> LENGTH: 1132
<212> TYPE: RNA
<213> ORGANISM: Artificial Sequence
<220> FEATURE:
<223> OTHER INFORMATION: HPV E6-E7 fusion 10 mRNA

<400> SEQUENCE: 4

aggagaccca agcuacauuu gcuucugaca caacuguguu cacuagcaac cucaaacaga     60

caccgccacc auggacugga ccuggauccu guuccuggug gccgccgcca cacgggugca    120

cagcuuccag gacccccaag agaggcccag aaagcugccc cagcugugca ccgagcugca    180

gaccaccauc cacgacauca uccuggaaug cguguacugc aagcagcagc uccugcggag    240

agagguguac gacuucgccu uccgggaccu gugcaucgug uacagagacg gcaaccccua    300

cgccgugugc gacaagggcc ugaaguucua cagcaagauc agcgaguacc ggcacuacug    360

cuacagccug uacggcacca cacuggaaca gcaguacaac aagccccugu gcgaccugcu    420

gauccggugc aucaacugcc agaaaccccu gugccccgag gaaaagcagc ggcaccugga    480

caagaagcag cgguuccaca acaucagagg ccgguggaca ggcagaggca ugagcugcug    540

ccggagcagc cggaccagaa gagaaaccca gcugagaggc cggaagagaa gaagccacgg    600

cgacaccccc acacugcacg aguacaugcu ggaccugcag cccgagacaa ccgaccugua    660

cggcuacggc cagcugaacg acagcagcga ggaagaggac gagaucgacg gacccgccgg    720

acaggccgaa cccgacagag cccacuacaa caucgugacc uucugcugca agugcgacag    780

cacccugaga cugugcgugc agagcaccca cguggacauc agaacccugg aagaccugcu    840

gaugggcacc cugggaaucg ugggccccau cugcagccag aagcccugag cucgcuuucu    900

ugcuguccaa uuucuauuaa agguuccuuu guucccuaag uccaacuacu aaacuggggg    960

auauuaugaa gggccuugag caucuggauu cugccuaaua aaaaacauuu auuuucauug   1020

caaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaagagcacu ag           1132


<210> SEQ ID NO 5
<211> LENGTH: 1157
<212> TYPE: DNA
<213> ORGANISM: Artificial Sequence
<220> FEATURE:
<223> OTHER INFORMATION: template DNA

<400> SEQUENCE: 5

gctagcgtaa tacgactcac tatagggaga cccaagctac atttgcttct gacacaactg     60

tgttcactag caacctcaaa cagacaccgc caccatggac tggacctgga tcctgttcct    120

ggtggccgcc gccacacggg tgcacagctt ccaggacccc caagagaggc ccagaaagct    180

gccccagctg tgcaccgagc tgcagaccac catccacgac atcatcctgg aatgcgtgta    240

ctgcaagcag cagctcctgc ggagagaggt gtacgacttc gccttccggg acctgtgcat    300
```

```
cgtgtacaga gacggcaacc cctacgccgt gtgcgacaag ggcctgaagt tctacagcaa    360

gatcagcgag taccggcact actgctacag cctgtacggc accacactgg aacagcagta    420

caacaagccc ctgtgcgacc tgctgatccg gtgcatcaac tgccagaaac ccctgtgccc    480

cgaggaaaag cagcggcacc tggacaagaa gcagcggttc cacaacatca gaggccggtg    540

gacaggcaga ggcatgagct gctgccggag cagccggacc agaagagaaa cccagctgag    600

aggccggaag agaagaagcc acggcgacac ccccacactg cacgagtaca tgctggacct    660

gcagcccgag acaaccgacc tgtacggcta cggccagctg aacgacagca gcgaggaaga    720

ggacgagatc gacggacccg ccggacaggc cgaacccgac agagcccact acaacatcgt    780

gaccttctgc tgcaagtgcg acagcaccct gagactgtgc gtgcagagca cccacgtgga    840

catcagaacc ctggaagacc tgctgatggg caccctggga atcgtgggcc ccatctgcag    900

ccagaagccc tgagctcgct ttcttgctgt ccaatttcta ttaaaggttc ctttgttccc    960

taagtccaac tactaaactg ggggatatta tgaagggcct tgagcatctg gattctgcct   1020

aataaaaaac atttattttc attgcaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaagag cactagt                                                  1157


<210> SEQ ID NO 6
<211> LENGTH: 1132
<212> TYPE: RNA
<213> ORGANISM: Artificial Sequence
<220> FEATURE:
<223> OTHER INFORMATION: HPV16 E6-E7 fusion 10 opt2

<400> SEQUENCE: 6

gggagaccca agcuacauuu gcuucugaca caacuguguu cacuagcaac cucaaacaga     60

caccgccacc auggacugga ccuggauccu guuccuggug gccgccgcca cacgggugca    120

cagcuuccag gacccccaag agaggcccag aaagcugccc cagcugugca ccgagcugca    180

gaccaccauc cacgacauca uccuggaaug cguguacugc aagcagcagc uccugcggag    240

agagguguac gacuucgccu uccgggaccu gugcaucgug uacagagacg gcaaccccua    300

cgccgugugc gacaagggcc ugaaguucua cagcaagauc agcgaguacc ggcacuacug    360

cuacagccug uacggcacca cacuggaaca gcaguacaac aagccccugu gcgaccugcu    420

gauccggugc aucaacugcc agaaaccccu gugccccgag gaaaagcagc ggcaccugga    480

caagaagcag cgguuccaca acaucagagg ccgguggaca ggcagaggca ugagcugcug    540

ccggagcagc cggaccagaa gagaaaccca gcugagaggc cggaagagaa gaagccacgg    600

cgacaccccc acacugcacg aguacaugcu ggaccugcag cccgagacaa ccgaccugua    660

cggcuacggc cagcugaacg acagcagcga ggaagaggac gagaucgacg gacccgccgg    720

acaggccgaa cccgacagag cccacuacaa caucgugacc uucugcugca agugcgacag    780

cacccugaga cugugcgugc agagcaccca cguggacauc agaacccugg aagaccugcu    840

gaugggcacc cugggaaucg ugggccccau cugcagccag aagcccugag cucgcuuucu    900

ugcuguccaa uuucuauuaa agguuccuuu guucccuaag uccaacuacu aaacuggggg    960

auauuaugaa gggccuugag caucuggauu cugccuaaua aaaaacauuu auuuucauug   1020

caaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaagagcacu ag           1132
```

<210> SEQ ID NO 7
<211> LENGTH: 1161
<212> TYPE: DNA
<213> ORGANISM: Gallus gallus

<400> SEQUENCE: 7

```
atgggctcca tcggcgcagc aagcatggaa ttttgttttg atgtattcaa ggagctcaaa     60

gtccaccatg ccaatgagaa catcttctac tgccccattg ccatcatgtc agctctagcc    120

atggtatacc tgggtgcaaa agacagcacc aggacacaga taaataaggt tgttcgcttt    180

gataaacttc caggattcgg agacagtatt gaagctcagt gtggcacatc tgtaaacgtt    240

cactcttcac ttagagacat cctcaaccaa atcaccaaac caaatgatgt ttattcgttc    300

agccttgcca gtagacttta tgctgaagag agatacccaa tcctgccaga atacttgcag    360

tgtgtgaagg aactgtatag aggaggcttg gaacctatca actttcaaac agctgcagat    420

caagccagag agctcatcaa ttcctgggta gaaagtcaga caaatggaat tatcagaaat    480

gtccttcagc caagctccgt ggattctcaa actgcaatgg ttctggttaa tgccattgtc    540

ttcaaaggac tgtgggagaa aacatttaag gatgaagaca cacaagcaat gcctttcaga    600

gtgactgagc aagaaagcaa acctgtgcag atgatgtacc agattggttt atttagagtg    660

gcatcaatgg cttctgagaa aatgaagatc ctggagcttc catttgccag tgggacaatg    720

agcatgttgg tgctgttgcc tgatgaagtc tcaggccttg agcagcttga gagtataatc    780

aactttgaaa aactgactga atggaccagt tctaatgtta tggaagagag gaagatcaaa    840

gtgtacttac ctcgcatgaa gatggaggaa aaatacaacc tcacatctgt cttaatggct    900

atgggcatta ctgacgtgtt tagctcttca gccaatctgt ctggcatctc ctcagcagag    960

agcctgaaga tatctcaagc tgtccatgca gcacatgcag aaatcaatga agcaggcaga   1020

gaggtggtag ggtcagcaga ggctggagtg gatgctgcaa gcgtctctga agaatttagg   1080

gctgaccatc cattcctctt ctgtatcaag cacatcgcaa ccaacgccgt tctcttcttt   1140

ggcagatgtg tttcccctta a                                              1161
```

<210> SEQ ID NO 8
<211> LENGTH: 150
<212> TYPE: PRT
<213> ORGANISM: Human papillomavirus type 16

<400> SEQUENCE: 8

```
Phe Gln Asp Pro Gln Glu Arg Pro Arg Lys Leu Pro Gln Leu Cys Thr
1               5                   10                  15

Glu Leu Gln Thr Thr Ile His Asp Ile Ile Leu Glu Cys Val Tyr Cys
            20                  25                  30

Lys Gln Gln Leu Leu Arg Arg Glu Val Tyr Asp Phe Ala Phe Arg Asp
        35                  40                  45

Leu Cys Ile Val Tyr Arg Asp Gly Asn Pro Tyr Ala Val Cys Asp Lys
    50                  55                  60

Gly Leu Lys Phe Tyr Ser Lys Ile Ser Glu Tyr Arg His Tyr Cys Tyr
65                  70                  75                  80

Ser Leu Tyr Gly Thr Thr Leu Glu Gln Gln Tyr Asn Lys Pro Leu Cys
                85                  90                  95

Asp Leu Leu Ile Arg Cys Ile Asn Cys Gln Lys Pro Leu Cys Pro Glu
            100                 105                 110

Glu Lys Gln Arg His Leu Asp Lys Lys Gln Arg Phe His Asn Ile Arg
        115                 120                 125
```

-continued

```
Gly Arg Trp Thr Gly Arg Gly Met Ser Cys Cys Arg Ser Ser Arg Thr
    130                 135                 140

Arg Arg Glu Thr Gln Leu
145                 150
```

<210> SEQ ID NO 9
<211> LENGTH: 97
<212> TYPE: PRT
<213> ORGANISM: Human papillomavirus type 16

<400> SEQUENCE: 9

```
His Gly Asp Thr Pro Thr Leu His Glu Tyr Met Leu Asp Leu Gln Pro
1               5                   10                  15

Glu Thr Thr Asp Leu Tyr Gly Tyr Gly Gln Leu Asn Asp Ser Ser Glu
            20                  25                  30

Glu Glu Asp Glu Ile Asp Gly Pro Ala Gly Gln Ala Glu Pro Asp Arg
        35                  40                  45

Ala His Tyr Asn Ile Val Thr Phe Cys Cys Lys Cys Asp Ser Thr Leu
    50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Gly Pro Ile Cys Ser Gln Lys
                85                  90                  95

Pro
```

<210> SEQ ID NO 10
<211> LENGTH: 1193
<212> TYPE: DNA
<213> ORGANISM: Artificial Sequence
<220> FEATURE:
<223> OTHER INFORMATION: pMA-HPV18 fusion1 opt1

<400> SEQUENCE: 10

```
gctagcgtaa tacgactcac tataaggaga cccaagctac atttgcttct gacacaactg     60

tgttcactag caacctcaaa cagacaccgc caccatggac tggacctgga tcctgttcct    120

ggtggccgcc gccacaagag tgcacagctt cgaggacccc accagacggc cctacaagct    180

gcccgacctg tgcaccgagc tgaacaccag cctgcaggac atcgagatca cctgcgtgta    240

ctgcaagacc gtgctggaac tgaccgaggt gttcgagttc gccttcaagg acctgttcgt    300

ggtgtaccgg gacagcatcc cccacgccgc ctgccacaag ggcatcgact tctacagccg    360

gatcagagag ctgcggcact acagcgacag cgtgtacggc gacaccctgg aaaagctgac    420

caacaccggc ctgtacaacc tgctgatccg gtgcctgaga tgccagaagc ccctgaaccc    480

cgccgagaag ctgagacacc tgaacgagaa gcggcggttc cacaacatcg ccggccacta    540

cagaggccag ggccacagct gctgcaaccg ggccagacaa gagagactgc agcggcggag    600

agaaacccaa gtgcggggca gaaagagaag aagccacggc cccaaggcca cactgcagga    660

catcgtgctg cacctggaac cccagaacga gatccccgtg gacctgctcg gacacggcca    720

gctgagcgac agcgaggaag agaacgacga gatcgacggc gtgaaccacc agcacctgcc    780

cgccagaagg gccgaaccac agagacacac catgctgtgc atgtgctgca agtgcgaggc    840

ccggatcaag ctggtggtgg aaagcagcgc cgacgacctg agagccttcc agcagctgtt    900

cctgaacacc ctgagcttcg tgggaccctg gtgcgccagc cagcagtgag ctcgctttct    960

tgctgtccaa tttctattaa aggttccttt gttccctaag tccaactact aaactggggg   1020

atattatgaa gggccttgag catctggatt ctgcctaata aaaaacattt attttcattg   1080
```

caaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaagagcact agt 1193

<210> SEQ ID NO 11
<211> LENGTH: 1168
<212> TYPE: RNA
<213> ORGANISM: Artificial Sequence
<220> FEATURE:
<223> OTHER INFORMATION: HPV18 E6-E7 fusion1 opt1 mRNA

<400> SEQUENCE: 11
aggagaccca agcuacauuu gcuucugaca caacuguguu cacuagcaac cucaaacaga 60
caccgccacc auggacugga ccuggauccu guuccuggug gccgccgcca caagagugca 120
cagcuucgag gaccccacca gacggcccua caagcugccc gaccugugca ccgagcugaa 180
caccagccug caggacaucg agaucaccug cguguacugc aagaccgugc uggaacugac 240
cgagguguuc gaguucgccu ucaaggaccu guucguggug uaccgggaca gcaucccccca 300 cgccgccugc cacaagggca ucgacuucua cagccggauc agagagcugc ggcacuacag 360
cgacagcgug uacggcgaca cccuggaaaa gcugaccaac accggccugu acaaccugcu 420
gauccggugc cugagaugcc agaagccccu gaaccccgcc gagaagcuga gacaccugaa 480
cgagaagcgg cgguuccaca acaucgccgg ccacuacaga ggccagggcc acagcugcug 540
caaccgggcc agacaagaga gacugcagcg gcggagagaa acccaagugc ggggcagaaa 600
gagaagaagc cacggcccca aggccacacu gcaggacauc gugcugcacc uggaacccca 660
gaacgagauc cccguggacc ugcucggaca cggccagcug agcgacagcg aggaagagaa 720
cgacgagauc gacggcguga accaccagca ccugcccgcc agaagggccg aaccacagag 780
acacaccaug cugugcaugu gcugcaagug cgaggcccgg aucaagcugg ugguggaaag 840
cagcgccgac gaccugagag ccuuccagca gcuguuccug aacacccuga gcuucguggg 900
acccuggugc gccagccagc agugagcucg cuuucuugcu guccaauuuc uauuaaaggu 960
uccuuuguuc ccuaagucca acuacuaaac ugggggauau uaugaagggc cuugagcauc 1020
uggauucugc cuaauaaaaa acauuuauuu ucauugcaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaag agcacuag 1168

<210> SEQ ID NO 12
<211> LENGTH: 1193
<212> TYPE: DNA
<213> ORGANISM: Artificial Sequence
<220> FEATURE:
<223> OTHER INFORMATION: pMA-HPV18 fusion1 opt2

<400> SEQUENCE: 12
gctagcgtaa tacgactcac tatagggaga cccaagctac atttgcttct gacacaactg 60
tgttcactag caacctcaaa cagacaccgc caccatggac tggacctgga tcctgttcct 120
ggtggccgcc gccacaagag tgcacagctt cgaggacccc accagacggc cctacaagct 180
gcccgacctg tgcaccgagc tgaacaccag cctgcaggac atcgagatca cctgcgtgta 240
ctgcaagacc gtgctggaac tgaccgaggt gttcgagttc gccttcaagg acctgttcgt 300
ggtgtaccgg gacagcatcc cccacgccgc ctgccacaag ggcatcgact tctacagccg 360
gatcagagag ctgcggcact acagcgacag cgtgtacggc gacaccctgg aaaagctgac 420

```
caacaccggc ctgtacaacc tgctgatccg gtgcctgaga tgccagaagc ccctgaaccc    480

cgccgagaag ctgagacacc tgaacgagaa gcggcggttc cacaacatcg ccggccacta    540

cagaggccag ggccacagct gctgcaaccg ggccagacaa gagagactgc agcggcggag    600

agaaacccaa gtgcggggca gaaagagaag aagccacggc cccaaggcca cactgcagga    660

catcgtgctg cacctggaac cccagaacga gatccccgtg gacctgctcg gacacggcca    720

gctgagcgac agcgaggaag agaacgacga gatcgacggc gtgaaccacc agcacctgcc    780

cgccagaagg gccgaaccac agagacacac catgctgtgc atgtgctgca agtgcgaggc    840

ccggatcaag ctggtggtgg aaagcagcgc cgacgacctg agagccttcc agcagctgtt    900

cctgaacacc ctgagcttcg tgggaccctg gtgcgccagc cagcagtgag ctcgctttct    960

tgctgtccaa tttctattaa aggttccttt gttccctaag tccaactact aaactggggg   1020

atattatgaa gggccttgag catctggatt ctgcctaata aaaaacattt attttcattg   1080

caaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaagagcact agt          1193
```

<210> SEQ ID NO 13
<211> LENGTH: 1168
<212> TYPE: RNA
<213> ORGANISM: Artificial Sequence
<220> FEATURE:
<223> OTHER INFORMATION: HPV18 E6-E7 fusion1 opt2 mRNA

<400> SEQUENCE: 13

```
gggagaccca agcuacauuu gcuucugaca caacuguguu cacuagcaac cucaaacaga     60

caccgccacc auggacugga ccuggauccu guuccuggug gccgccgcca caagagugca    120

cagcuucgag gaccccacca gacggcccua caagcugccc gaccugugca ccgagcugaa    180

caccagccug caggacaucg agaucaccug cguguacugc aagaccgugc uggaacugac    240

cgagguguuc gaguucgccu ucaaggaccu guucguggug uaccgggaca gcaucccccca    300

cgccgccugc cacaagggca ucgacuucua cagccggauc agagagcugc ggcacuacag    360

cgacagcgug uacggcgaca cccuggaaaa gcugaccaac accggccugu acaaccugcu    420

gauccggugc cugagaugcc agaagccccu gaaccccgcc gagaagcuga gacaccugaa    480

cgagaagcgg cgguuccaca acaucgccgg ccacuacaga ggccagggcc acagcugcug    540

caaccgggcc agacaagaga gacugcagcg gcggagagaa acccaagugc ggggcagaaa    600

gagaagaagc cacggcccca aggccacacu gcaggacauc gugcugcacc uggaacccca    660

gaacgagauc cccguggacc ugcucggaca cggccagcug agcgacagcg aggaagagaa    720

cgacgagauc gacggcguga accaccagca ccugcccgcc agaagggccg aaccacagag    780

acacaccaug cugugcaugu gcugcaagug cgaggcccgg aucaagcugg ugguggaaag    840

cagcgccgac gaccugagag ccuuccagca gcuguuccug aacacccuga gcuucguggg    900

acccuggugc gccagccagc agugagcucg cuuucuugcu guccaauuuc uauuaaaggu    960

uccuuuguuc ccuaagucca acuacuaaac uggggauau uaugaagggc cuugagcauc   1020

uggauucugc cuaauaaaaa acauuuauuu ucauugcaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaag agcacuag                                      1168
```

<210> SEQ ID NO 14
<211> LENGTH: 155

<212> TYPE: PRT
<213> ORGANISM: Human papillomavirus type 18

<400> SEQUENCE: 14

```
Phe Glu Asp Pro Thr Arg Arg Pro Tyr Lys Leu Pro Asp Leu Cys Thr
1               5                   10                  15

Glu Leu Asn Thr Ser Leu Gln Asp Ile Glu Ile Thr Cys Val Tyr Cys
            20                  25                  30

Lys Thr Val Leu Glu Leu Thr Glu Val Phe Glu Phe Ala Phe Lys Asp
        35                  40                  45

Leu Phe Val Val Tyr Arg Asp Ser Ile Pro His Ala Ala Cys His Lys
    50                  55                  60

Gly Ile Asp Phe Tyr Ser Arg Ile Arg Glu Leu Arg His Tyr Ser Asp
65                  70                  75                  80

Ser Val Tyr Gly Asp Thr Leu Glu Lys Leu Thr Asn Thr Gly Leu Tyr
                85                  90                  95

Asn Leu Leu Ile Arg Cys Leu Arg Cys Gln Lys Pro Leu Asn Pro Ala
            100                 105                 110

Glu Lys Leu Arg His Leu Asn Glu Lys Arg Arg Phe His Asn Ile Ala
        115                 120                 125

Gly His Tyr Arg Gly Gln Gly His Ser Cys Cys Asn Arg Ala Arg Gln
    130                 135                 140

Glu Arg Leu Gln Arg Arg Arg Glu Thr Gln Val
145                 150                 155
```

<210> SEQ ID NO 15
<211> LENGTH: 104
<212> TYPE: PRT
<213> ORGANISM: Human papillomavirus type 18

<400> SEQUENCE: 15

```
His Gly Pro Lys Ala Thr Leu Gln Asp Ile Val Leu His Leu Glu Pro
1               5                   10                  15

Gln Asn Glu Ile Pro Val Asp Leu Leu Gly His Gly Gln Leu Ser Asp
            20                  25                  30

Ser Glu Glu Glu Asn Asp Glu Ile Asp Gly Val Asn His Gln His Leu
        35                  40                  45

Pro Ala Arg Arg Ala Glu Pro Gln Arg His Thr Met Leu Cys Met Cys
    50                  55                  60

Cys Lys Cys Glu Ala Arg Ile Lys Leu Val Val Glu Ser Ser Ala Asp
65                  70                  75                  80

Asp Leu Arg Ala Phe Gln Gln Leu Phe Leu Asn Thr Leu Ser Phe Val
                85                  90                  95

Gly Pro Trp Cys Ala Ser Gln Gln
            100
```

<210> SEQ ID NO 16
<211> LENGTH: 7
<212> TYPE: PRT
<213> ORGANISM: Artificial Sequence
<220> FEATURE:
<223> OTHER INFORMATION: proteolytic cleavage site

<400> SEQUENCE: 16

```
Arg Gly Arg Lys Arg Arg Ser
1               5
```

<210> SEQ ID NO 17

<211> LENGTH: 272
<212> TYPE: PRT
<213> ORGANISM: Artificial Sequence
<220> FEATURE:
<223> OTHER INFORMATION: fusion protein of E6 and E7 antigens from human papillomavirus type 16

<400> SEQUENCE: 17

```
Met Asp Trp Thr Trp Ile Leu Phe Leu Val Ala Ala Ala Thr Arg Val
1               5                   10                  15

His Ser Phe Gln Asp Pro Gln Glu Arg Pro Arg Lys Leu Pro Gln Leu
            20                  25                  30

Cys Thr Glu Leu Gln Thr Thr Ile His Asp Ile Ile Leu Glu Cys Val
        35                  40                  45

Tyr Cys Lys Gln Gln Leu Leu Arg Arg Glu Val Tyr Asp Phe Ala Phe
    50                  55                  60

Arg Asp Leu Cys Ile Val Tyr Arg Asp Gly Asn Pro Tyr Ala Val Cys
65                  70                  75                  80

Asp Lys Gly Leu Lys Phe Tyr Ser Lys Ile Ser Glu Tyr Arg His Tyr
                85                  90                  95

Cys Tyr Ser Leu Tyr Gly Thr Thr Leu Glu Gln Gln Tyr Asn Lys Pro
            100                 105                 110

Leu Cys Asp Leu Leu Ile Arg Cys Ile Asn Cys Gln Lys Pro Leu Cys
        115                 120                 125

Pro Glu Glu Lys Gln Arg His Leu Asp Lys Lys Gln Arg Phe His Asn
    130                 135                 140

Ile Arg Gly Arg Trp Thr Gly Arg Gly Met Ser Cys Cys Arg Ser Ser
145                 150                 155                 160

Arg Thr Arg Arg Glu Thr Gln Leu Arg Gly Arg Lys Arg Arg Ser His
                165                 170                 175

Gly Asp Thr Pro Thr Leu His Glu Tyr Met Leu Asp Leu Gln Pro Glu
            180                 185                 190

Thr Thr Asp Leu Tyr Gly Tyr Gly Gln Leu Asn Asp Ser Ser Glu Glu
        195                 200                 205

Glu Asp Glu Ile Asp Gly Pro Ala Gly Gln Ala Glu Pro Asp Arg Ala
    210                 215                 220

His Tyr Asn Ile Val Thr Phe Cys Cys Lys Cys Asp Ser Thr Leu Arg
225                 230                 235                 240

Leu Cys Val Gln Ser Thr His Val Asp Ile Arg Thr Leu Glu Asp Leu
                245                 250                 255

Leu Met Gly Thr Leu Gly Ile Val Gly Pro Ile Cys Ser Gln Lys Pro
            260                 265                 270
```

<210> SEQ ID NO 18
<211> LENGTH: 284
<212> TYPE: PRT
<213> ORGANISM: Artificial Sequence
<220> FEATURE:
<223> OTHER INFORMATION: fusion protein of E6 and E7 antigens from human papillomacvirus type 18

<400> SEQUENCE: 18

```
Met Asp Trp Thr Trp Ile Leu Phe Leu Val Ala Ala Ala Thr Arg Val
1               5                   10                  15

His Ser Phe Glu Asp Pro Thr Arg Arg Pro Tyr Lys Leu Pro Asp Leu
            20                  25                  30

Cys Thr Glu Leu Asn Thr Ser Leu Gln Asp Ile Glu Ile Thr Cys Val
        35                  40                  45
```

-continued

```
Tyr Cys Lys Thr Val Leu Glu Leu Thr Glu Val Phe Glu Phe Ala Phe
    50                  55                  60

Lys Asp Leu Phe Val Val Tyr Arg Asp Ser Ile Pro His Ala Ala Cys
65                  70                  75                  80

His Lys Gly Ile Asp Phe Tyr Ser Arg Ile Arg Glu Leu Arg His Tyr
                85                  90                  95

Ser Asp Ser Val Tyr Gly Asp Thr Leu Glu Lys Leu Thr Asn Thr Gly
            100                 105                 110

Leu Tyr Asn Leu Leu Ile Arg Cys Leu Arg Cys Gln Lys Pro Leu Asn
        115                 120                 125

Pro Ala Glu Lys Leu Arg His Leu Asn Glu Lys Arg Arg Phe His Asn
    130                 135                 140

Ile Ala Gly His Tyr Arg Gly Gln Gly His Ser Cys Cys Asn Arg Ala
145                 150                 155                 160

Arg Gln Glu Arg Leu Gln Arg Arg Arg Glu Thr Gln Val Arg Gly Arg
                165                 170                 175

Lys Arg Arg Ser His Gly Pro Lys Ala Thr Leu Gln Asp Ile Val Leu
            180                 185                 190

His Leu Glu Pro Gln Asn Glu Ile Pro Val Asp Leu Leu Gly His Gly
        195                 200                 205

Gln Leu Ser Asp Ser Glu Glu Glu Asn Asp Glu Ile Asp Gly Val Asn
    210                 215                 220

His Gln His Leu Pro Ala Arg Arg Ala Glu Pro Gln Arg His Thr Met
225                 230                 235                 240

Leu Cys Met Cys Cys Lys Cys Glu Ala Arg Ile Lys Leu Val Val Glu
                245                 250                 255

Ser Ser Ala Asp Asp Leu Arg Ala Phe Gln Gln Leu Phe Leu Asn Thr
            260                 265                 270

Leu Ser Phe Val Gly Pro Trp Cys Ala Ser Gln Gln
        275                 280
```